(12) United States Patent
Hyde et al.

(10) Patent No.: US 9,358,361 B2
(45) Date of Patent: *Jun. 7, 2016

(54) METHODS AND SYSTEMS FOR PRESENTING A COMBINATION TREATMENT

(71) Applicant: The Invention Science Fund I, LLC, Bellevue, WA (US)

(72) Inventors: Roderick A. Hyde, Redmond, WA (US); Muriel Y. Ishikawa, Livermore, CA (US); Eric C. Leuthardt, St. Louis, MO (US); Royce A. Levien, Lexington, MA (US); Robert W. Lord, Seattle, WA (US); Mark A. Malamud, Seattle, WA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/181,540

(22) Filed: Feb. 14, 2014

(65) Prior Publication Data
US 2014/0275739 A1 Sep. 18, 2014

Related U.S. Application Data

(63) Continuation of application No. 12/315,366, filed on Dec. 1, 2008, which is a continuation of application No. 12/315,072, filed on Nov. 26, 2008, now Pat. No. 8,682,687, application No. 14/181,540, which is a
(Continued)

(51) Int. Cl.
*A61B 5/00* (2006.01)
*A61M 21/02* (2006.01)
(Continued)

(52) U.S. Cl.
CPC ........... *A61M 21/02* (2013.01); *G06F 19/3456* (2013.01); *G06F 19/3481* (2013.01); *G06Q 50/24* (2013.01); *A61M 2021/005* (2013.01); *A61M 2021/0077* (2013.01)

(58) Field of Classification Search
CPC ........... G06F 19/3456; G06F 19/3481; G06F 19/3462; G06Q 50/24
USPC .......................................................... 705/2
See application file for complete search history.

(56) References Cited

U.S. PATENT DOCUMENTS 3,036,568 A   5/1962   Stark
4,570,640 A   2/1986   Barsa
(Continued)

FOREIGN PATENT DOCUMENTS

JP   2004-206578 A   7/2004
WO   WO 99/04043      1/1999
(Continued)

OTHER PUBLICATIONS

Beck et al.; "Virtual Reality Exposure Therapy for PTSD Symptoms After a Road Accident: An Uncontrolled Case Series"; Behavior Therapy; bearing a date of Sep. 22, 2006; pp. 39-48; vol. 38; Elsevier Ltd.
(Continued)

*Primary Examiner* — Hiep V Nguyen

(57) ABSTRACT

Methods, computer program products, and systems are described that include accepting an indication of a schedule for administration of a bioactive agent to an individual and presenting an indication of an artificial sensory experience at least partly based on the accepting an indication of the schedule for administration of the bioactive agent to the individual.

24 Claims, 55 Drawing Sheets

Related U.S. Application Data continuation-in-part of application No. 12/157,922, filed on Jun. 13, 2008, which is a continuation-in-part of application No. 12/150,122, filed on Apr. 24, 2008, application No. 14/181,540, which is a continuation-in-part of application No. 12/157,160, filed on Jun. 6, 2008, now Pat. No. 8,876,688, which is a continuation of application No. 12/152,266, filed on May 13, 2008, now abandoned, application No. 14/181,540, which is a continuation-in-part of application No. 12/157,989, filed on Jun. 13, 2008, which is a continuation of application No. 12/152,266, filed on May 13, 2008, now abandoned, application No. 14/181,540, which is a continuation-in-part of application No. 12/214,547, filed on Jun. 19, 2008, now Pat. No. 7,801,686, which is a continuation of application No. 12/154,275, filed on May 21, 2008, now Pat. No. 7,974,787, application No. 14/181,540, which is a continuation-in-part of application No. 12/156,440, filed on May 30, 2008, and a continuation-in-part of application No. 12/156,949, filed on Jun. 5, 2008, and a continuation-in-part of application No. 12/217,620, filed on Jul. 7, 2008, now Pat. No. 8,606,592, which is a continuation of application No. 12/217,509, filed on Jul. 3, 2008, now Pat. No. 9,064,036, application No. 14/181,540, which is a continuation-in-part of application No. 12/218,627, filed on Jul. 16, 2008, which is a continuation of application No. 12/218,503, filed on Jul. 15, 2008, application No. 14/181,540, which is a continuation-in-part of application No. 12/220,706, filed on Jul. 25, 2008, and a continuation-in-part of application No. 12/229,612, filed on Aug. 25, 2008, now abandoned, which is a continuation of application No. 12/229,531, filed on Aug. 22, 2008, now Pat. No. 9,282,927, application No. 14/181,540, which is a continuation-in-part of application No. 12/283,742, filed on Sep. 15, 2008, now Pat. No. 8,615,407, which is a continuation of application No. 12/283,619, filed on Sep. 12, 2008, now Pat. No. 8,930,208, application No. 14/181,540, which is a continuation-in-part of application No. 12/286,730, filed on Sep. 30, 2008, which is a continuation of application No. 12/286,751, filed on Sep. 30, 2008, application No. 14/181,540, which is a continuation-in-part of application No. 12/287,886, filed on Oct. 14, 2008, which is a continuation of application No. 12/287,686, filed on Oct. 10, 2008, application No. 14/181,540, which is a continuation-in-part of application No. 12/290,456, filed on Oct. 29, 2008, now Pat. No. 9,026,369, which is a continuation of application No. 12/290,227, filed on Oct. 28, 2008.

(51) Int. Cl.
  *G06F 19/00* (2011.01)
  *G06Q 50/24* (2012.01)
  *A61M 21/00* (2006.01)

(56) References Cited

U.S. PATENT DOCUMENTS

| | | |
|---|---|---|
| 4,734,585 A | 3/1988 | Owers |
| 4,755,043 A | 7/1988 | Carter |
| 4,962,491 A | 10/1990 | Schaeffer |
| 4,973,149 A | 11/1990 | Hutchinson |
| 4,974,729 A | 12/1990 | Steinnagel |
| 5,099,463 A | 3/1992 | Lloyd et al. |
| 5,135,752 A | 8/1992 | Snipes |
| 5,197,941 A | 3/1993 | Whitaker |
| 5,200,891 A | 4/1993 | Kehr et al. |
| 5,277,188 A | 1/1994 | Selker |
| 5,348,268 A | 9/1994 | Klein |
| 5,408,443 A | 4/1995 | Weinberger |
| 5,463,564 A | 10/1995 | Agrafiotis et al. |
| 5,508,042 A * | 4/1996 | Oshlack et al. ............ 424/468 |
| 5,577,981 A | 11/1996 | Jarvik |
| 5,610,674 A * | 3/1997 | Martin ............ 352/85 |
| 5,645,072 A | 7/1997 | Thrall et al. |
| 5,646,629 A | 7/1997 | Loomis et al. |
| 5,671,752 A | 9/1997 | Sinderby et al. |
| 5,722,418 A * | 3/1998 | Bro ............ 600/545 |
| 5,722,754 A | 3/1998 | Langner |
| 5,724,983 A | 3/1998 | Selker et al. |
| 5,725,472 A | 3/1998 | Weathers |
| 5,822,726 A | 10/1998 | Taylor et al. |
| 5,845,255 A | 12/1998 | Mayaud |
| 5,846,086 A | 12/1998 | Bizzi et al. |
| 5,891,049 A | 4/1999 | Cyrus et al. |
| 5,919,141 A | 7/1999 | Money et al. |
| 6,012,926 A | 1/2000 | Hodges et al. |
| 6,053,866 A | 4/2000 | McLeod |
| 6,067,523 A | 5/2000 | Bair et al. |
| 6,102,846 A | 8/2000 | Patton et al. |
| 6,149,586 A | 11/2000 | Elkind |
| 6,152,563 A | 11/2000 | Hutchinson et al. |
| 6,168,562 B1 | 1/2001 | Miller et al. |
| 6,186,145 B1 * | 2/2001 | Brown ............ 128/897 |
| 6,198,953 B1 | 3/2001 | Webster et al. |
| 6,244,987 B1 | 6/2001 | Ohsuga et al. |
| 6,282,458 B1 | 8/2001 | Murayama et al. |
| 6,314,384 B1 | 11/2001 | Goetz |
| 6,315,719 B1 | 11/2001 | Rode et al. |
| 6,334,778 B1 | 1/2002 | Brown |
| 6,368,111 B2 | 4/2002 | Legarda |
| 6,383,135 B1 | 5/2002 | Chikovani et al. |
| 6,390,453 B1 | 5/2002 | Frederickson et al. |
| 6,397,080 B1 | 5/2002 | Viktorsson et al. |
| 6,421,650 B1 | 7/2002 | Goetz et al. |
| 6,425,764 B1 | 7/2002 | Lamson |
| 6,435,878 B1 | 8/2002 | Reynolds et al. |
| 6,448,030 B1 | 9/2002 | Rust et al. |
| 6,487,520 B1 | 11/2002 | Kurtzberg et al. |
| 6,542,858 B1 * | 4/2003 | Grass et al. ............ 703/2 |
| 6,561,811 B2 | 5/2003 | Rapoza et al. |
| 6,565,359 B2 | 5/2003 | Calhoun et al. |
| 6,579,231 B1 | 6/2003 | Phipps |
| 6,631,291 B2 | 10/2003 | Viertio-Oja et al. |
| 6,647,358 B2 | 11/2003 | Grass et al. |
| 6,702,767 B1 | 3/2004 | Douglas et al. |
| 6,723,527 B2 | 4/2004 | Petit et al. |
| 6,807,492 B2 | 10/2004 | Oren et al. |
| 6,826,498 B2 | 11/2004 | Birkner et al. |
| 6,832,178 B1 | 12/2004 | Fernandez et al. |
| 6,852,069 B2 | 2/2005 | Park |
| 6,886,653 B1 | 5/2005 | Bellehumeur |
| 6,909,359 B1 | 6/2005 | McGovern |
| 6,947,790 B2 * | 9/2005 | Gevins et al. ............ 600/544 |
| 6,952,695 B1 | 10/2005 | Trinks et al. |
| 6,968,375 B1 | 11/2005 | Brown |
| 6,997,880 B2 | 2/2006 | Carlebach et al. |
| 7,002,476 B2 | 2/2006 | Rapchak |
| 7,033,025 B2 | 4/2006 | Winterbotham |
| 7,039,878 B2 | 5/2006 | Auer et al. |
| 7,044,911 B2 | 5/2006 | Drinan et al. |
| 7,049,103 B2 | 5/2006 | Ishiguro et al. |
| 7,076,437 B1 | 7/2006 | Levy |
| 7,084,874 B2 | 8/2006 | Kurzweil |
| 7,144,680 B2 | 12/2006 | Park et al. |
| 7,148,208 B2 | 12/2006 | Barkan et al. |
| 7,161,579 B2 | 1/2007 | Daniel |
| 7,177,675 B2 | 2/2007 | Suffin et al. |
| 7,197,492 B2 | 3/2007 | Sullivan |
| 7,198,044 B2 | 4/2007 | Trueba |
| 7,226,164 B2 | 6/2007 | Abourizk et al. |
| 7,229,288 B2 | 6/2007 | Stuart et al. |
| 7,245,956 B2 | 7/2007 | Matthews et al. |
| 7,272,431 B2 | 9/2007 | McGrath |

(56) References Cited

U.S. PATENT DOCUMENTS

| | | | |
|---|---|---|---|
| 7,294,107 B2 | 11/2007 | Simon et al. | |
| 7,353,065 B2 | 4/2008 | Morrell | |
| 7,461,651 B2 | 12/2008 | Brown | |
| 7,513,622 B2 | 4/2009 | Khaderi | |
| 7,575,865 B2 | 8/2009 | Leamon et al. | |
| 7,623,927 B2 | 11/2009 | Rezai | |
| 7,827,044 B2 | 11/2010 | McCullough | |
| 7,890,340 B2 | 2/2011 | Abraham-Fuchs et al. | |
| 7,942,818 B2 | 5/2011 | Euliano et al. | |
| 8,150,629 B2 | 4/2012 | Geerts et al. | |
| 8,160,901 B2* | 4/2012 | Heywood | A61B 5/0002 705/3 |
| 2001/0001144 A1 | 5/2001 | Kapp | |
| 2001/0010541 A1 | 8/2001 | Fernandez et al. | |
| 2002/0044152 A1 | 4/2002 | Abbott, III et al. | |
| 2002/0091546 A1 | 7/2002 | Christakis et al. | |
| 2002/0103428 A1 | 8/2002 | deCharms | |
| 2002/0103429 A1 | 8/2002 | deCharms | |
| 2002/0128061 A1 | 9/2002 | Blanco | |
| 2002/0165466 A1 | 11/2002 | Givens et al. | |
| 2002/0198438 A1 | 12/2002 | Cromer et al. | |
| 2003/0036683 A1 | 2/2003 | Kehr et al. | |
| 2003/0036744 A1 | 2/2003 | Struys et al. | |
| 2003/0065294 A1 | 4/2003 | Pickup et al. | |
| 2003/0077300 A1 | 4/2003 | Wermeling | |
| 2003/0139933 A1 | 7/2003 | Kimmel | |
| 2003/0144884 A1 | 7/2003 | Mayaud | |
| 2003/0214630 A1 | 11/2003 | Winterbotham | |
| 2003/0225362 A1 | 12/2003 | Currie et al. | |
| 2004/0010511 A1 | 1/2004 | Gogolak | |
| 2004/0024287 A1 | 2/2004 | Patton et al. | |
| 2004/0024616 A1 | 2/2004 | Spector et al. | |
| 2004/0030581 A1 | 2/2004 | Leven | |
| 2004/0078027 A1 | 4/2004 | Shachar | |
| 2004/0078239 A1 | 4/2004 | Dacosta | |
| 2004/0087576 A1 | 5/2004 | Haracz | |
| 2004/0092809 A1* | 5/2004 | DeCharms | 600/410 |
| 2004/0123667 A1 | 7/2004 | McGrath | |
| 2004/0127778 A1 | 7/2004 | Lambert et al. | |
| 2004/0172285 A1 | 9/2004 | Gibson | |
| 2004/0196184 A1 | 10/2004 | Hollander et al. | |
| 2004/0208923 A1 | 10/2004 | Davis et al. | |
| 2005/0021372 A1 | 1/2005 | Mikkelsen et al. | |
| 2005/0027284 A1 | 2/2005 | Lozano et al. | |
| 2005/0054942 A1 | 3/2005 | Melker et al. | |
| 2005/0054958 A1 | 3/2005 | Hoffmann | |
| 2005/0065813 A1 | 3/2005 | Mishelevich et al. | |
| 2005/0086077 A1 | 4/2005 | Forman | |
| 2005/0124851 A1 | 6/2005 | Patton et al. | |
| 2005/0124878 A1 | 6/2005 | Sharony | |
| 2005/0165115 A1 | 7/2005 | Murphy et al. | |
| 2005/0188853 A1* | 9/2005 | Scannell, Jr. | A01G 9/02 96/417 |
| 2005/0197654 A1 | 9/2005 | Edman et al. | |
| 2005/0240084 A1 | 10/2005 | Morice et al. | |
| 2005/0277911 A1 | 12/2005 | Stewart et al. | |
| 2006/0031099 A1* | 2/2006 | Vitello et al. | 705/2 |
| 2006/0058694 A1 | 3/2006 | Clark et al. | |
| 2006/0059145 A1 | 3/2006 | Henschke et al. | |
| 2006/0062852 A1 | 3/2006 | Holmes | |
| 2006/0084877 A1 | 4/2006 | Ujhazy et al. | |
| 2006/0111644 A1 | 5/2006 | Guttag et al. | |
| 2006/0161408 A1 | 7/2006 | Bachman et al. | |
| 2006/0161456 A1 | 7/2006 | Baker et al. | |
| 2006/0183980 A1 | 8/2006 | Yang | |
| 2006/0235724 A1 | 10/2006 | Rosenthal | |
| 2006/0241718 A1 | 10/2006 | Tyler et al. | |
| 2006/0247489 A1 | 11/2006 | Carbis et al. | |
| 2006/0252761 A1 | 11/2006 | Davis et al. | |
| 2006/0265253 A1 | 11/2006 | Rao et al. | |
| 2007/0016265 A1 | 1/2007 | Davoodi et al. | |
| 2007/0067186 A1 | 3/2007 | Brenner et al. | |
| 2007/0072821 A1 | 3/2007 | Iakoubova et al. | |
| 2007/0088404 A1 | 4/2007 | Wyler et al. | |
| 2007/0098778 A1 | 5/2007 | Borsadia | |
| 2007/0112277 A1 | 5/2007 | Fischer et al. | |
| 2007/0112624 A1 | 5/2007 | Jung et al. | |
| 2007/0123783 A1 | 5/2007 | Chang | |
| 2007/0136093 A1 | 6/2007 | Rankin et al. | |
| 2007/0167853 A1 | 7/2007 | Melker et al. | |
| 2007/0172814 A1 | 7/2007 | Li | |
| 2007/0179534 A1 | 8/2007 | Firlik et al. | |
| 2007/0191704 A1* | 8/2007 | DeCharms | 600/411 |
| 2007/0213981 A1 | 9/2007 | Meyerhoff et al. | |
| 2008/0045832 A1 | 2/2008 | McGrath | |
| 2008/0046286 A1 | 2/2008 | Halsted | |
| 2008/0076972 A1 | 3/2008 | Dorogusker et al. | |
| 2008/0097167 A1 | 4/2008 | Yudkovitch et al. | |
| 2008/0125978 A1 | 5/2008 | Robson et al. | |
| 2008/0132383 A1 | 6/2008 | Einav et al. | |
| 2008/0133265 A1 | 6/2008 | Silkaitis et al. | |
| 2008/0139870 A1 | 6/2008 | Gliner et al. | |
| 2008/0139902 A1 | 6/2008 | Kotulla et al. | |
| 2008/0146334 A1 | 6/2008 | Kil | |
| 2008/0146888 A1 | 6/2008 | Azzaro et al. | |
| 2008/0167571 A1 | 7/2008 | Gevins | |
| 2008/0172044 A1 | 7/2008 | Shelton | |
| 2008/0177197 A1 | 7/2008 | Lee et al. | |
| 2008/0212847 A1 | 9/2008 | Davies et al. | |
| 2008/0214902 A1 | 9/2008 | Lee et al. | |
| 2008/0214903 A1 | 9/2008 | Orbach | |
| 2008/0221847 A1 | 9/2008 | Fenetteau | |
| 2008/0226730 A1 | 9/2008 | Schmitke et al. | |
| 2008/0242947 A1 | 10/2008 | Jung et al. | |
| 2008/0243544 A1 | 10/2008 | Cafer | |
| 2008/0267447 A1 | 10/2008 | Kelusky et al. | |
| 2008/0275731 A1 | 11/2008 | Rao et al. | |
| 2008/0278682 A1 | 11/2008 | Huxlin et al. | |
| 2008/0305518 A1 | 12/2008 | Klausen et al. | |
| 2009/0009718 A1 | 1/2009 | Legatt | |
| 2009/0048506 A1 | 2/2009 | Fong-Ichimura et al. | |
| 2009/0149769 A1 | 6/2009 | Pettigrew | |
| 2009/0171697 A1 | 7/2009 | Glauser et al. | |
| 2009/0299763 A1* | 12/2009 | Sakurada | G06Q 50/22 705/2 |
| 2009/0306741 A1 | 12/2009 | Hogle et al. | |
| 2009/0312817 A1 | 12/2009 | Hogle et al. | |
| 2010/0015184 A1 | 1/2010 | Tuel | |
| 2010/0094202 A1 | 4/2010 | Edginton et al. | |
| 2010/0163027 A1 | 7/2010 | Hyde et al. | |
| 2010/0168525 A1 | 7/2010 | Hyde et al. | |
| 2010/0168602 A1 | 7/2010 | Hyde et al. | |
| 2010/0324874 A9 | 12/2010 | Bangs et al. | |

FOREIGN PATENT DOCUMENTS

| | | |
|---|---|---|
| WO | WO 03/048789 A2 | 6/2003 |
| WO | WO 2006/048417 A1 | 5/2006 |
| WO | WO 2006/090371 A2 | 8/2006 |
| WO | WO 2007/016241 A1 | 2/2007 |
| WO | WO 2007/068983 A1 | 6/2007 |
| WO | WO 2007/141373 A2 | 12/2007 |

OTHER PUBLICATIONS

Foa et al.; "Guidelines for Treatment of PTSD"; Journal of Traumatic Stress; 2000; pp. 539-588; vol. 13, No. 4; Reprinted with permission from "*Effective Treatments for PTSD*"; Foa et al.; Guilford Press.

Garcia-Palacios et al.; "Virtual reality in the treatment of spider phobia: a controlled study"; Behaviour Research and Therapy; bearing a date of Jul. 1, 2001; pp. 983-993; vol. 40; Elsevier Science Ltd.

Valva et al.; "Fright (Effroi) and Other Peritraumatic Responses After a Serious Motor Vehicle Accident: Prospective Influence on Acute PTSD Development"; The Canadian Journal of Psychiatry-Original Research; bearing a date of Jul. 2003; pp. 395-401; vol. 48, No. 6.

Walshe et al.; "Exploring the Use of Computer Games and Virtual Reality in Exposure Therapy for Fear of Driving Following a Motor Vehicle Accident"; CyberPsychology & Behavior; bearing a date of 2003; pp. 329-334; vol. 6, No. 3; Mary Ann Liebert, Inc.

Wiederhold et al.; "Fear of Flying: A Case Report Using Virtual Reality Therapy with Physiological Monitoring"; Cyber Psychology and Behavior; 1998; pp. 97-103; vol. 1, No. 2; Mary Ann Liebert, Inc.

(56) References Cited

OTHER PUBLICATIONS

Wiederhold et al.; "Physiological Monitoring as an Objective Tool in Virtual Reality Therapy"; CyberPsychology & Behavior; bearing a date of 2002; pp. 77-82; vol. 5, No. 1; Mary Ann Liebert, Inc.
U.S. Appl. No. 12/584,200, Leuthardt et al.
U.S. Appl. No. 12/584,129, Leuthardt et al.
U.S. Appl. No. 12/462,404, Leuthardt et al.
U.S. Appl. No. 12/462,344, Leuthardt et al.
U.S. Appl. No. 12/462,197, Leuthardt et al.
U.S. Appl. No. 12/462,129, Leuthardt et al.
U.S. Appl. No. 12/460,327, Leuthardt et al.
U.S. Appl. No. 12/460,252, Leuthardt et al.
U.S. Appl. No. 12/459,623, Leuthardt et al.
U.S. Appl. No. 12/459,493, Leuthardt et al.
U.S. Appl. No. 12/459,386, Leuthardt et al.
"Alter" Excerpt from the Merriam-Webster English Dictionary; Printed on Jul. 8, 2013; total of 4 pages; Merriam-Webster Incorporated.
Axelrod, Lesley et al.; "Smoke and mirrors: gathering user requirements for emerging affective systems"; bearing a date of Jun. 7-10, 2004; pp. 323-328; vol. 1; 26$^{th}$International Conference on Information Technology Interfaces, 2004.
Baños et al.; "Virtual Reality Treatment of Flying Phobia"; IEEE Transactions on Information Technology in Biomedicine; Sep. 2002; pp. 206-212; vol. 6, No. 3; IEEE.
Barrientos, Ruth M. et al.; "Memory for context is impaired by injecting anisomycin into dorsal hippocampus following context exploration"; Behavioural Brain Research; bearing a date of Aug. 21, 2002; pp. 299-306; vol. 134, Issues 1-2; Elsevier Science B.V. (abstract only).
U.S. Appl. No. 12/459,287, Leuthardt et al.
U.S. Appl. No. 12/459,195, Leuthardt et al.
U.S. Appl. No. 12/459,029, Leuthardt et al.
U.S. Appl. No. 12/455,308, Leuthardt et al.
U.S. Appl. No. 12/455,148, Leuthardt et al.
U.S. Appl. No. 12/387,961, Leuthardt et al.
Basso, M. R., Jr.; "Neurobiological Relationships Between Ambient Lighting and the Startle Response to Acoustic Stress in Humans"; bearing a date of Sep. 2001; pp. 147-157; vol. 110 No. 3-4; International Journal of Neuroscience [Abstract Only].
Bayard, Max, M.D. et al.; "Alcohol Withdrawal Syndrome"; American Family Physician; bearing a date of Mar. 15, 2004; pp. 1443-1450; vol. 69, No. 6.
Bonson, Katherine R.; "Hallucinogenic Drugs"; Encyclopedia of Life Sciences; bearing a date of 2001; pp. 1-7; Nature Publishing Group.
Bosworth, Kris et al.; "A Computer-Based Violence Prevention Intervention for Young Adolescents: A Pilot Study"; Adolescence; bearing a date Winter 1998; pp. 785-796; vol. 33 No. 132; Libra Publishers, Inc. [Abstract Only].
"Brain-Reading Headset to Sell for $299"; bearing a date of Feb. 20, 2008; pp. 1-2; Associated Press; located at http://finance.myway.com/jsp/nw/nwdt_rt.jsp?section=news&feed=ap&src=601&newsid=.
Canadas-Quesada, F. J. et al.; "Improvement of Perceived Stiffness Using Auditory Stimuli in Haptic Virtual Realty"; IEEE Melecon; bearing a date of May 16-19, 2006; published in Benalmadena, Spain.
Carney, Russell N. et al.; Mnemonic Instruction, With a Focus on Transfer; bearing a date of Dec. 2000; pp. 783-790; vol. 92, No. 4; Journal of Educational Psychology [Abstract Only].
Clarke, Peter; IMEC Has a Brain Wave: Feed EEG Emotion Back Into Games; EE Times online; bearing a date of Nov. 1, 2007; pp. 1-2; located at http://www.eetimes.eu/design/202801063.
Coelho et al.; "*Research Article* Deconstructing Acrophobia: Physiological and Psychological Precursors to Developing a Fear of Heights"; Depression and Anxiety; bearing a date of Apr. 8, 2010; pp. 864-870; vol. 27; Wiley-Liss, Inc.

Cohn, J. N.; "Introduction to Surrogate Markers"; Circulation; bearing a date of 2004; pp. 1-3; vol. 109; American Heart Association; located at http://circ.ahajournals.org/cgi/content/full/109/25_suppl_IV-20.
Davis, Michael et al.; "Combining Pharmacotherapy With Cognitive Behavioral Therapy: Traditional and New Approaches"; Journal of Traumatic Stress; bearing a date of Oct. 2006; pp. 571-581; vol. 19, No. 5; InterScience.
Difede, Joann, Ph.D. et al.; "Virtual Reality Exposure Therapy for World Trade Center Post-traumatic Stress Disorder: A Case Report"; CyberPsychology & Behavior; 2002; pp. 529-535; vol. 5, No. 6; CyberPsychology & Behavior.
Faris, Robert E.L.; "Cultural Isolation and the Schizophrenic Personality"; The American Journal of Sociology; bearing a date of Sep. 1934; pp. 155-164; vol. 40, No. 2; University of Chicago Press; located at http://www.jstor.org/pss/2768057; [Abstract Only].
Gould, Neda et al.; "Performance on a Virtual Reality Spatial Memory Navigation Task in Depressed Patients"; American Journal of Psychiatry; bearing a date of Mar. 10, 2007; pp. 516-519; vol. 164.
Gorini, Alessandra, et al.; "Virtual Worlds, Real Healing"; Science; bearing a date of Dec. 7, 2007; p. 1549; vol. 318; No. 5856; AAS.
Green, T. et al.; "PC-Based Medical Data Acquisition and Analysis"; bearing a date of 1995; p. 159; 8$^{th}$ IEEE Symposium on Computer-Based Medical Systems (CBMS) '95 [Abstract Only].
Greenland, Sander et al.; Methods for Trend Estimation from Summarized Dose-Response Data, with Applications to Meta-Analysis; American Journal of Epidemiology; bearing a date of 1992; pp. 1301-1309; vol. 135, No. 11; located at http://aje.oxfordjournals.org/cgi/content/abstract/135/11/1301 [Abstract Only].
Grollman, Arthur P ; "Inhibitors of Protein Biosynthesis"; The Journal of Biological Chemistry; bearing a date of Jul. 10, 1967; pp. 3266-3233; vol. 242, No. 13.
Grossman, E. et al.; "Breathing-Control Lowers Blood Pressure"; Journal of Human Hypertension; bearing a date of Apr. 2001; pp. 263-269; vol. 15, No. 4; Nature Publishing Group.
Harland, C.J. et al.; "Electric potential probes—new directions in the remote sensing of the human body"; Measurement Science and Technology; bearing a date of 2002; pp. 163-169; vol. 13; Institute of Physics Publishing.
Harland, C.J. et al.; "High Resolution Ambulatory Electrocardiographic Monitoring Using Wrist-Mounted Electric Potential Sensors"; Measuring Science and Technology; bearing a date of May 23, 2003; pp. 923-928; vol. 14; IOP Publishing Ltd.
Harland, C.J. et al.; "Remote Detection of Human Electroencephalograms Using Ultrahigh Input Impedance Electric Potential Sensors"; Applied Physics Letters; bearing a date of Oct. 21, 2002; pp. 3284-3286; vol. 81, No. 17; American Institute of Physics.
Hoffman, Hunter G., Ph.D. et al.; "The Analgesic Effects of Opioids and Immersive Virtual Realty Distraction: Evidence From Subjective and Functional Brain Imaging Assessments"; bearing a date of Dec. 2007; pp. 1776-1783; vol. 105, No. 6; International Anesthesia Research Society.
Hoffman, Hunter G.; "Virtual-Reality Therapy"; Scientific American Magazine; bearing a date of Jul. 26, 2004; pp. 60-65; located at http://www.sciam.com/article.cfm?id-000CDC34-D80E-10FA-89FB.
Hollifield, Michael, MD et al.; "Integrating Therapies for Anxiety Disorders"; Psychiatric Annals; May 2006; pp. 329-338; vol. 36, No. 5.
"Human Interface Technology Lab (HITL)"; Virtual Reality Pain Reduction; pp. 1-3; located at http://www.hitl.washington.edu-projects-vrpain/ ; printed on Apr. 18, 2008.
Huo, Xueliang et al.; "A Wireless Pharmaceutical Compliance Monitoring System Based on Magneto-Inductive Sensors"; Sensors Journal; IEEE; bearing a date of Dec. 2007; pp. 1711-1719; vol. 7, No. 12 [Abstract Only].
IEEE 100: The Authoritative Dictionary of IEEE Standards Terms, Seventh Edition; The Institute of Electrical and Electronics Engineering Press.

(56) References Cited

OTHER PUBLICATIONS

IEEE 100: The Authoritative Dictionary of IEEE Standards Terms, Seventh Edition; The Institute of Electrical and Electronics Engineering Press; Dec. 2000; 10 pages, as provided by Examiner; ISBN 0/7381-2601-2; The Institute of Electrical and Electronics Engineers, Inc.; New York, NY.

Jeanpierre, Laurent et al.; Automated Medical Diagnosis with Fuzzy Stochastic Models: Monitoring Chronic Diseases; Acta Biotheoretica; bearing a date of 2004; pp. 291-311; vol. 52, No. 4; Springer Publishing [Abstract Only].

Jokiniitty, J.M. et al.; "Prediction of Blood Pressure Level and Need for Antihypertensive Medication: 10 Years of Follow-up"; Journal of Hypertension; bearing a date of Jul. 2001; pp. 1193-1201; vol. 19, No. 7 [Abstract Only].

Knez, Igor; "Effects of Colour of Light on Nonvisual Psychological Processes"; bearing a date of Jun. 2001; pp. 201-208; vol. 21 No. 2; Journal of Environmental Psychology [Abstract Only].

Kozarek, R.A. et al.; "Prospective Trial Using Virtual Vision as Distraction Technique in Patients Undergoing Gastric Laboratory Procedures"; Gastroenterology Nursing; bearing a date of Jan. 1997; vol. 20, No. 1 [Abstract Only].

Kurtz, Matthew M., et al.; "A Virtual Reality Apartment as a Measure of Medication Management Skills in Patients with Schizophrenia: A Pilot Study"; Schizophrenia Bulletin; bearing a date of 2007; pp. 1162-1170; vol. 33; No. 5; Oxford University Press.

Kuzma, John M., Md et al.: "Integrating Pharmacotherapy and Psychotherapy in the Management of Anxiety Disorders"; Current Psychiatry Reports; 2004; pp. 268-273; vol. 6; Current Science Inc.

Lam, Raymond W. et al.; "The Can-SAD Study: A Randomized Controlled Trial of the Effectiveness of Ligh Therapy and Fluoxetine in Patents With Winter Seasonal Affective Disorder"; bearing a date of May 2006; pp. 805-812; vol. 163; American Journal of Psychiatry.

Lawrence, Dale A. et al.; "Human Perception of Friction in Haptic Interfaces"; Proc. Symposium on Haptic Interfaces for Virtual Environment and Teleoperator Systems; ASME Int'l Mech. Eng. Congress and Expo, Dynamic Systems and Control Division; bearing a date of Nov. 1998; pp. 287-294; vol. 64.

Lehrner et al.; "Ambient odors of orange and lavender reduce anxiety and improve mood in a dental office"; Physiology & Behavior; Apr. 27 2005; pp. 92-95; vol. 86; Elsevier Inc.

Marlier, Luc et al.; "Olfactory Stimulation Prevents Apnea in Premature Newborns"; Pediatrics; bearing a date of 2005; pp. 83-88; vol. 115, No. 1; American Academy of Pediatrics.

Matthews, D.E. et al.; "Using and Understanding Medical Statistics"; bearing a date of 2007; pp. 111-127; S. Karger AG Basel.

McClernon, F. Joseph et al.; "The Effects of Controlled Deep Breathing on Smoking Withdrawal Symptoms in Dependent Smokers"; ScienceDirect; bearing a date of Jun. 2004; pp. 765-772; vol. 29, No. 4; Elsevier Ltd. [Abstract Only].

McKendree-Smith et al.; "Self-Administered Treatments for Depression: A Review"; Journal of Clinical Psychology; bearing a date of Mar. 2003; pp. 275-288; vol. 59, No. 3; Wiley Periodicals, Inc.

Ming, Jin-Lain et al.; "The Efficacy of Acupressure to Prevent Nausea and Vomiting in Post-Operative Patients"; Journal of Advanced Nursing; bearing a date of Aug. 2002; pp. 343-351; vol. 39, No. 4; Blackwell Synergy [Abstract Only].

Morishita, S. et al.; "Induction of Mania in Depression by Paroxetine"; Human Psychopharmacol; bearing a date of Oct. 2003; pp. 565-568; vol. 18, No. 7; Dept. of Psychiatry, Kawasaki Medical School [Abstract Only].

Mueller et al.; "Noradrenergic modulation of extinction learning and exposure therapy"; Behavioural Brain Research; bearing a date of Dec. 1, 2009; pp. 1-11; vol. 208; Elsevier B.V.

Munjack, Dennis J. et al.; "Alprazolam, Propranolol, and Placebo in the Treatment of Panic Disorder and Agoraphobia with Panic Attacks"; Journal of Clinical Psychopharmacology; bearing a date of 1989; pp. 22-27; vol. 9, No. 1; Williams and Wilkins Co.

"New Horizons of Nerve Repair: Biomedical Engineer Trips Up Proteins in Nerve Regeneration System"; Science Daily; bearing a date of Jul. 26, 2002; pp. 1-2; located at http://www.sciencedaily.com/release/2002/07/020725082253.htm.

"New Mini-Sensor May Have Biomedical and Security Applications"; Physics/General Physics; bearing a date of Nov. 1, 2007; pp. 1-3; located at http://www.physorg.com/news113151078.html; Physorg.com.

"Northwest Regional Spinal Cord Injury System"; SCI Forum Report; pp. 1-5; located at http://sci.washington.edu-info-forums-reports-hypnosis_for_sci_pain.asp; printed on Apr. 18, 2008.

Pampallona et al; "Combined Pharmacotherapy and Psychological Treatment for Depression: A Systematic Review"; Arch Gen Psychiatry; bearing a date of Jul. 2004; pp. 714-719; vol. 61; American Medical Association.

Parker, G. et al.; "Prediction of Response to Antidepressant Medication by a Sign-Based Index of Melancholia"; Australian and New Zealand Journal of Psychiatry; bearing a date of 1993; pp. 56-61; vol. 27, No. 1 [Abstract Only].

Patolsky, Fernando et al.; "Nanowire Sensors for Medicine and the Life Sciences"; Future Medicine; bearing a date of Jun. 2006; pp. 51-65; vol. 1, No. 1 [Abstract Only].

Paul-Labrador, Maura, et al.; "Effects of Randomized Controlled Trial of Transcendental Meditation on Components of the Metabolic Syndrome in Subjects With Coronary Heart Disease"; Arch Intern Med; bearing a date of Jun. 12, 2006; pp. 1218-1224; vol. 166; American Medical Association.

"Phosphodiesterase Isoenzymes as Pharmacological Targets in the Treatment of Male Erectile Dysfunction"; World Journal of Urology; bearing a date of Feb. 2001; pp. 14-22; vol. 19, No. 1; Springer Berlin/Heidelberg [Abstract Only].

Piquepaille, Roland; "Virtual Reality Helps Diagnose Heart Defects"; bearing a date of Dec. 28, 2005; 2008 CNET Networks, Inc.

Prance, R.J. et al.; "Adaptive Electric Potential Sensors for Smart Signal Acquisition and Processing"; Journal of Physics: Conference Series 76; Sensors and their Applications XIV (SENSORS07); bearing a date of 2007; pp. 1-5; IOP Publishing Ltd.

Ressler, Kerry J. et al.; "Cognitive Enhancers as Adjuncts to Psychotherapy Use of D-Cycloserine in Phobic Individuals to Facilitate Extinction of Fear"; bearing a date of Nov. 2004; pp. 1136-1144; vol. 61; Arch Gen Psychiatry.

Rizzo, Albert et al.; "Virtual Therapeutic Environments with Haptics: An Interdisciplinary Approach for Developing Post-Stroke Rehabilitation Systems"; CPSN 2005; bearing a date of Jun. 20-23, 2005; pp. 70-76; Proceedings of the 2005 International Conference on Computers for People with Special Needs; University of Southern California.

Rothbaum, Barbara O. et al.; "Applying Learning Principles to the Treatment of Post-Trauma Reactions"; Annals New York Academy of Sciences; bearing a date of 2003; pp. 112-121; vol. 1008; New York Academy of Sciences.

Rothbaum et al.; "A Controlled Study of Virtual Reality Exposure Therapy for the Fear of Flying"; Journal of Consulting and Clinical Psychology; bearing a date of May 4, 2000; pp. 1020-1026; vol. 68, No. 6; American Psychological Association, Inc.

Sanfey, Alan G.; "Social Decision-Making: Insights from Game Theory and Neuroscience"; Science Magazine; bearing a date of Oct. 26, 2007; pp. 598-602; vol. 318, No. 5850.

Schellenberg, E. Glenn et al.; Exposure to Music and Cognitive Performance: Tests of Children and Adults; Psychology of Music; bearing a date of 2007; pp. 5-19; vol. 35 No. 1; Sage Publishing.

"Seromycin-cycloserine capsule"; Physician's Desk Reference Digital Drug Database; bearing a revision date of Jun. 2007; pp. 1-5; PDR Network, LLC.

Shaw, D. et al.; "Anxiolytic effects of lavender oil inhalation on open-field behaviour in rats"; Phytomedicine; bearing a date of Mar. 19, 2007; pp. 613-620; vol. 14; Elsevier Ltd.

Siedliecki, Sandra et al.; "Effect of Music on Power, Pain, Depression, and Disability"; Journal of Advanced Nursing; bearing a date of Jan. 13, 2006; pp. 553-562; vol. 54 No. 5; Blackwell Publishing.

Silva, Alcino J. et al.; "Creb and Memory"; Annu. Rev. Neurosci.; 1998; pp. 127-137 (as cited by Examiner); vol. 21; Annual Reviews Inc.

(56) References Cited

OTHER PUBLICATIONS

Skorin, Leonid JR., et al.; "How to Diagnose and Manage Headaches"; Review of Optometry; bearing a date of Nov. 1999; pp. 73-76; vol. 136.

Smith, M.R. et al.; "A data extrapolation algorithm using a complex domain neuralnetwork"; Circuits and Systems II: Analog and Digital Signal Processing; IEEE Transactions; bearing a date of Feb. 1997; pp. 143-147; vol. 44, No. 2 [Abstract Only].

"Something in the Way He Moves"; The Economist; bearing a date of Sep. 27, 2007; pp. 1-2; located at http://www.economist.com/science/PrinterFriendly.cfm? story_id=9861412.

Spencer, J.A.D. et al.; "White Noise and Sleep Induction"; Archives of Disease in Childhood; bearing a date of 1990; pp. 135-137; vol. 65; BMJ Publishing Group; published in London.

Staessen, Jan A. et al.; "Randomised Double-Blind Comparison of Placebo and Active Treatment for Older Patients With Isolated Systolic Hypertension"; The Lancet; bearing a date of Sep. 13, 1997; pp. 757-764; vol. 350, No. 9080 [Abstract Summary Only].

Sulaiman, S. et al.; "Human Motion Analysis Using Virtual Reality"; Research and Development, 2007; SCOReD 2007; 5th Student Conference; bearing a date of Dec. 11-12, 2007; pp. 1-4; IEEE; published in Selangor, Malaysia [Abstract Only].

Vaiva, Guillaume et al ; "Immediate Treatment with Propranolol Decreases Posttraumatic Stress Disorder Two Months after Trauma"; Biological Psychiatry; 2003; pp. 947-949; vol. 54; Society of Biological Psychiatry.

Van Gerwen et al.; "People Who Seek Help for Fear of Flying: Typology of Flying Phobics"; Behavior Therapy; bearing a date of Mar. 11, 1997; pp. 237-251; vol. 28; Association for Advancement of Behavior Therapy.

Vasterling, Jennifer et al.; "Cognitive Distraction and Relaxation Training for the Control of Side Effects Due to Cancer Chemotherapy"; Journal of Behavioral Medicine; bearing a date of Feb. 1993; pp. 65-80; vol. 16, No. 1; Springer Netherlands [Abstract Only].

"Video Game May Help Detect Depression"; New Scientist; bearing a date of Mar. 10, 2007; p. 18; No. 2594.

"Virtual Reality Medical Center"; p. 1; located at http://www.vrphobia.com/; printed on Apr. 23, 2008.

"Virtual Reality Games Used to Distract Young Burn Victims From Pain and Anxiety"; Medical News Today; bearing a date of Sep. 29, 2007; p. 1; located at http://www.medicalnewstoday.com/articles/84055.php.

"Virtual-Reality Video Game Helps Link Depression to Specific Brain Area"; ScienceDaily; bearing a date of Mar. 2, 2007; p. 1; located at http://www.sciencedaily.com/releases/2007/03/070301100807.htm; NIH (National Institute of Mental Health).

Von Muggenthaler, Elizabeth; "The Felid Purr: A Bio-Mechanical Healing Mechanism"; bearing a date of Sep. 18, 2006; 12th International Conference on Low Frequency Noise and Vibration and its Control; pp. 1-12; published in Bristol, UK.

Wiederhold, Brenda K.; "The Use of Virtual Reality Technology in the Treatment of Anxiety Disorders"; Information Technologies in Medicine; bearing a date of 2001; pp. 19-37; vol. II; John Wiley & Sons, Inc.

Yamada, K. et al.; "Prediction of Medication Noncompliance in Outpatients with Schizophrenia: 2-year follow-up study"; Psychiatry Research; bearing a date of 2004; pp. 61-69; vol. 141, No. 1; Elsevier Inc. [Abstract Only].

Yoshino, Kohzoh et al.; "An Algorithm for Detecting Startle State Based on Physiological Signals"; ScienceDirect; bearing a date of 2006; pp. 1-3; located at http://www.sciencedirect.com/science?_ob=ArticieURL&_udi=B6V5S-4M3BCCB-1&_user=10&_coverDate=03%2F31%2F2007&_alid=918001417&_rdoc=2&_fmt=high&_orig=search&_cdi=5794&_sort=d&_docanchor=&view=c&_ct=5&_acct=C000050221&_version=1&_urlVersion=0&_userid=10&md5=bc77a78ef5a694a6eef4dc397676f14f; Elsevier B.V. [Abstract Only].

Zhang, Kuan et al.; "Measurement of Human Daily Physical Activity"; Obesity Research; bearing a date of Jan. 1, 2003; pp. 33-40; vol. 11, No. 1; NASSO.

Chu et al.; "Proust nose best: Odors are better cues of autobiographical memory"; Memory & Cognition; bearing a date of Jan. 23, 2002; pp. 511-518; vol. 30, No. 4; Psychonomic Society, Inc.

Moss et al.; "Aromas of Rosemary and Lavender Essential Oils Differentially Affect Cognition and Mood in Healthy Adults", Intern. J. Neuroscience; bearing a date of Jul. 24, 2002; pp. 15-38; vol. 113; Taylor & Francis.

Gerardi et al.; "Virtual Reality Exposure Therapy Using a Virtual Iraq: Case Report"; Journal of Traumatic Stress; Apr. 2008; pp. 209-213; vol. 21, No. 2; 2008 International Society for Traumatic Stress Studies.

Cui et al.; "Nanowire Nanosensors for Highly Sensitive and Selective Detection of Biological and Chemical Species"; Science; Aug. 17, 2001; pp. 1289-1292; vol. 293; located at: www.sciencemag.org.

Lee et al.; "Reconsolidation and Extinction of Conditioned Fear: Inhibition and Potentiation"; The Journal of Neuroscience; Sep. 27, 2006; pp. 10051-10056; vol. 26, No. 39; Society for Neuroscience.

Myers et al.; "Mechanisms of fear extinction"; Molecular Psychiatry; Dec. 12, 2006; pp. 120-150; vol. 12; Nature Publishing Group.

Ressler et al.; "Targeting abnormal neural circuits in mood and anxiety disorders: from the laboratory to the clinic"; Nature Neuroscience; Sep. 2007; pp. 1116-1124; vol. 10, No. 9; Nature Publishing Group.

Schiller et al.; "Preventing the return of fear in humans using reconsolidation update mechanisms"; Nature; Jan. 7, 2010; pp. 49-54; vol. 463; Macmillan Publishers Limited.

Chen, Yang; "Olfactory display: development and application in virtual reality therapy"; Proceedings of the 16th International Conference on Artificial Reality and Telexistence—Workshops (ICAT 2006); Nov. 29-Dec. 2, 2006; pp. 1-5; IEEE Computer Society; IEEE Computer Society Press, Los Alamitos, CA.

Lee, Inn-Sook et al.; "Effects of Lavender Aromatherapy on Insomnia and Depression in Women College Students"; Journal of Korean Academy of Nursing; Feb. 2006; pp. 136-143; vol. 36, No. 1; Taehan Kanho Hakoe chi 36.

Ekman et al.; "What the Face Reveals: Basic and Applied Studies of Spontaneous Expression Using the Facial Action Coding System (FACS)"; 1997; pp. 1-7; Oxford University Press, Inc.

Pentland, Alex (Sandy); "Healthwear: Medical Technology Becomes Wearable"; Computer; May 2004; pp. 42-49; IEEE.

Tronson et al.; "Molecular Mechanisms of Memory Reconsolidation"; Nature Reviews Neuroscience; Apr. 2007; pp. 262-275; vol. 8; Nature Publishing Group.

\* cited by examiner

METHODS AND SYSTEMS FOR PRESENTING A COMBINATION TREATMENT

If an Application Data Sheet (ADS) has been filed on the filing date of this application, it is incorporated by reference herein. Any applications claimed on the ADS for priority under 35 U.S.C. 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC 119(e) for provisional patent applications, for any and all parent, grandparent, great-grandparent, etc. applications of the Priority Application(s)).

PRIORITY APPLICATIONS

The present application constitutes a continuation of U.S. patent application Ser. No. 12/315,366, entitled METHODS AND SYSTEMS FOR PRESENTING A COMBINATION TREATMENT, naming Roderick A. Hyde; Muriel Y. Ishikawa; Eric C. Leuthardt; Royce A. Levien; Robert W. Lord; Mark A. Malamud; Elizabeth A. Sweeney; Lowell L. Wood, Jr.; Victoria Y. H. Wood as inventors, filed Dec. 1, 2008, which is currently co-pending or is an application of which a currently co-pending application is entitled to the benefit of the filing date.

The present application constitutes a continuation-in-part of U.S. patent application Ser. No. 12/315,072, entitled METHODS AND SYSTEMS FOR PRESENTING A COMBINATION TREATMENT, naming Roderick A. Hyde; Muriel Y. Ishikawa; Eric C. Leuthardt; Royce A. Levien; Robert W. Lord; Mark A. Malamud; Elizabeth A. Sweeney; Lowell L. Wood, Jr.; Victoria Y. H. Wood as inventors, filed Nov. 26, 2008, which is currently co-pending or is an application of which a currently co-pending application is entitled to the benefit of the filing date.

If the listings of applications provided above are inconsistent with the listings provided via an ADS, it is the intent of the Applicant to claim priority to each application that appears in the Priority Applications section of the ADS and to each application that appears in the Related Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

For purposes of the USPTO extra-statutory requirements, the present application constitutes a continuation-in-part of United States Patent Application entitled COMBINATION TREATMENT SELECTION METHODS AND SYSTEMS, naming Roderick A. Hyde; Muriel V. Ishikawa; Eric C. Leuthardt; Royce A. Levier; Robert W. Lord; Mark A. Malamud; Elizabeth A. Sweeney; Lowell L. Wood, Jr.; and Victoria Y. H. Wood as inventors, filed Apr. 24, 2008, application Ser. No. 12/150,122, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 13, 2008, application Ser. No. 12/152,266, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 21, 2008, application Ser. No. 12/154,275, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed May 30, 2008, application Ser. No. 12/156,440, which is currently co-pending, or is an application of which a currently co-pending application is entitled to the benefit of the filing date.

For purposes of the USPTO extra-statutory requirements, the present application constitutes a continuation-in-part of United States Patent Application entitled SIDE EFFECT AMELIORATING COMBINATION THERAPEUTIC PRODUCTS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 5, 2008, application Ser. No. 12/156,949, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 6, 2008, application Ser. No. 12/157,160, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT SELECTION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 13, 2008, application Ser. No. 12/157,922, which is currently co-pending, or is an application of which a currently co pending application is entitled to the benefit of the filing date.

For purposes of the USPTO extra-statutory requirements, the present application constitutes a continuation-in-part of United States Patent Application entitled COMBINATION TREATMENT MODIFICATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 13, 2008, application Ser. No. 12/157,989, which is currently co-pending, or is an application of which a currently co-pending application is entitled to the benefit of the filing date.

For purposes of the USPTO extra-statutory requirements, the present application constitutes a continuation-in-part of United States Patent Application entitled COMBINATION TREATMENT ALTERATION METHODS AND SYSTEMS, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jun. 19, 2008, application Ser. No. 12/214,547, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 3, 2008, application Ser. No. 12/217,509, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 7, 2008, application Ser. No. 12/217,620, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 15, 2008, application Ser. No. 12/218,503, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 16, 2008, application Ser. No. 12/218,627, which is currently co-pending, or is an application of which a currently co-pending application is entitled to the benefit of the filing date.

For purposes of the USPTO extra-statutory requirements, the present application constitutes a continuation-in-part of United States Patent Application entitled SYSTEMS AND APPARATUS FOR MEASURING A BIOACTIVE AGENT EFFECT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Jul. 25, 2008, application Ser. No. 12/220,706, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MODIFYING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Aug. 22, 2008, application Ser. No. 12/229,531, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MODIFYING BIOACTIVE AGENT USE, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Aug. 25, 2008, application Ser. No. 12/229,612, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR DETECTING A BIOACTIVE AGENT EFFECT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 12, 2008, application Ser. No. 12/283,619, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR DETECTING A BIOACTIVE AGENT EFFECT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 15, 2008, application Ser. No. 12/283,742, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 30, 2008, application Ser. No. 12/286,751, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING AND MODIFYING A COMBINATION TREATMENT, naming RODERICK A, HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Sep. 30, 2008, application Ser. No. 12/286,730, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Oct. 10, 2008, application Ser. No. 12/287,686, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR MONITORING AND MODIFYING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Oct. 14, 2008, application Ser. No. 12/287,886, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Oct. 28, 2008, application Ser. No. 12/290,227, which is currently co-pending, or is an application of which a currently co-pending application is entitled to the benefit of the filing date.

For purposes of the USPTO extra-statutory requirements, the present application constitutes a continuation-in-part of United States Patent Application entitled METHODS AND SYSTEMS FOR PRESENTING A COMBINATION TREATMENT, naming RODERICK A. HYDE; MURIEL Y. ISHIKAWA; ERIC C. LEUTHARDT; ROYCE A. LEVIEN; ROBERT W. LORD; MARK A. MALAMUD; ELIZABETH A. SWEENEY; LOWELL L. WOOD, JR.; AND VICTORIA Y. H. WOOD as inventors, filed Oct. 29, 2008, application Ser. No. 12/290,456, which is currently co-pending, or is an application of which a currently co-pending application is entitled to the benefit of the filing date.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

TECHNICAL FIELD

This description relates to methods and systems for combining a bioactive agent with an artificial sensory experience.

SUMMARY

In one aspect, a method includes but is not limited to accepting an indication of a schedule for administration of a bioactive agent to an individual and presenting an indication of an artificial sensory experience at least partly based on the accepting an indication of the schedule for administration of the bioactive agent to the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a method includes but is not limited to accepting an indication of at least one of a pharmacokinetic or pharmacodynamic profile of a bioactive agent and an indication of a schedule for administration of the bioactive agent to an individual and presenting an indication of an artificial sensory experience at least partly based on the accepting an indication of the at least one of a pharmacokinetic or pharmacodynamic profile of the bioactive agent and the indication of the schedule for administration of the bioactive agent to the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a method includes but is not limited to accepting an indication of a bioactive agent administration for an individual, determining at least one of a pharmacokinetic or pharmacodynamic profile of the bioactive agent, and/or presenting an indication of an artificial sensory experience at least partly based on the accepting an indication of the at least one of a pharmacokinetic or pharmacodynamic profile of the bioactive agent and the indication of the schedule for administration of the bioactive agent to the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware is configured to effect the herein-referenced method aspects depending upon the design choices of the system designer.

In one aspect, a method includes but is not limited to accepting an indication of at least one bioactive agent and an indication of a schedule for administration of the bioactive agent to an individual and/or presenting an indication of an artificial sensory experience at least partly based on at least one of a pharmacokinetic profile or pharmacodynamic profile of the bioactive agent and the indication of the schedule for administration of the bioactive agent to the individual. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to means for accepting an indication of a schedule for administration of a bioactive agent to an individual and means for presenting an indication of an artificial sensory experience at least partly based on the accepting an indication of the schedule for administration of the bioactive agent to the individual. In addition to the foregoing, other method aspects are described in the claims, drawings, and text forming a part of the present disclosure.

In one aspect, a system includes but is not limited to means for accepting an indication of at least one of a pharmacokinetic or pharmacodynamic profile of a bioactive agent and an indication of a schedule for administration of the bioactive agent to an individual and means for presenting an indication of an artificial sensory experience at least partly based on the accepting an indication of the at least one of a pharmacokinetic or pharmacodynamic profile of the bioactive agent and the indication of the schedule for administration of the bioactive agent to the individual. In addition to the foregoing, other method aspects are described in the claims, drawings, and text forming a part of the present disclosure.

In one aspect, a system includes but is not limited to means for accepting an indication of a bioactive agent administration for an individual, means for determining at least one of a pharmacokinetic or pharmacodynamic profile of the bioactive agent, and/or means for presenting an indication of an artificial sensory experience at least partly based on the accepting an indication of the at least one of a pharmacokinetic or pharmacodynamic profile of the bioactive agent and the indication of the schedule for administration of the bioactive agent to the individual. In addition to the foregoing, other method aspects are described in the claims, drawings, and text forming a part of the present disclosure.

In one aspect, a system includes but is not limited to means for accepting an indication of at least one bioactive agent and an indication of a schedule for administration of the bioactive agent to an individual and means for presenting an indication of an artificial sensory experience at least partly based on at least one of a pharmacokinetic profile or pharmacodynamic profile of the bioactive agent and the indication of the schedule for administration of the bioactive agent to the individual. In addition to the foregoing, other method aspects are described in the claims, drawings, and text forming a part of the present disclosure.

In one aspect, a system includes but is not limited to circuitry for accepting an indication of a schedule for administration of a bioactive agent to an individual and circuitry for presenting an indication of an artificial sensory experience at least partly based on the accepting an indication of the schedule for administration of the bioactive agent to the individual. In addition to the foregoing, other method aspects are described in the claims, drawings, and text forming a part of the present disclosure.

In one aspect, a computer program product includes but is not limited to a signal-bearing medium bearing one or more instructions for accepting an indication of a schedule for administration of a bioactive agent to an individual, and one or more instructions for presenting an indication of an artificial sensory experience at least partly based on the accepting an indication of the schedule for administration of the bioactive agent to the individual. In addition to the foregoing, other method aspects are described in the claims, drawings, and text forming a part of the present disclosure.

In one aspect, a system includes but is not limited to a computing device and instructions that when executed on the computing device cause the computing device to accept an indication of a schedule for administration of a bioactive agent to an individual and present an indication of an artificial sensory experience at least partly based on the accepting an indication of the schedule for administration of the bioactive agent to the individual. In addition to the foregoing, other method aspects are described in the claims, drawings, and text forming a part of the present disclosure.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

DETAILED DESCRIPTION

Figure 1:
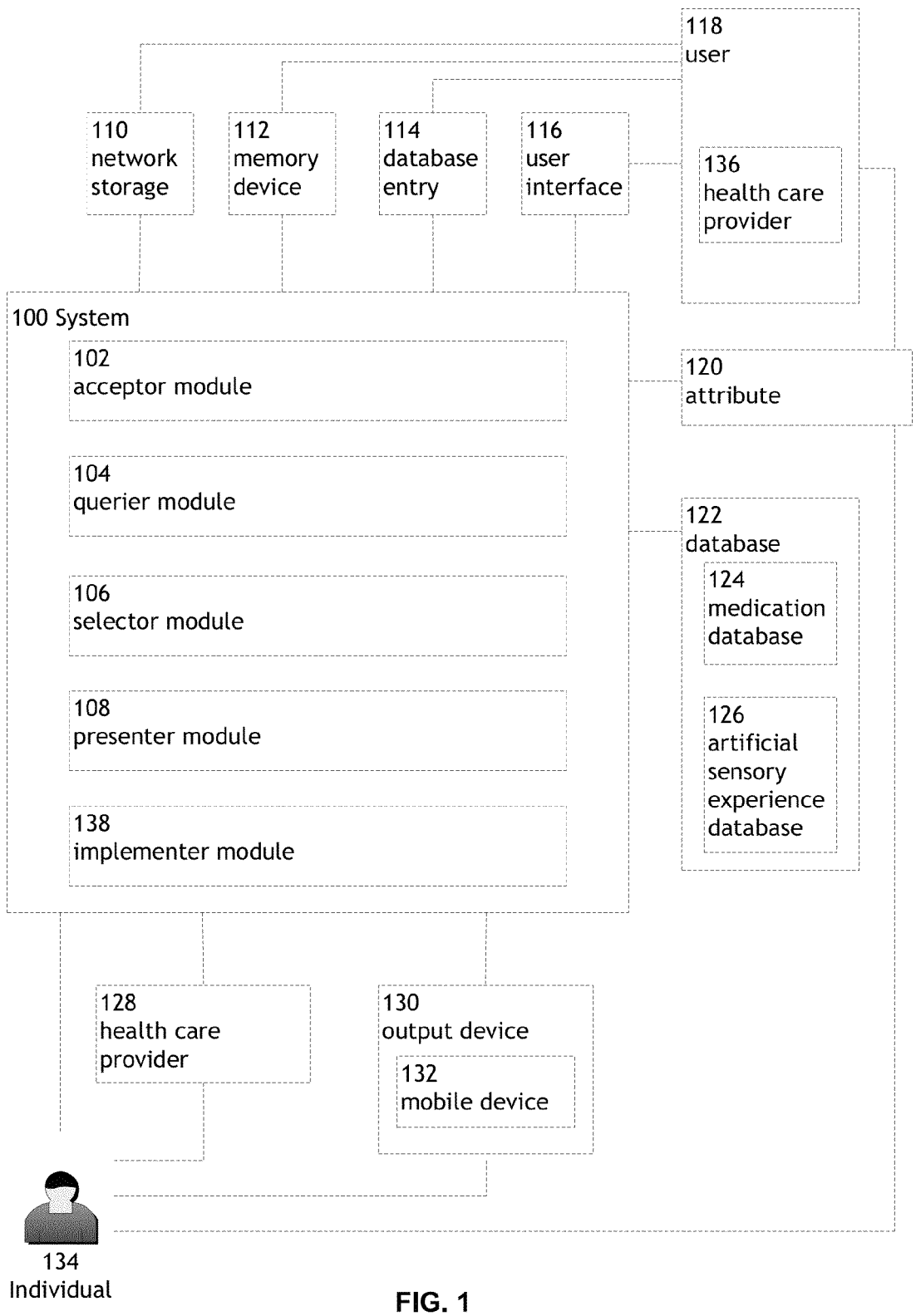
FIG. 1 illustrates an exemplary environment in which one or more technologies may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates a system 100 for accepting at Least one attribute of at least one individual, querying at least one database at least partly based on the at Least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The system 100 may include acceptor module 102, querier module 104, selector module 106, presenter module 108, implementer module 138, and/or modifier module 140. Acceptor module 102 may receive attribute 120 from network storage 110, memory device 112, database entry 114, and/or user interface 116. User interface 116 may receive information from user 118. User 118 may include health care provider 136. Querier module 104 may search database 122. Database 122 may include medication database 124 and/or artificial sensory experience database 126. Presenter module 108 may present to health care provider 128, output device 130, and/or individual 134. Output device 130 may include mobile device 132. Modifier module 140 may include restrictor module 142, granter module 144, alterer module 146, adder module 148, deleter module 150, and/or acceptor module 152. System 100 generally represents instrumentality for accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual. The operations of accepting at least one attribute of at least one individual, querying at least one database at least partly based on the at least one attribute, selecting from the at least one database at least one prescription medication and at least one artificial sensory experience to address the at least one attribute of at least one individual, and presenting an indication of the at least one prescription medication and the at least one artificial sensory experience at least partly based on the selecting from the at least one database at least one prescription medication and at least one artificial sensory experience to address the at least one attribute of at least one individual may be accomplished electronically, such as with a set of interconnected electrical components, an integrated circuit, and/or a computer processor.

Figure 2:
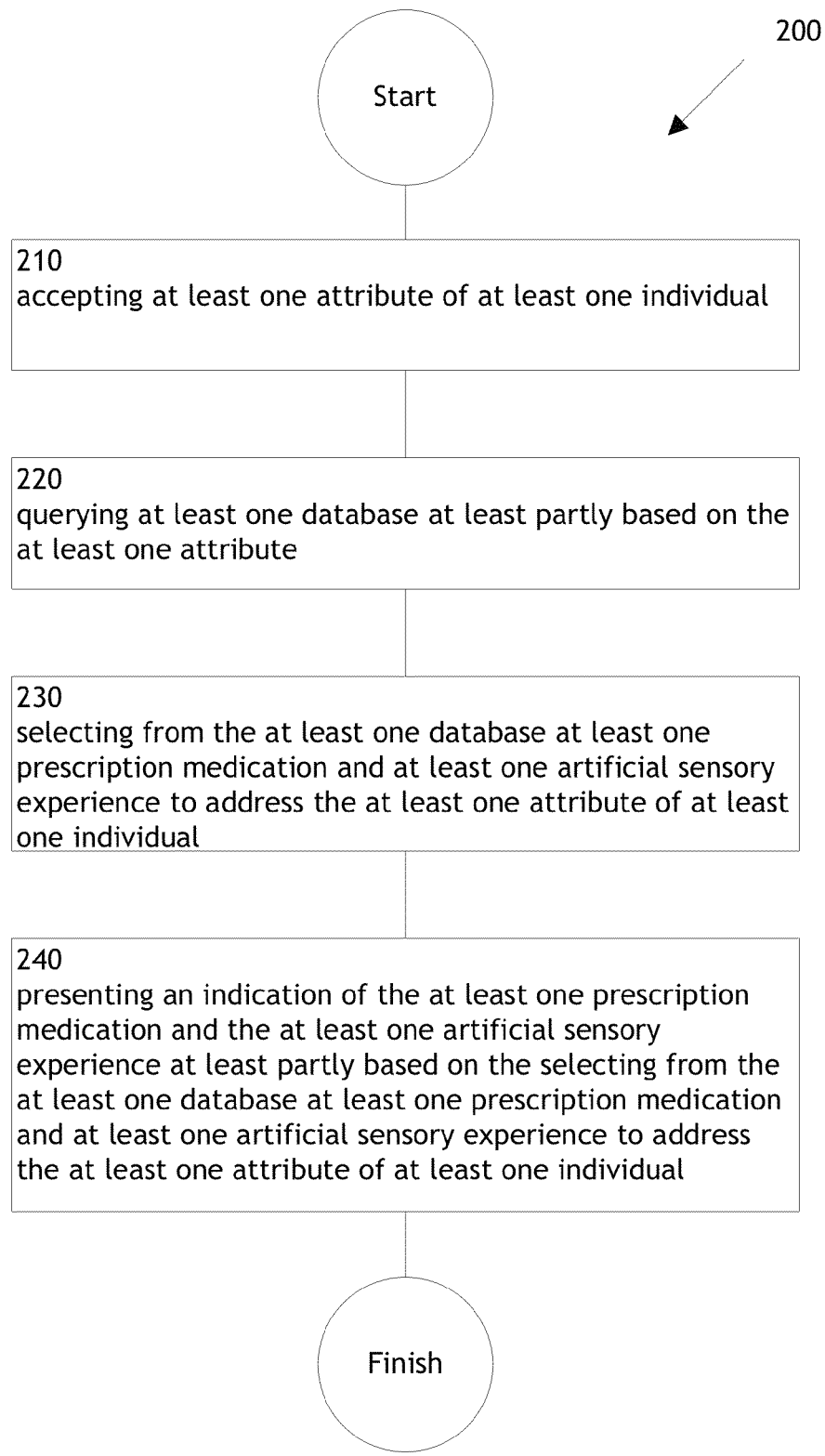
FIG. 2 illustrates an operational flow representing example operations related to selecting a combination of at least one prescription medication and at least one artificial sensory experience.

FIG. 2 illustrates an operational flow 200 representing example operations related to accepting at least one attribute of at least one individual, querying at least one database at least partly based on the at least one attribute, selecting from the at least one database at least one prescription medication and at least one artificial sensory experience to address the at least one attribute of at least one individual, and/or presenting an indication of the at Least one prescription medication and the at least one artificial sensory experience at (east partly based on the selecting from the at least one database at least one prescription medication and at least one artificial sensory experience to address the at least one attribute of at least one individual. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to an operation 210. Operation 210 depicts accepting at least one attribute of at least one individual. For example, as shown in FIG. 1, acceptor module 102 may accept at least one attribute of at least one individual. In one instance, acceptor module 102 can accept from a user 118 and a user interface 116 an attribute 120 including an attribute of a personal health history associated with an individual named John Smith. In some instances, acceptor module 102 may include a computer processor.

Then, operation 220 depicts querying at Least one database at least partly based on the at least one attribute. For example, as shown in FIG. 1, querier module 104 may search at least one database at least partly based on the at least one attribute. In one example and continuing with the previous example, querier module 104 can search a database 122 including a medication database 124 and artificial sensory experience database 126 at least partly based on the attribute including an attribute of a personal health history associated with an individual named John Smith. In some instances, querier module 104 may include a computer processor.

Then, operation 230 depicts selecting from the at least one database at least one prescription medication and at least one artificial sensory experience to address the at least one attribute of at least one individual. For example, as shown in FIG. 1, selector module 106 may select from the at least one database at least one prescription medication and at least one artificial sensory experience to address the at least one attribute of at Least one individual. In one instance and continuing with the previous example, selector module 106 can select from a medication database 124 and artificial sensory experience database 126 a prescription medication and an artificial sensory experience for addressing the attribute 120 including an attribute of a personal health history associated with an individual named John Smith. In some instances, selector module 106 may include a computer processor.

Then, operation 240 depicts presenting an indication of the at least one prescription medication and the at least one artificial sensory experience at least partly based on the selecting from the at least one database at least one prescription medication and at Least one artificial sensory experience to address the at least one attribute of at least one individual. For example, as shown in FIG. 1, presenter module 108 may present the at Least one prescription medication and the at least one artificial sensory experience at least partly based on the searching at least one database at least partly based on the at least one attribute. In one instance and continuing with the previous example, presenter module 108 can present to a medical professional the prescription medication and the artificial sensory experience based on searching the medication database 124 and artificial sensory experience database 126 based on the at least one attribute 120 including an attribute of a personal health history associated with an individual named John Smith. In some instances, presenter module 108 may include a computer processor.

Figure 3:
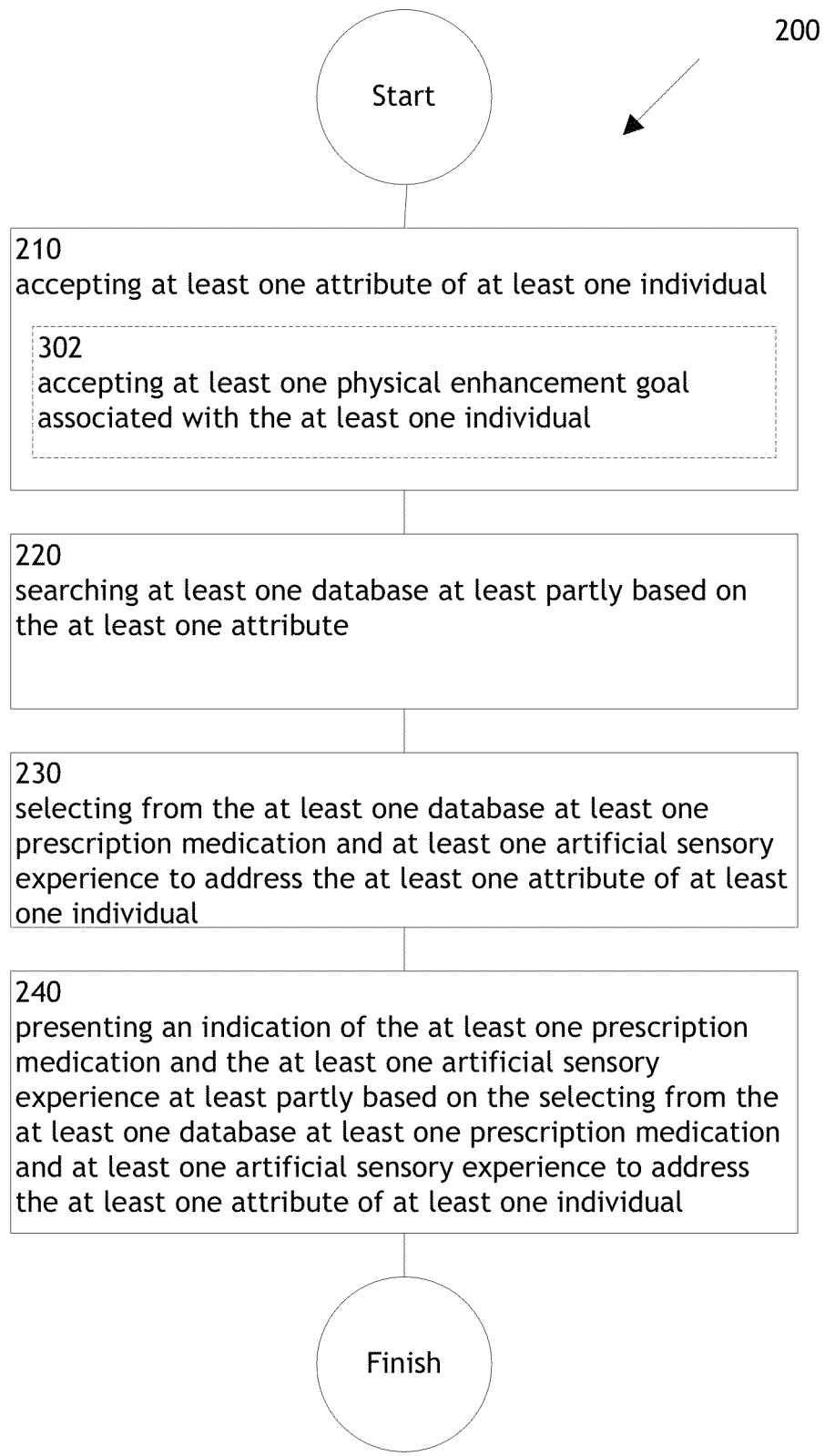
FIG. 3 illustrates an alternative embodiment of the operational flow of FIG. 2.

FIG. 3 illustrates alternative embodiments of the example operational flow 200 of FIG. 2. FIG. 3 illustrates example embodiments where the operation 210 may include at least one additional operation. Additional operations may include an operation 302.

Operation 302 illustrates accepting at least one physical enhancement goal associated with the at least one individual. For example, as shown in FIG. 1, acceptor module 102 may accept from a database entry 114 at least one physical enhancement goat associated with the at least one individual. In one instance and continuing with the above example, acceptor module 102 accepts from memory device 112 at least one physical enhancement goal associated with an individual named John Smith. A physical enhancement goal may include a physical state and/or situation an individual may plan to achieve. Some examples of a physical enhancement goal may include achieving a certain state of relaxation, reaching a certain body mass, maintaining a specific cholesterol level, achieving an athletic performance goal, and/or lowering a blood pressure level. In some instances, acceptor module 102 may include a computer processor.

Figure 4:
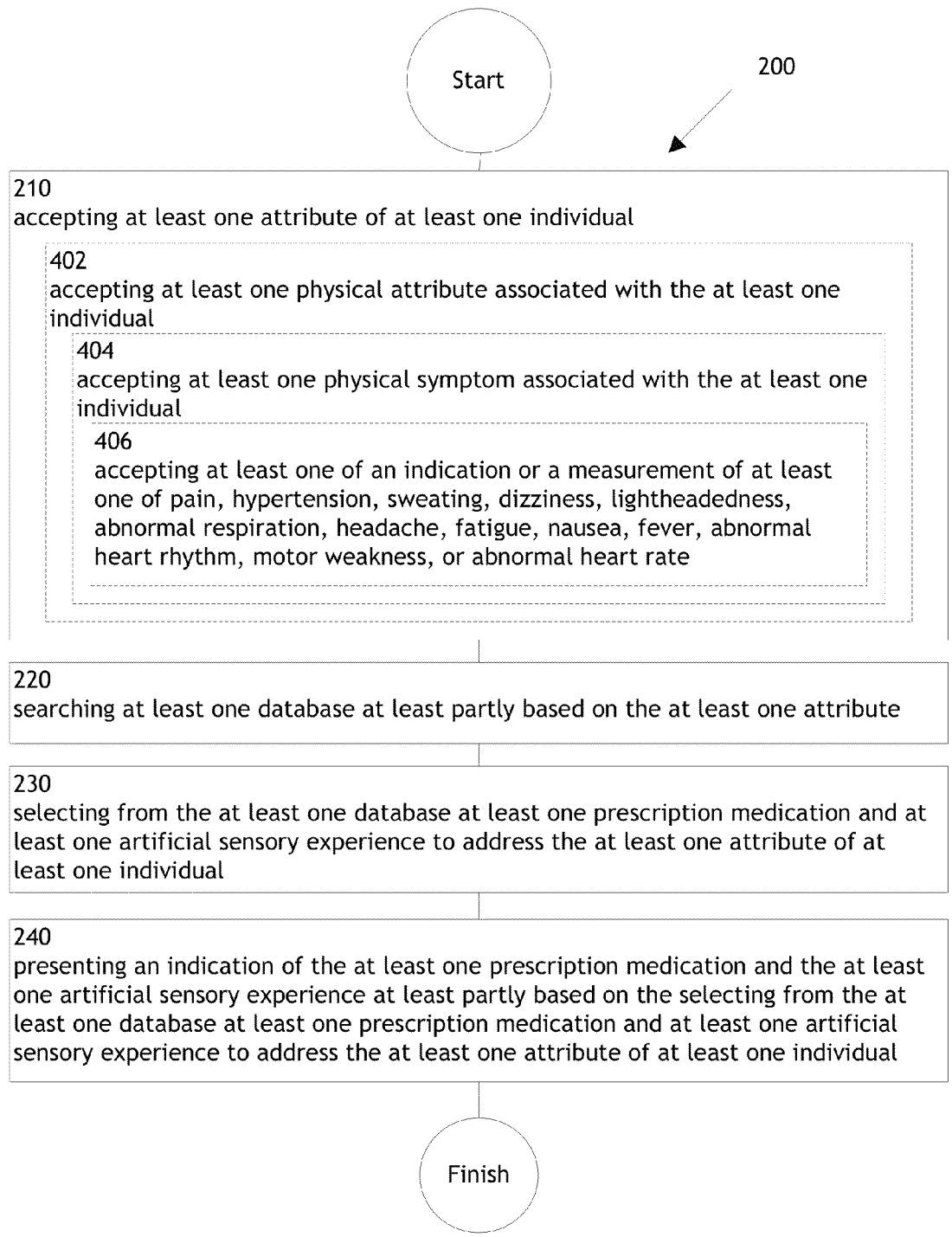
FIG. 4 illustrates an alternative embodiment of the operational flow of FIG. 2.

FIG. 4 illustrates alternative embodiments of the example operational flow 200 of FIG. 2. FIG. 4 illustrates example embodiments where the operation 210 may include at Least one additional operation. Additional operations may include an operation 402, an operation 404, and/or an operation 406.

Operation 402 illustrates accepting at Least one physical attribute associated with the at least one individual. For example, as shown in FIG. 1, acceptor module 102 may accept from network storage 110 at least one physical attribute associated with the at least one individual. In one instance, acceptor module 102 can accept a physical attribute 120 associated with a group of twenty individuals including an individual weight for each individual. A physical attribute may include an attribute that may be described and/or detected using senses, that has substance and/or a material existence, and/or that may be acted upon by physical force. Some examples of a physical attribute may include a biochemical measurement such as blood sugar Level, a smell, an appearance, a physiological measurement such as blood pressure, and/or skin conductivity. In some instances, acceptor module 102 may include a computer processor.

Operation 404 illustrates accepting at least one physical symptom associated with the at least one individual. For example, as shown in FIG. 1, acceptor module 102 may accept at least one physical symptom associated with the at least one individual. In one example, acceptor module 102 can accept from a user 118 and/or user interface 116 a physical symptom including an indication of influenza such as a fever associated with an individual named Mark White. A physical symptom may include a manifestation, sign, and/or an indication of the presence of a disease and/or some other bodily disorder and/or abnormality. Some examples of a physical symptom may include pain, swelling, fever, rash, and/or discoloration. In some instances, acceptor module 102 may include a computer processor.

Operation 406 illustrates accepting at Least one of an indication or a measurement of at least one of pain, hypertension, sweating, dizziness, lightheadedness, abnormal respiration, headache, fatigue, nausea, fever, abnormal heart rhythm, motor weakness, or abnormal heart rate. For example, as shown in FIG. 1, acceptor module 102 may accept from at least one of an indication or a measurement of at Least one of pain, high blood pressure, sweating, dizziness, lightheadedness, abnormal respiration, headache, fatigue, nausea, fever, abnormal heart rhythm, motor weakness, or abnormal heart rate. In one example, acceptor module 102 can accept an indication of pain and a measurement of high blood pressure from network storage 110. Pain may include a sensation of somatic hurt or disorder and may include acute pain and/or chronic pain. Hypertension may include chronically elevated blood pressure and may be considered to be present when a person's systolic blood pressure is consistently about 140 mm Hg or greater and/or their diastolic blood pressure is consistently about 90 mm Hg or greater. Sweating may include the excessive production and/or evaporation of fluid excreted by the sweat glands in the skin. Dizziness may include vertigo, disequilibrium, pre-syncope, and/or other balance disorders. Lightheadedness may include a sensation of dizziness and/or fainting. Abnormal respiration may include atypical and/or pathological breathing patterns. Headache may include pain in the head, neck, and/or upper back and may be a symptom of tension, migraine, dehydration, eye strain, sinus disorders, and/or low blood sugar. Fatigue may include muscle weakness and/or lack of strength. Nausea may include the sensation of unease and/or discomfort in the stomach, often with the urge to vomit. Fever may include an increase in internal body temperature to levels above normal. Abnormal heart rhythm may include inconsistent and/or irregular rhythmic contractions in the heart such as sick sinus syndrome, atrial fibrillation, and/or atrial flutter. Motor weakness may include a lack of strength and/or function in the portion of the central nervous system involved in movement. An abnormal heart rate may include an irregular heart contraction frequency such as bradycardia, tachycardia or the like. In some instances, acceptor module 102 may include a computer processor.

Figure 5:
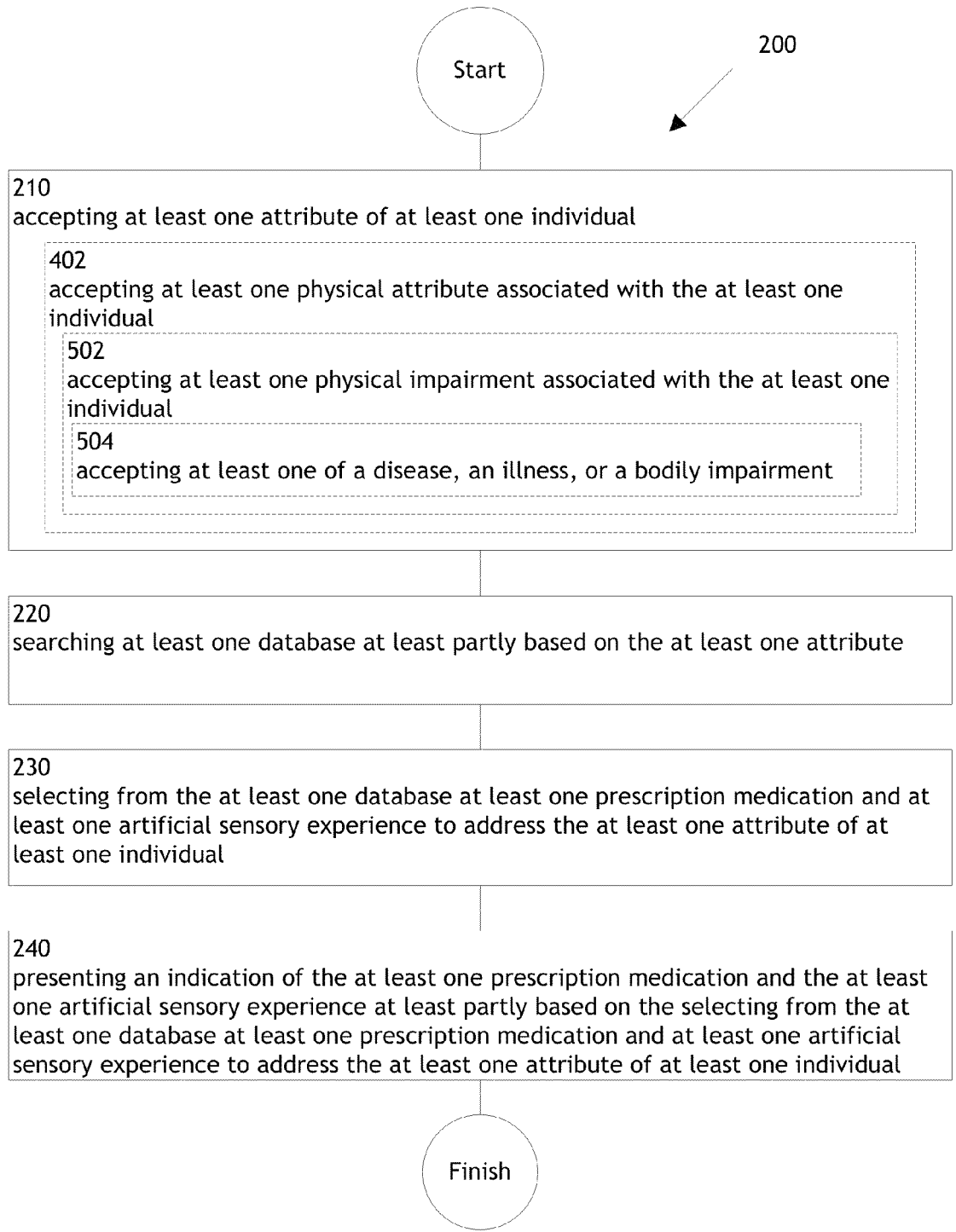
FIG. 5 illustrates an alternative embodiment of the operational flow of FIG. 2.

FIG. 5 illustrates alternative embodiments of the example operational flow 200 of FIG. 2. FIG. 5 illustrates example embodiments where the operation 210 may include at least one additional operation. Additional operations may include an operation 502, and/or an operation 504. Further, operation 502 illustrates accepting at least one physical impairment associated with the at least one individual. For example, as shown in FIG. 1, acceptor module 102 may accept at least one physical impairment associated with the at least one individual from a user 118 and a user interface 116. In one instance, acceptor module 102 accepts a physical impairment including a bodily impairment associated with an individual named Fred Johnson from a user 118 and/or a user interface 116. A physical impairment may include a condition or function judged to be significantly impaired relative to the usual standard of an individual of their group and may include physical impairment, sensory impairment, and/or disease. In some instances, acceptor module 102 may include a computer processor.

Operation 504 illustrates accepting at Least one of a disease, an illness, or a bodily impairment. For example, as shown in FIG. 1, acceptor module 102 may accept at least one of a disease, an illness, or a bodily impairment. In one example, acceptor module 102 accepts an indication of a disease and a bodily impairment from database entry 114. A disease may include an abnormal condition of an organism that impairs bodily functions associated with one or more specific symptoms and signs and may include discomfort, distress, dysfunction, injury, a disorder, a syndrome, infection, and/or other atypical variation associated with structure and/or function of the body. An illness may include any state of poor health. Some examples of an illness may include cancer, the common cold, influenza, pneumonia, and/or high cholesterol. A bodily impairment may include a diminished ability in body function and/or structure. In some instances, acceptor module 102 may include a computer processor.

Figure 6:
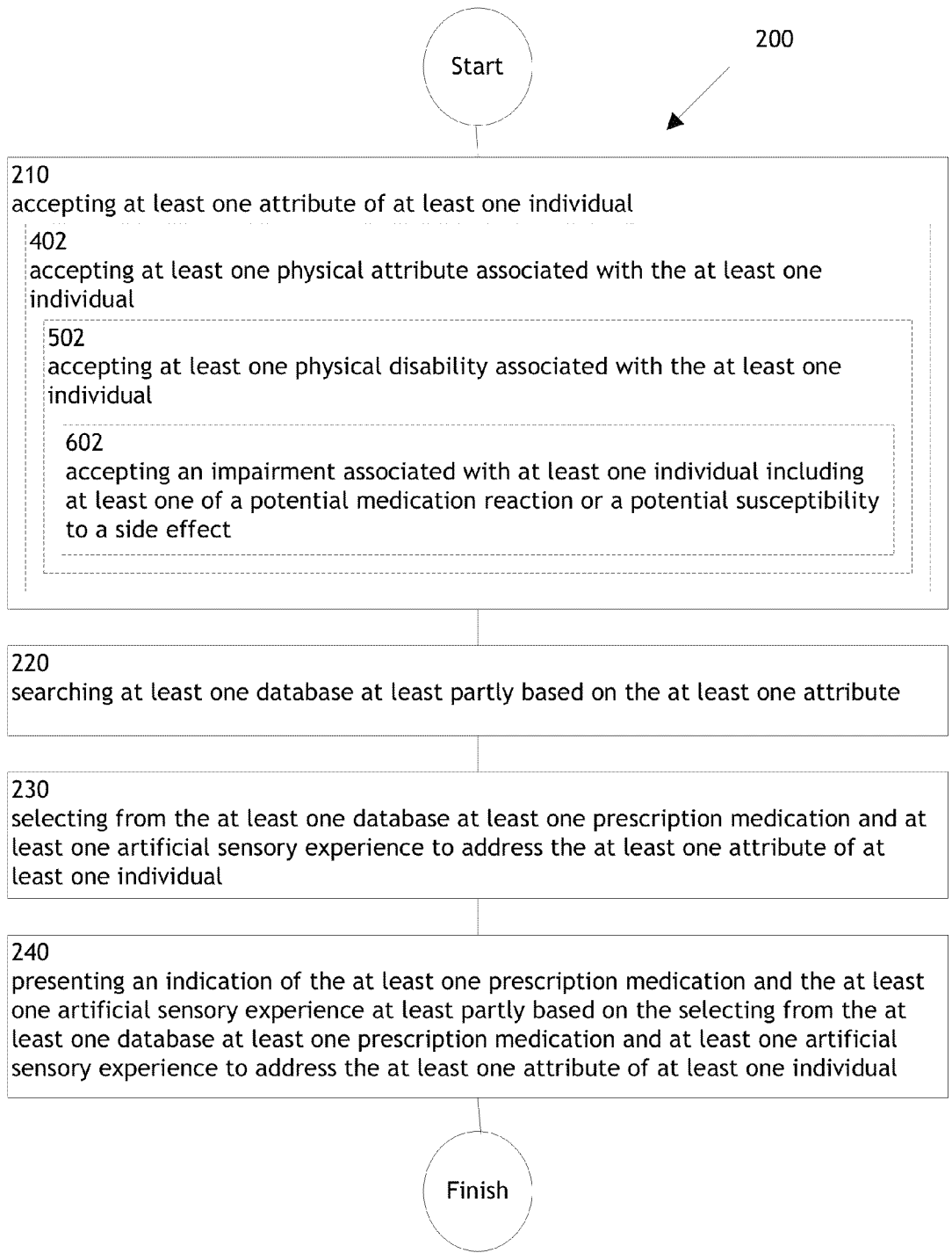
FIG. 6 illustrates an alternative embodiment of the operational flow of FIG. 2.

FIG. 6 illustrates alternative embodiments of the example operational flow 200 of FIG. 2. FIG. 6 illustrates example embodiments where operation 210 may include at least one additional operation. Additional operations may include an operation 602. Operation 602 illustrates accepting an impairment associated with at Least one individual including at Least one of a potential medication reaction or a potential susceptibility to a side effect. For example, as shown in FIG. 1, acceptor module 102 may accept an impairment associated with at least one individual including at least one of a potential medication reaction or a potential susceptibility to a side effect. In one example, acceptor module 102 can accept from network storage 110 an impairment associated with at least one individual including at least one of a potential medication reaction or a potential susceptibility to a side effect. A potential medication reaction may include a possible response a person may exhibit resulting from at Least one drug and/or medication administered to the person. A potential medication reaction may include an allergy and/or a drug and/or medication interaction with a separate drug and/or medication. A potential susceptibility to a side effect may include the probability a certain person may be vulnerable to a side effect coupled with a specific drug and/or medication. In some instances, acceptor module 102 may include a computer processor.

Figure 7:
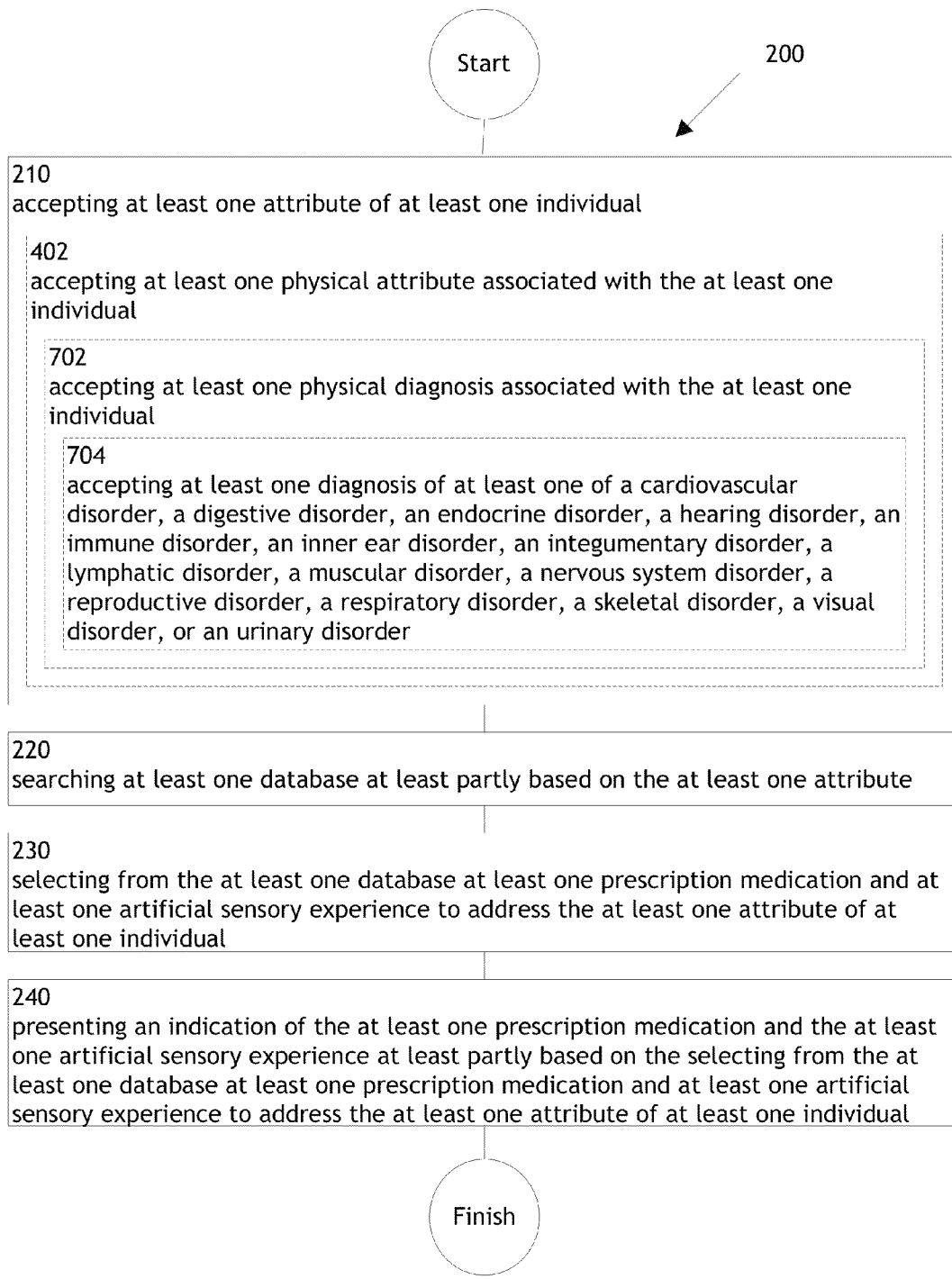
FIG. 7 illustrates an alternative embodiment of the operational flow of FIG. 2.

FIG. 7 illustrates alternative embodiments of the example operational flow 200 of FIG. 2. FIG. 7 illustrates example embodiments where the operation 210 may include at least one additional operation. Additional operations may include an operation 702, and/or an operation 704. Further, operation 702 illustrates accepting at least one physical diagnosis associated with the at least one individual. For example, as shown in FIG. 1, acceptor module 102 may accept at least one physical diagnosis associated with the at least one individual. In a specific example, acceptor module 102 accepts from memory device 112 a physical diagnosis associated with a group of ten individuals. A physical diagnosis may include identifying a disease and/or condition by its outward signs and/or symptoms. Some examples of a physical diagnosis may include identifying influenza and/or identifying Alzheimer's disease. In some instances, acceptor module 102 may include a computer processor.

Operation 704 illustrates accepting at least one diagnosis of at least one of a cardiovascular disorder, a digestive disorder, an endocrine disorder, a hearing disorder, an immune disorder, an inner ear disorder, an integumentary disorder, a lymphatic disorder, a muscular disorder, a nervous system disorder, a reproductive disorder, a respiratory disorder, a skeletal disorder, a visual disorder, or an urinary disorder. For example, as shown in FIG. 1, acceptor module 102 may accept at least one diagnosis of at least one of a cardiovascular disorder, a digestive disorder, an endocrine disorder, an integumentary disorder, a Lymphatic disorder, a muscular disorder, a nervous system disorder, a reproductive disorder, a respiratory disorder, a skeletal disorder, or an urinary disorder. In a specific instance, acceptor module 102 can accept from user interface 116 and/or user 118 a diagnosis of a respiratory disorder. A cardiovascular disorder may include a disorder associated with the circulatory system including the pumping and channeling of blood to and from the body and lungs with the heart, the blood, and the blood vessels. Examples of a circulatory disorder include high blood pressure, coronary heart disease, atherosclerosis, or the Like. A digestive disorder may include a disorder associated with the esophagus, the stomach, the liver, the gallbladder, the pancreas, the intestines, the rectum, the anus, and/or the digestive system including digestion and processing food with salivary glands. Examples of a digestive disorder include GERD, Crohn's disease, IBS, stomach ulcers including those associated with H. pylori infection, or the like. An endocrine disorder may include a disorder associated with the endocrine system including the pancreas, the pituitary gland, the pineal body and/or the pineal gland, the thyroid, the parathyroids, the adrenal glands, and/or communication within the body using hormones made by the endocrine glands, such as the hypothalamus. Examples of an endocrine disorder include diabetes, acromegaly, or the like. A hearing disorder may include a full or partial decrease in the ability to detect or understand sounds. Some examples of a hearing disorder may include otosclerosis, deafness, loss due to death of auditory hair cells, for example that caused by trauma, and/or unilateral hearing loss. An immune disorder may include a dysfunction of the immune system. Examples of an immune disorder may include an immunodeficiency, such as malfunctioning lymphocytes; autoimmunity, such as Coeliac disease and/or autoimmune hepatitis; and/or hypersensitivity, such as asthma. An inner ear disorder may include a balance disorder, such as vertigo, disequilibrium, and/or pre-syncope. An integumentary disorder may include a disorder associated with the integumentary system including the skin, hair, and/or nails, such as psoriasis, eczema, dermatitis, or the like. A lymphatic disorder may include a disorder associated with the lymphatic system including structures involved in the transfer of lymph between tissues and the blood stream and/or the lymph and the nodes and vessels that transport lymph including the immune system, including defending against disease-causing agents with leukocytes, and/or including the tonsils, the adenoids, the thymus, and/or the spleen. Examples of a Lymphatic disorder include lymphedema, lymphadenopathy, or the like. A muscle disorder may include a disorder associated with the muscular system including the structure and/or movement of muscles. Examples of a muscle disorder include muscular dystrophy, myasthenia gravis, an injury, such as a strain, or the like. A nervous system disorder may include a disorder associated with the nervous system including collecting, transferring, and/or processing information with the brain, the spinal cord, the peripheral nerves, and/or the nerves. Examples of a nervous system disorder include multiple sclerosis, fibromyalgia, carpal tunnel syndrome, or the like. A reproductive disorder may include a disorder associated with the reproductive system including the sex organs, such as ovaries, fallopian tubes, the uterus, the vagina, mammary glands, testes, the vas deferens, seminal vesicles, the prostate, and/or the penis. Examples of a reproductive disorder include erectile dysfunction, endometriosis, fibroids, or the like. A respiratory disorder may include a disorder associated with the respiratory system including the organs used for breathing, the pharynx, the larynx, the trachea, the bronchi, the lungs, and/or the diaphragm. Examples of a respiratory disorder include emphysema, asthma, or the like. A skeletal disorder may include a disorder associated with the skeletal system including the structural support and protection with bones, cartilage, ligaments, and/or tendons. Examples of a skeletal disorder include osteoporosis, arthritis, tendonitis, a skeletal injury, such as a bone fracture, or the like. A visual disorder may include a disease, impairment, and/or tack of function in the eye and/or in visual perception. Some examples of a visual disorder may include amblyopia, macular degeneration, glaucoma, and/or blindness. A urinary disorder may include a disorder associated with the urinary system including the kidneys, the ureters, the bladder and/or urethra involved in fluid balance, electrolyte balance and/or the excretion of urine. Examples of a urinary disorder include bladder dysfunction, kidney disease, bladder or urethra infection, or the like. In some instances, acceptor module 102 may include a computer processor.

Figure 8:
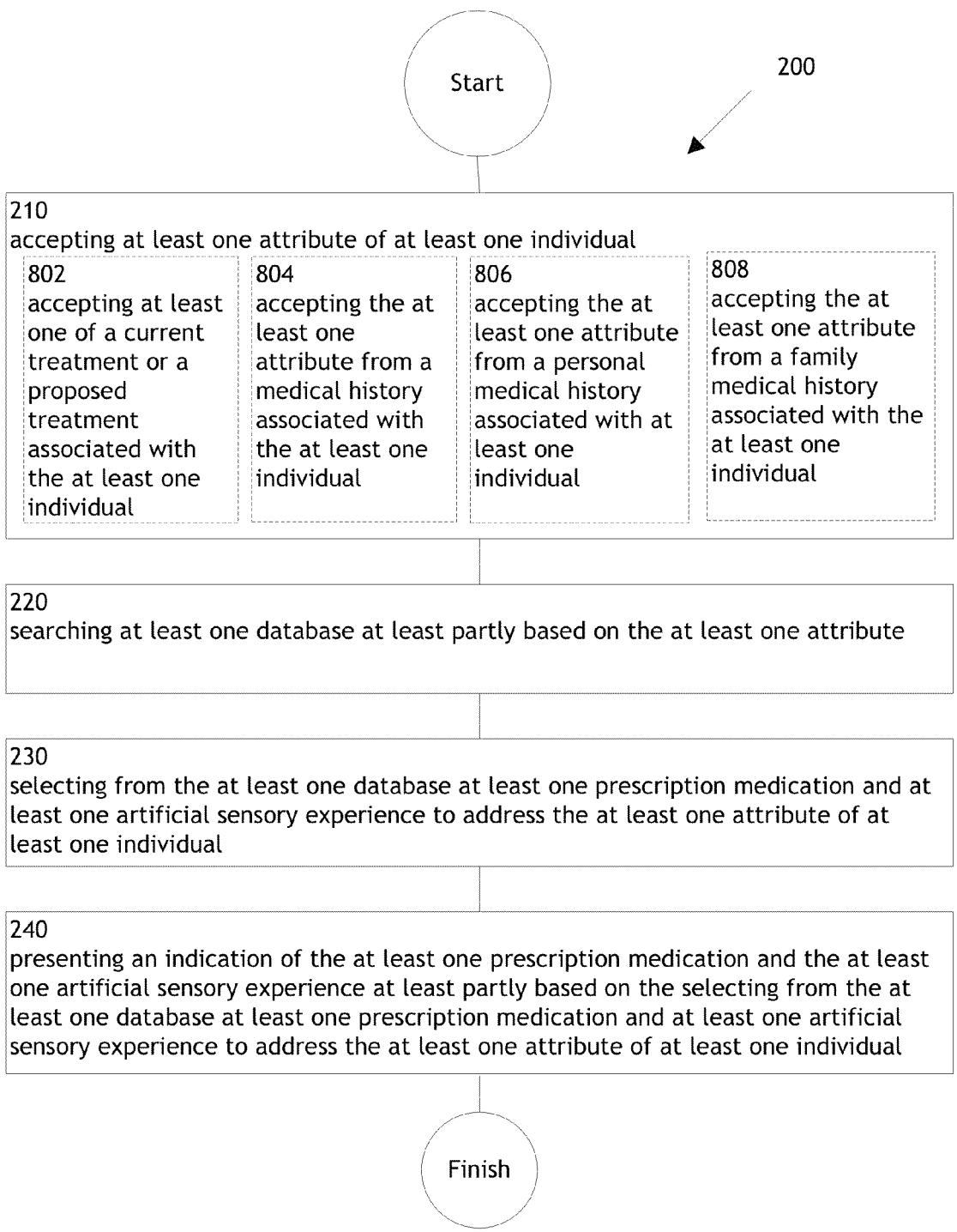
FIG. 8 illustrates an alternative embodiment of the operational flow of FIG. 2.

FIG. 8 illustrates alternative embodiments of the example operational flow 200 of FIG. 2. FIG. 8 illustrates example embodiments where the operation 210 may include at least one additional operation. Additional operations may include an operation 802, an operation 804, an operation 806, and/or operation 808.

Operation 802 illustrates accepting at Least one of a current treatment or a proposed treatment associated with the at least one individual. For example, as shown in FIG. 1, acceptor module 102 may accept at least one of a current treatment or a proposed treatment associated with the at least one individual. In one instance, acceptor module 102 accepts a current treatment regime associated with an individual named Cathy Hansen. A current treatment may include one or a series of treatments recommended, administered, and/or prescribed for a certain individual. A proposed treatment may include one or a series of treatments recommended, prescribed, and/or not currently administered to a certain individual. In some instances, acceptor module 102 may include a computer processor.

Operation 804 illustrates accepting the at least one attribute from a medical history associated with the at least one individual. For example, as shown in FIG. 1, acceptor module 102 may accept the at least one attribute from a medical history associated with the at least one individual. In one example, acceptor module 102 may accept from database entry 114 an attribute 120 from a medical history including the number of blood relatives with diabetes associated with an individual named Emily Smith. A medical history may include a list of previous illnesses, symptoms, medicines, treatments, health risk factors, operations, and/or doctor visits for an individual and/or a relation of an individual. In some instances, acceptor module 102 may include a computer processor.

Operation 806 illustrates accepting the at least one attribute from a personal medical history associated with at least one individual. For example, as shown in FIG. 1, acceptor module 102 may accept the at Least one attribute from a personal medical history associated with at least one individual. In a specific instance, acceptor module 102 can accept from database entry 114 an attribute 120 including, for example, a list of operations from a personal medical history associated with an individual named Robert Murphy. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In some instances, acceptor module 102 may include a computer processor.

Operation 808 illustrates accepting the at least one attribute from a family medical history associated with the at least one individual. For example, as shown in FIG. 1, acceptor module 102 may accept the at least one attribute from a family medical history associated with the at least one individual. In one example, acceptor module 102 can accept from network storage 110 an attribute 120 including a list of family members that have had ovarian cancer from a family medical history associated with an anonymous individual or an individual named Elizabeth Green. A family medical history may include a list of previous illnesses, symptoms, medicines, treatments, health risk factors, operations, and/or doctor visits associated with family members related to the at (east one individual. In some instances, acceptor module 102 may include a computer processor.

Figure 9:
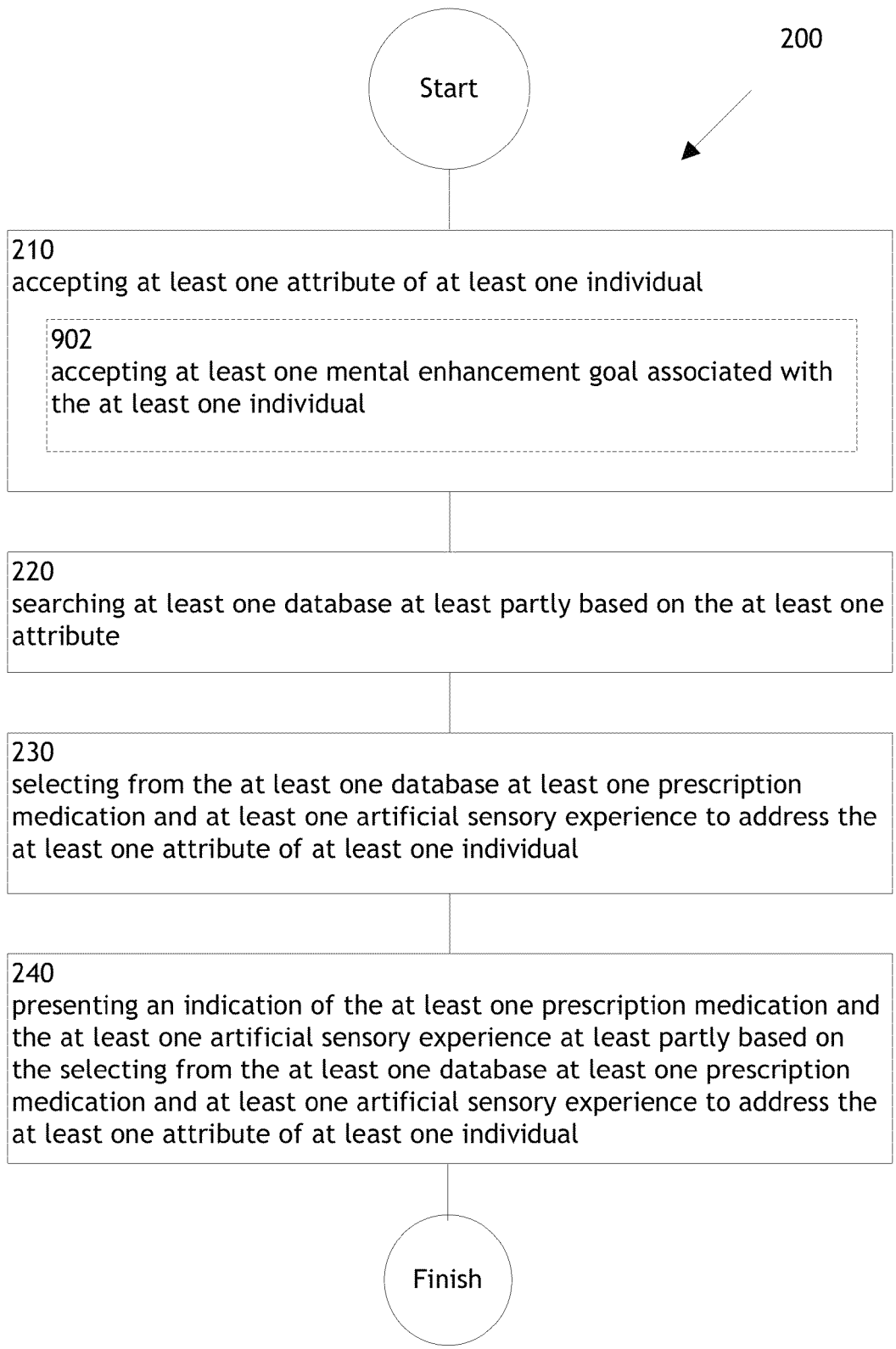
FIG. 9 illustrates an alternative embodiment of the operational flow of FIG. 2.

FIG. 9 illustrates alternative embodiments of the example operational flow 200 of FIG. 2. FIG. 9 illustrates example embodiments where operation 210 may include at least one additional operation. Additional operations may include an operation 902.

Operation 902 illustrates accepting at least one mental enhancement goal associated with the at least one individual. For example, as shown in FIG. 1, acceptor module 102 may accept at least one mental enhancement goal associated with the at least one individual. In one instance, acceptor module 102 can accept a mental enhancement goal associated with, for example, an individual named Dorothy Anderson. A mental enhancement goal may include a mental state and/or situation an individual may plan to achieve. Some examples of a mental enhancement goal may include achieving a certain state of mental awareness such as increased alertness or visual perception, reaching a certain cognitive capability such as enhanced memory or pattern recognition, maintaining a specific attention level, and/or reducing or eliminating a phobia. In some instances, acceptor module 102 may include a computer processor.

Figure 10:
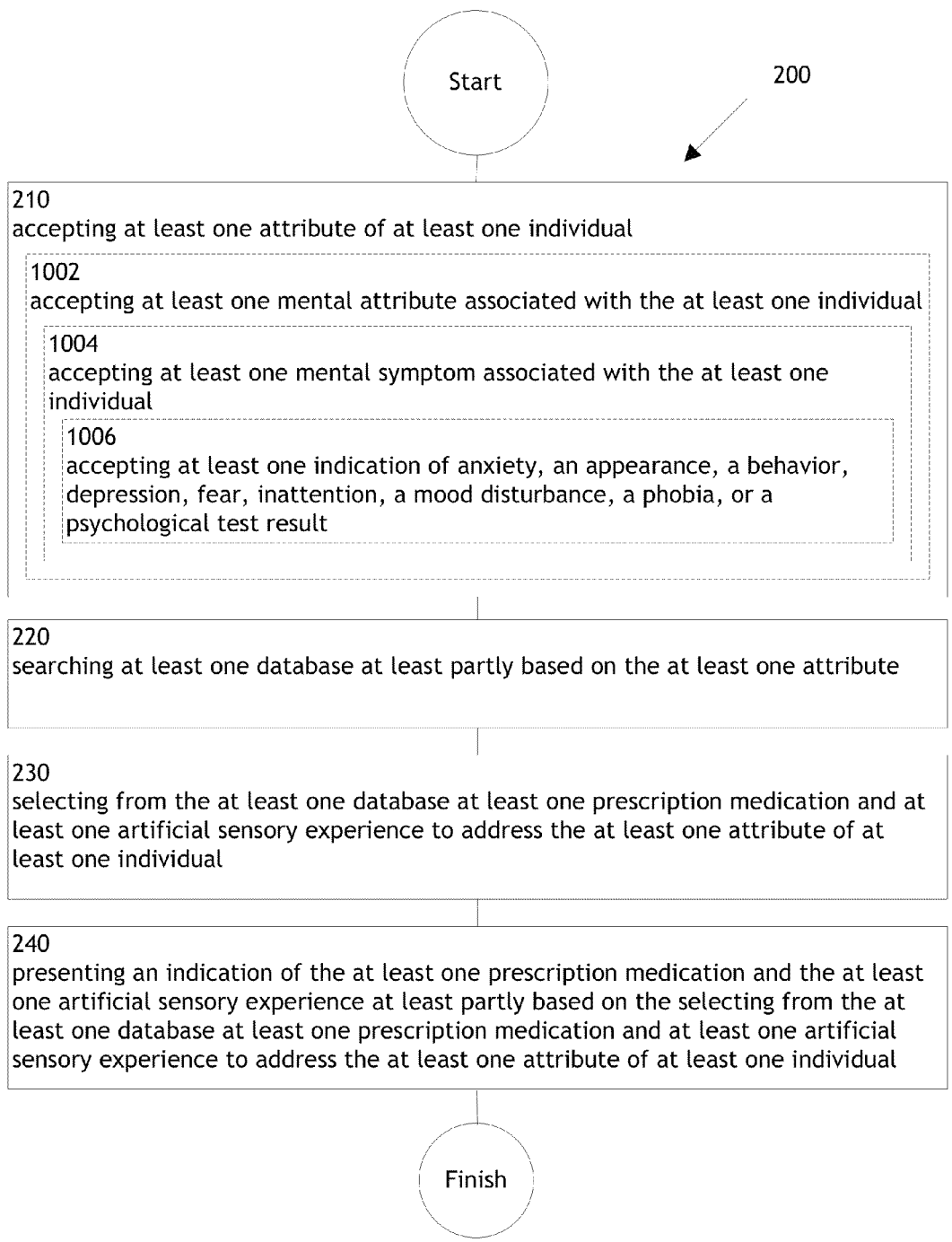
FIG. 10 illustrates an alternative embodiment of the operational flow of FIG. 2.

FIG. 10 illustrates alternative embodiments of the example operational flow 200 of FIG. 2. FIG. 10 illustrates example embodiments where operation 210 may include at least one additional operation. Additional operations may include an operation 1002, an operation 1004, and/or an operation 1006.

Operation 1002 illustrates accepting at least one mental attribute associated with the at least one individual. For example, as shown in FIG. 1, acceptor module 102 may accept at least one mental attribute associated with the at least one individual. In one example, acceptor module 102 can accept a mental attribute 120 including, for example, an intelligence quotient associated with an individual named Judy Peterson. A mental attribute may include an attribute that may be related to and/or associated with basic mental function and/or high-level brain function. Some examples of a mental attribute may include an intelligence quotient (IQ), measurements of brain activity for example using functional MRI or near infra-red technology, and/or measurements of mental development. In some instances, acceptor module 102 may include a computer processor.

Operation 1004 illustrates accepting at least one mental symptom associated with the at least one individual. For example, as shown in FIG. 1, acceptor module 102 may accept at least one mental symptom associated with the at least one individual. In one example, acceptor module 102 can accept from network storage 110 a mental symptom including a stress level measurement associated with an individual named Heather Swanson. A mental symptom may include a manifestation, sign, and/or an indication of the presence of a disease and/or some other mental disorder and/or abnormality. Some examples of a mental symptom may include lack of attention, indication of stress, hyperactivity, nervousness, and/or lack of responsiveness. In some instances, acceptor module 102 may include a computer processor.

Operation 1006 illustrates accepting at least one indication of anxiety, an appearance, a behavior, depression, fear, inattention, a mood disturbance, a phobia, or a psychological test result. For example, as shown in FIG. 1, acceptor module 102 may accept at least one indication of anxiety, appearance, behavior, depression, fear, inattention, mood disturbance, phobia, or psychological test result. In one example, acceptor module 102 can accept from user interface 116 and user 118 an indication of anxiety and depression. Anxiety may include feelings of fear, apprehension, and/or worry and may be accompanied by physical sensations. An appearance may include an outward, audible, and/or visible aspect of a person and/or thing associated with a person. A behavior may include the manner in which a person and/or thing associated with a person acts and/or reacts. Depression may include a mental state characterized by pessimism, a sense of inadequacy, despondence, despair, a tow level of energy, and/or a lack of activity. Fear may be caused by impending danger, perceived evil, and/or pain, whether real or imagined. Inattention may include the failure of a person to focus attention. A mood disturbance may include a change in emotional state. A phobia may include an irrational, and/or persistent fear of certain situations, objects, activities, and/or people. A psychological test result may include a sample behavior for inferring a certain generalization about a person. For example, a personality test result may indicate that person has obsessive/ compulsive characteristics. In some instances, acceptor module 102 may include a computer processor.

Figure 11:
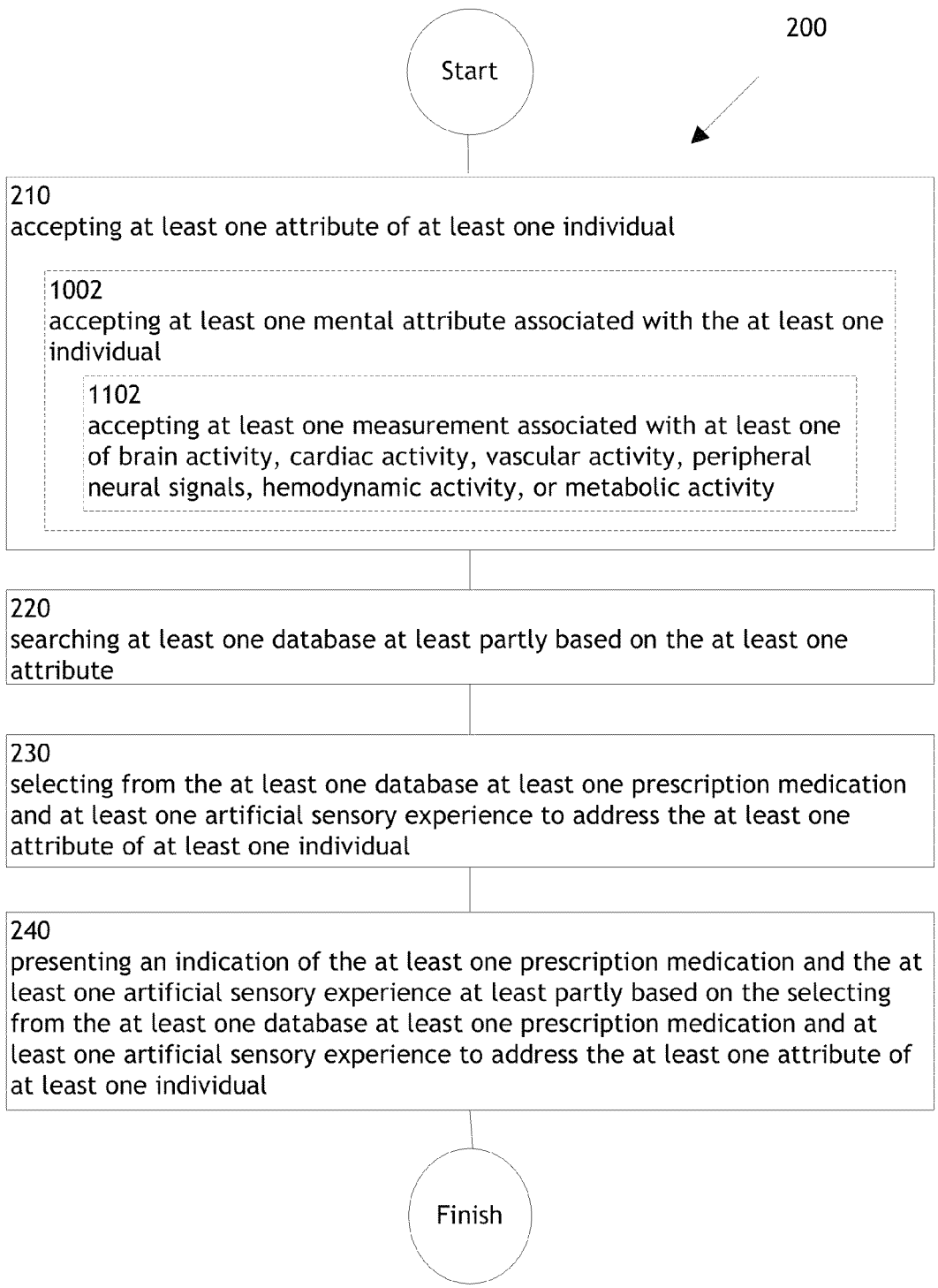
FIG. 11 illustrates an alternative embodiment of the operational flow of FIG. 2.

FIG. 11 illustrates alternative embodiments of the example operational flow 200 of FIG. 2. FIG. 11 illustrates example embodiments where operation 210 may include at least one additional operation. Additional operations may include an operation 1102.

Operation 1102 illustrates accepting at least one measurement associated with at least one of brain activity, cardiac activity, vascular activity, peripheral neural signals, hemodynamic activity, or metabolic activity. For example, as shown in FIG. 1, acceptor module 102 may accept at Least one measurement associated with at least one of brain activity, cardiac activity, vascular activity, peripheral neural signals, hemodynamic activity, or metabolic activity. In one instance, acceptor module 102 can accept from database entry 114 a measurement associated with brain activity. Brain activity may include the electrical activity of the brain, such as that measured by EEG, MEG, or the like. Other brain activity measurements may include functional MRI imaging, near infra-red imaging, PET scanning, or the like. Cardiac activity may include electrical activity in the heart, such as that measured by EKG or visual imaging. Vascular activity may include any activity and/or function of the circulatory system. Peripheral neural signals may include neural signals sent through the peripheral nervous system. Hemodynamic activity may include any activity associated with the circulatory system. Metabolic activity may include any activity associated with the biochemical reactions occurring in a living organism. In some instances, acceptor module 102 may include a computer processor.

Figure 12:
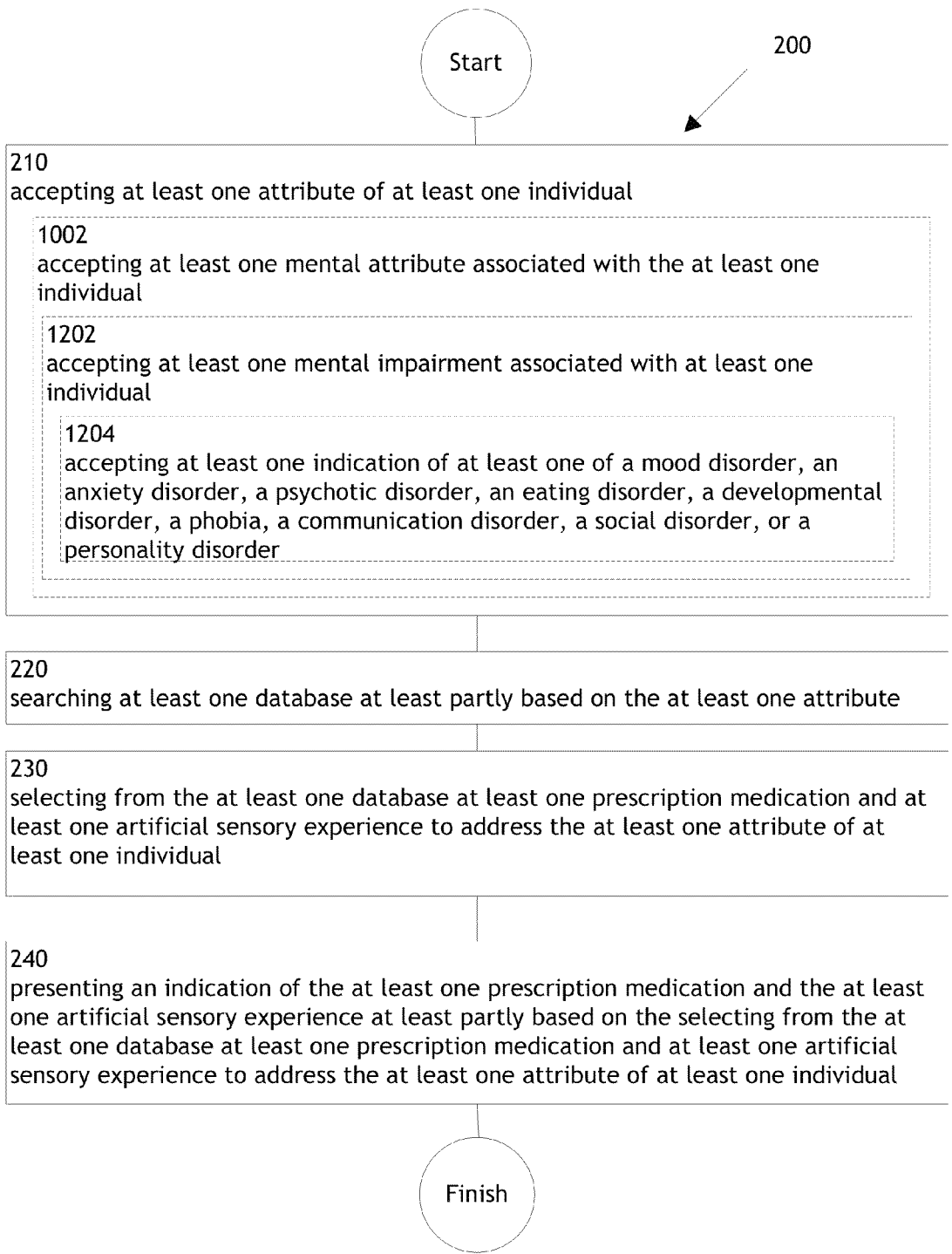
FIG. 12 illustrates an alternative embodiment of the operational flow of FIG. 2.

FIG. 12 illustrates alternative embodiments of the example operational flow 200 of FIG. 2. FIG. 12 illustrates example embodiments where operation 210 may include at Least one additional operation. Additional operations may include an operation 1202, and/or an operation 1204.

Operation 1202 illustrates accepting at least one mental impairment associated with at least one individual. For example, as shown in FIG. 1, acceptor module 102 may accept at least one mental impairment associated with at least one individual. In one example, acceptor module 102 can accept from memory device 112 a mental impairment associated with an individual named Richard Lewis. A mental impairment may include a condition or function judged by a health care provider to be significantly impaired relative to the usual standard of an individual of their group, and may include mental impairment, sensory impairment, and/or mental disease. In some instances, acceptor module 102 may include a computer processor.

Operation 1204 illustrates accepting at least one indication of at least one of a mood disorder, an anxiety disorder, a psychotic disorder, an eating disorder, a developmental disorder, a phobia, a communication disorder, a social disorder, or a personality disorder. For example, as shown in FIG. 1, acceptor module 102 may accept at least one indication of at Least one of a mood disorder, an anxiety disorder, a psychotic disorder, an eating disorder, a developmental disorder, a phobia, or a personality disorder. In one instance, acceptor module 102 can accept from user interface 116 and/or user 118 an indication of a mood disorder including a mood change and the onset of depression in a specific individual. A mood disorder may include a condition whereby the prevailing emotional mood is distorted or inappropriate to the circumstances, and may include examples such as bipolar disorder, an alteration in mood, and/or depression. An anxiety disorder may include nervous system disorders such as irrationality, illogical worry not based on fact, fear, and/or phobia. A psychotic disorder may include a state of mind in which thinking becomes irrational and/or disturbed and may include hallucinations, abnormal perception, mania, dementia, delusions and/or delusional beliefs, delirium, depression, psychosis personality disorder, personality changes, and/or disorganized thinking. An eating disorder may include a compulsion to eat and/or avoid eating that negatively affects physical and/or mental health. Some examples of an eating disorder may include anorexia nervosa and bulimia nervosa. A developmental disorder may include a disorder occurring in a child's development, which may retard development. Some examples of a developmental disorder may include an emotional disorder, a cognitive disorder, and/or a mental disorder accompanied by physical traits, such as Down syndrome. A phobia may include an irrational, intense, and/or persistent fear of certain situations, objects, activities, and/or persons. Examples of phobias include social phobias, arachnophobia, xenophobia, and/or claustrophobia. A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A personality disorder may include a disorder characterized by pathological trends in personality structure. Some examples of a personality disorder may include a paranoid personality disorder, a narcissistic personality disorder, and/or an obsessive-compulsive personality disorder. In some instances, acceptor module 102 may include a computer processor.

Figure 13:
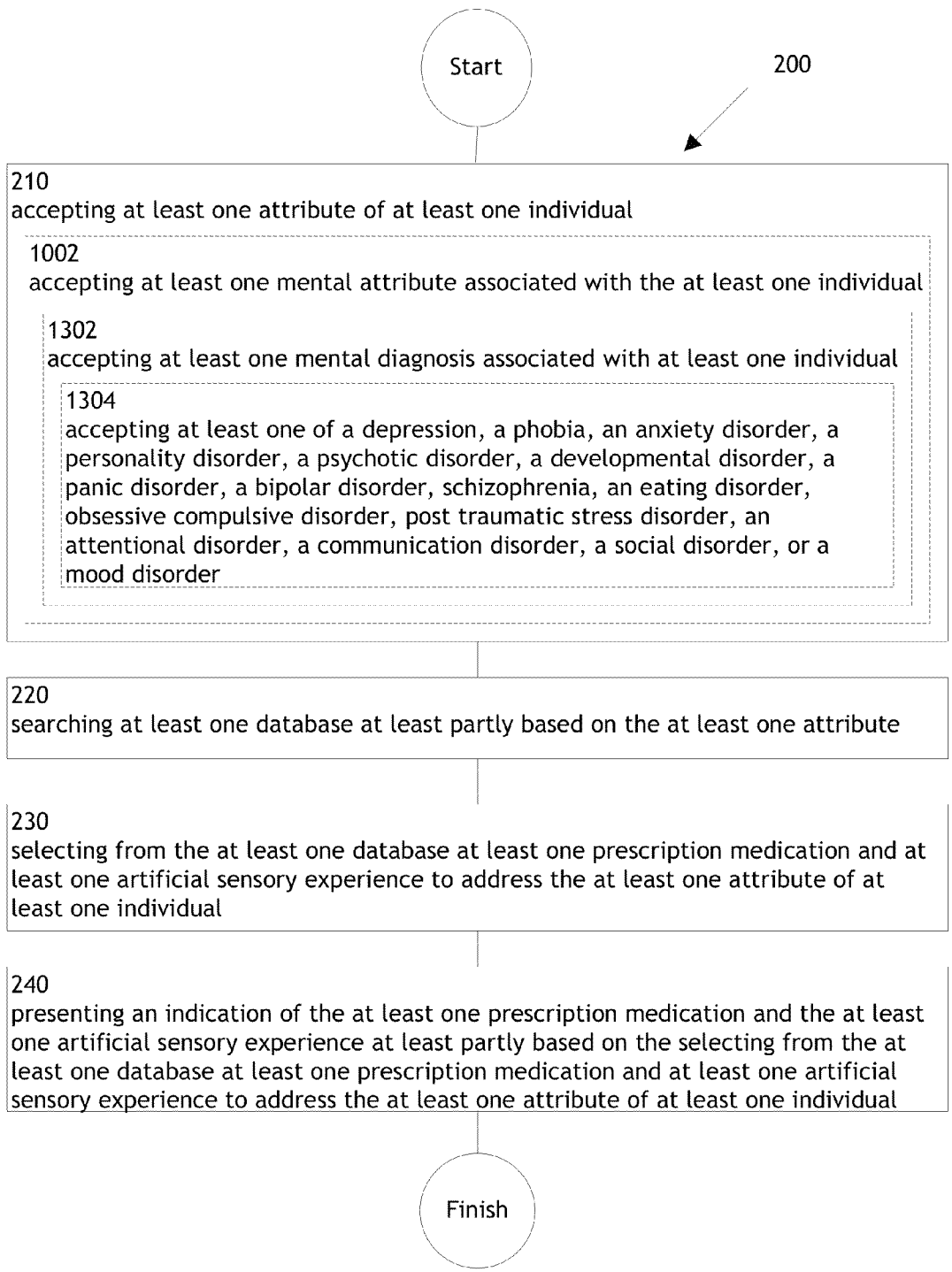
FIG. 13 illustrates an alternative embodiment of the operational flow of FIG. 2.

FIG. 13 illustrates alternative embodiments of the example operational flow 200 of FIG. 2. FIG. 13 illustrates example embodiments where operation 210 may include at least one additional operation. Additional operations may include an operation 1302, and/or an operation 1304. Further, operation 1302 illustrates accepting at least one mental diagnosis associated with at least one individual. For example, as shown in FIG. 1, acceptor module 102 may accept at least one mental diagnosis associated with at least one individual. In a specific instance, acceptor module 102 accepts from memory device 112 a mental diagnosis including a phobia associated with an anonymous individual or an individual named Roy Black. A mental diagnosis may include identifying a mental disorder and/or condition by its symptoms. Some examples of a mental diagnosis may include a mood disorder such as depression, an anxiety disorder such as PTSD, a behavioral disorder such as ADHD, a personality disorder such as borderline personality disorder, and/or a phobia. Mental disorders may include those listed in the Diagnostic and Statistical Manual of Mental Disorders (DSM). In some instances, acceptor module 102 may include a computer processor.

Operation 1304 illustrates accepting at least one of a depression, a phobia, an anxiety disorder, a personality disorder, a psychotic disorder, a developmental disorder, a panic disorder, a bipolar disorder, schizophrenia, an eating disorder, obsessive compulsive disorder, post traumatic stress disorder, an attentional disorder, a communication disorder, a social disorder, or a mood disorder. For example, as shown in FIG. 1, acceptor module 102 may accept at least one of a depression, a phobia, an anxiety disorder, a personality disorder, a psychotic disorder, a developmental disorder, a panic disorder, or a mood disorder. In one example, acceptor module 102 accepts from database entry 114 a diagnosis of depression. Depression may include a mental state characterized by a pessimistic sense of inadequacy and/or a despondent lack of activity. A phobia may include an irrational, intense, and/or persistent fear of certain situations, objects, activities, and/or persons. Some phobias may include social phobias, arachnophobia, xenophobia, and/or claustrophobia. An anxiety disorder may include nervous system disorders such as irrationality, illogical worry not based on fact, fears, and/or phobias. A personality disorder may include a disorder characterized by pathological trends in personality structure. Some examples of a personality disorder may include a paranoid personality disorder, a narcissistic personality disorder, and/or an obsessive-compulsive personality disorder. A psychotic disorder may include a state of mind in which thinking becomes irrational and/or disturbed and may include hallucinations, delusional beliefs, personality changes, and/or disorganized thinking. A developmental disorder may include a disorder occurring in a child's development, which may often retard development. Some examples of a developmental disorder may include psychological or physical disorders. A panic disorder may include a condition characterized by recurring panic attacks in combination with significant behavioral change. A bipolar disorder may include a mood disorder characterized by the presence of one or more episodes of abnormally elevated mood, such as Bipolar I disorder, Bipolar II disorder, cyclothymia, and/or Bipolar-NOS. Schizophrenia may include a mental illness characterized by impairments in the perception or expression of reality, most commonly manifesting as auditory hallucinations, paranoid or bizarre delusions or disorganized speech and thinking in the context of significant social or occupational dysfunction. An eating disorder may include a compulsion to eat or avoid eating, such as anorexia nervosa and/or bulimia nervosa. Obsessive compulsive disorder may include a psychiatric anxiety disorder characterized by obsessive, distressing, intrusive thoughts and related compulsions which attempt to neutralize the obsessions. Post traumatic stress disorder may include an anxiety disorder that can develop after exposure to one or more terrifying events in which grave physical harm occurred or was threatened. An attentional disorder may include a persistent pattern of inattention and/or hyperactivity, as well as forgetfulness, poor impulse control or impulsivity, and distractibility, such as attention-deficit hyperactivity disorder (ADHD). A communication disorder may include a disease and/or a condition partially or totally preventing human communication. Some examples of a communication disorder may include autism, stuttering, and/or aphasia. A social disorder may include a condition characterized by a difficulty in human interaction and/or emotional discomfort in social situations. Some examples of a social disorder may include stage fright, social anxiety disorder, and/or shyness. A mood disorder may include a condition whereby the prevailing emotional mood is distorted or inappropriate to the circumstances and may include examples such as bipolar disorder and/or depression. In some instances, acceptor module 102 may include a computer processor.

Figure 14:
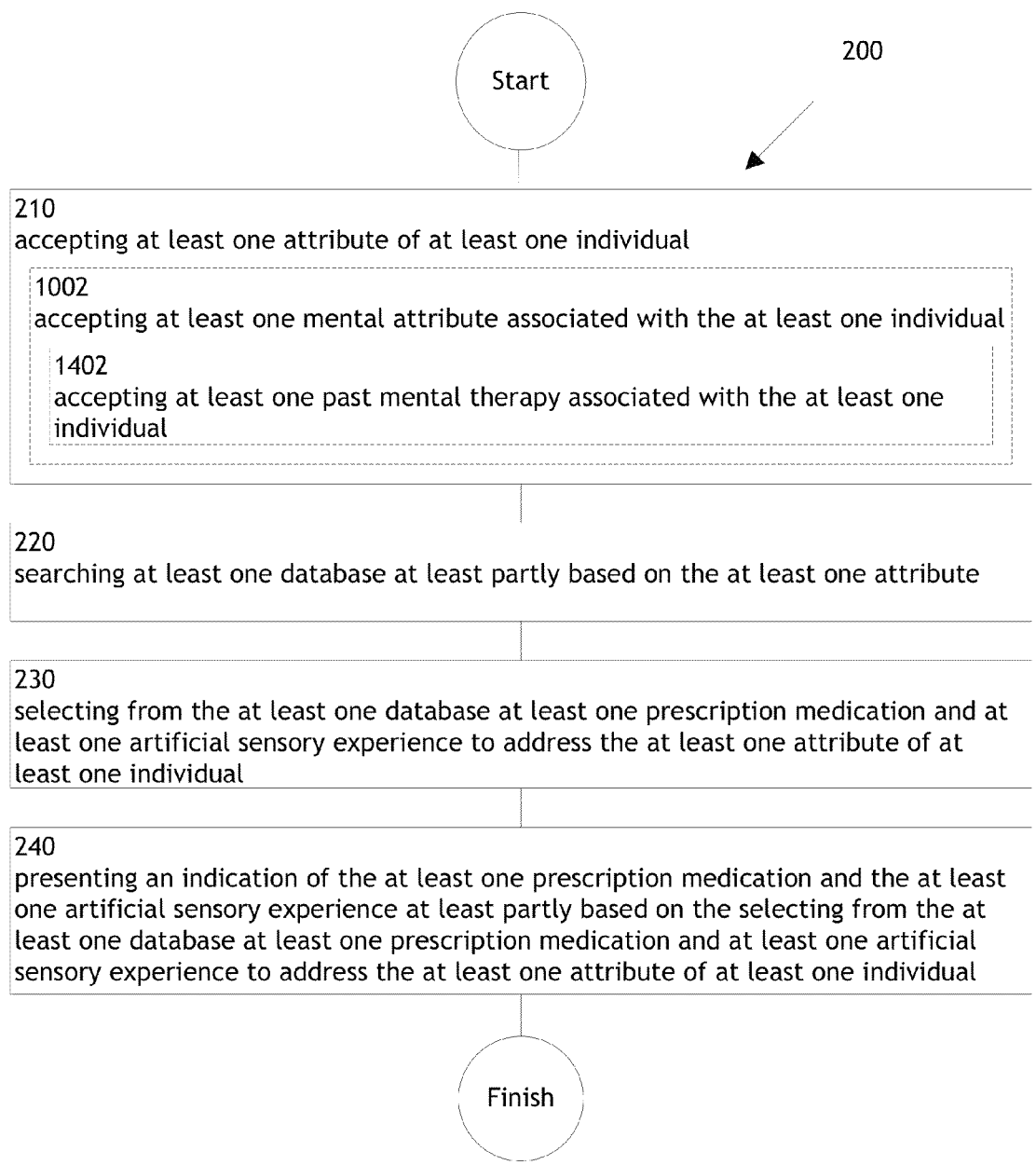
FIG. 14 illustrates an alternative embodiment of the operational flow of FIG. 2.

FIG. 14 illustrates alternative embodiments of the example operational flow 200 of FIG. 2. FIG. 14 illustrates example embodiments where operation 210 may include at least one additional operation. Additional operations may include an operation 1402. Further, operation 1402 illustrates accepting at least one past mental therapy associated with the at least one individual. For example, as shown in FIG. 1, acceptor module 102 may accept at least one past mental therapy associated with the at least one individual. In one instance, acceptor module 102 can accept from database entry 114 a past mental therapy associated with an individual named James Williams or an anonymous individual. A past mental therapy may include a list and/or a record of at least one mental therapy, such as an anti-depressant medication, administered to at least one individual. In some instances, acceptor module 102 may include a computer processor.

Figure 15:
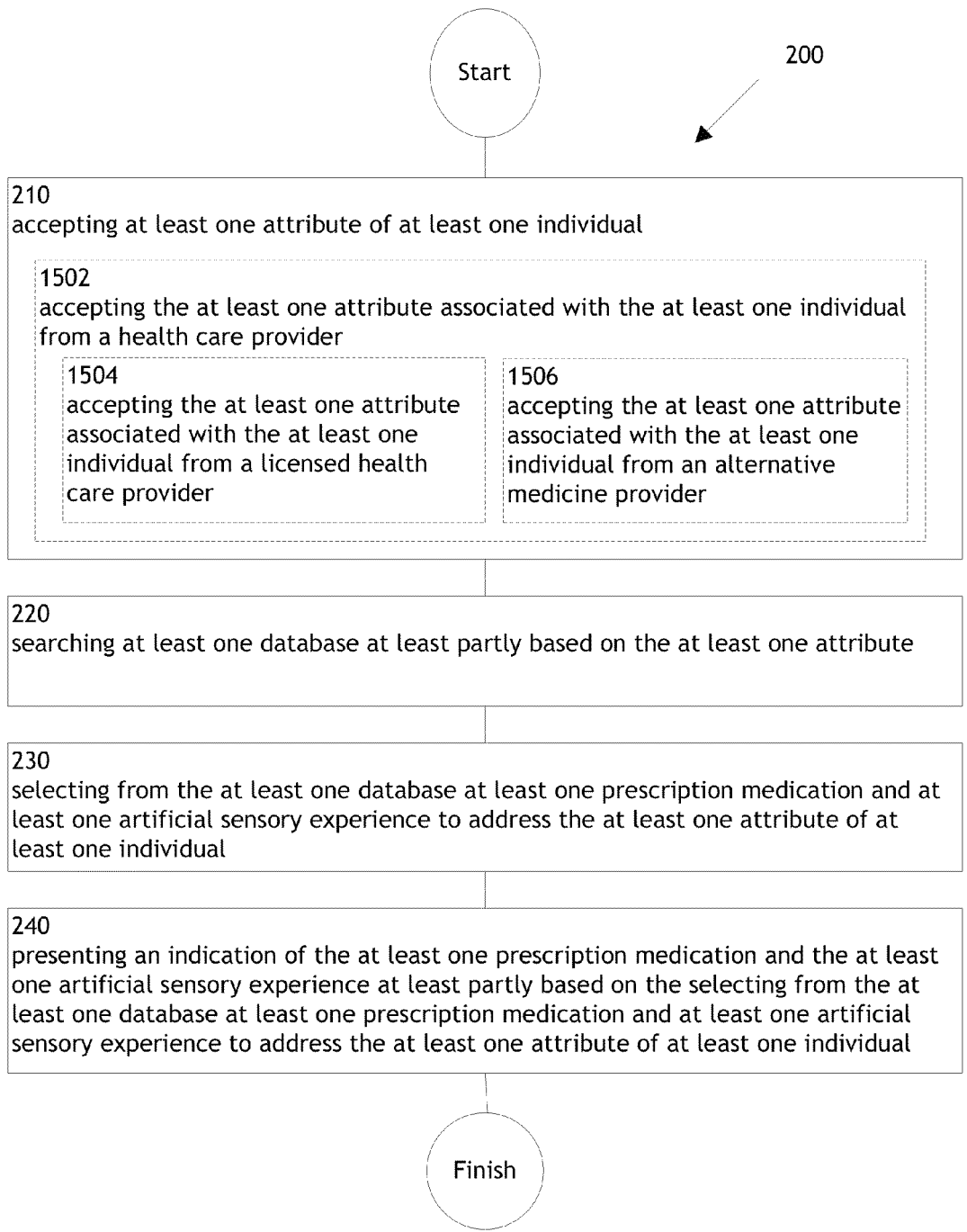
FIG. 15 illustrates an alternative embodiment of the operational flow of FIG. 2.

FIG. 15 illustrates alternative embodiments of the example operational flow 200 of FIG. 2. FIG. 15 illustrates example embodiments where operation 210 may include at least one additional operation. Additional operations may include an operation 1502, an operation 1504, and/or an operation 1506.

Operation 1502 illustrates accepting the at least one attribute associated with the at least one individual from a health care provider. For example, as shown in FIG. 1, acceptor module 102 may accept the at least one attribute associated with the at least one individual from a health care provider. In one example, acceptor module 102 can accept from user interface 116 and/or user 118 an attribute 120 including a medication history associated with a group of fifty individuals from a health care provider 136. A health care provider may include a hospital, a doctor, a nurse, a medical clinic, a dentist, and/or any provider of preventive, diagnostic, therapeutic, rehabilitative, maintenance, or palliative care and/or counseling. A healthcare provider may include a seller and/or dispenser of prescription drugs or medical devices. In some instances, acceptor module 102 may include a computer processor.

Operation 1504 illustrates accepting the at least one attribute associated with the at least one individual from a licensed health care provider. For example, as shown in FIG. 1, acceptor module 102 may accept the at least one attribute associated with the at least one individual from a licensed health care provider. In one instance, acceptor module 102 accepts from memory device 112 an attribute 120 including a symptom indication a phobia associated with an individual named Robert Clark from a licensed health care provider 136. A licensed health care provider may include a person licensed by a governing authority, such as a state, to provide medical and/or health care. Some examples of a licensed health care provider may include a licensed medical doctor or physician, a licensed physician's assistant, and/or a licensed nurse practitioner. In some instances, acceptor module 102 may include a computer processor.

Operation 1506 illustrates accepting the at least one attribute associated with the at least one individual from an alternative medicine provider. For example, as shown in FIG. 1, acceptor module 102 may accept the at (east one attribute associated with the at least one individual from an alternative medicine provider. In one instance, acceptor module 102 can accept from network storage 110 an attribute 120 associated with an individual named Connie Martin from an alternative medicine provider. An alternative medicine provider may include a provider of folk medicine, herbal medicine, diet fads, homeopathy, faith healing, new age healing, chiropractic, acupuncture, aromatherapy, naturopathy, massage, reflexology, hypnotism, and/or music therapy. In some instances, acceptor module 102 may include a computer processor.

Figure 16:
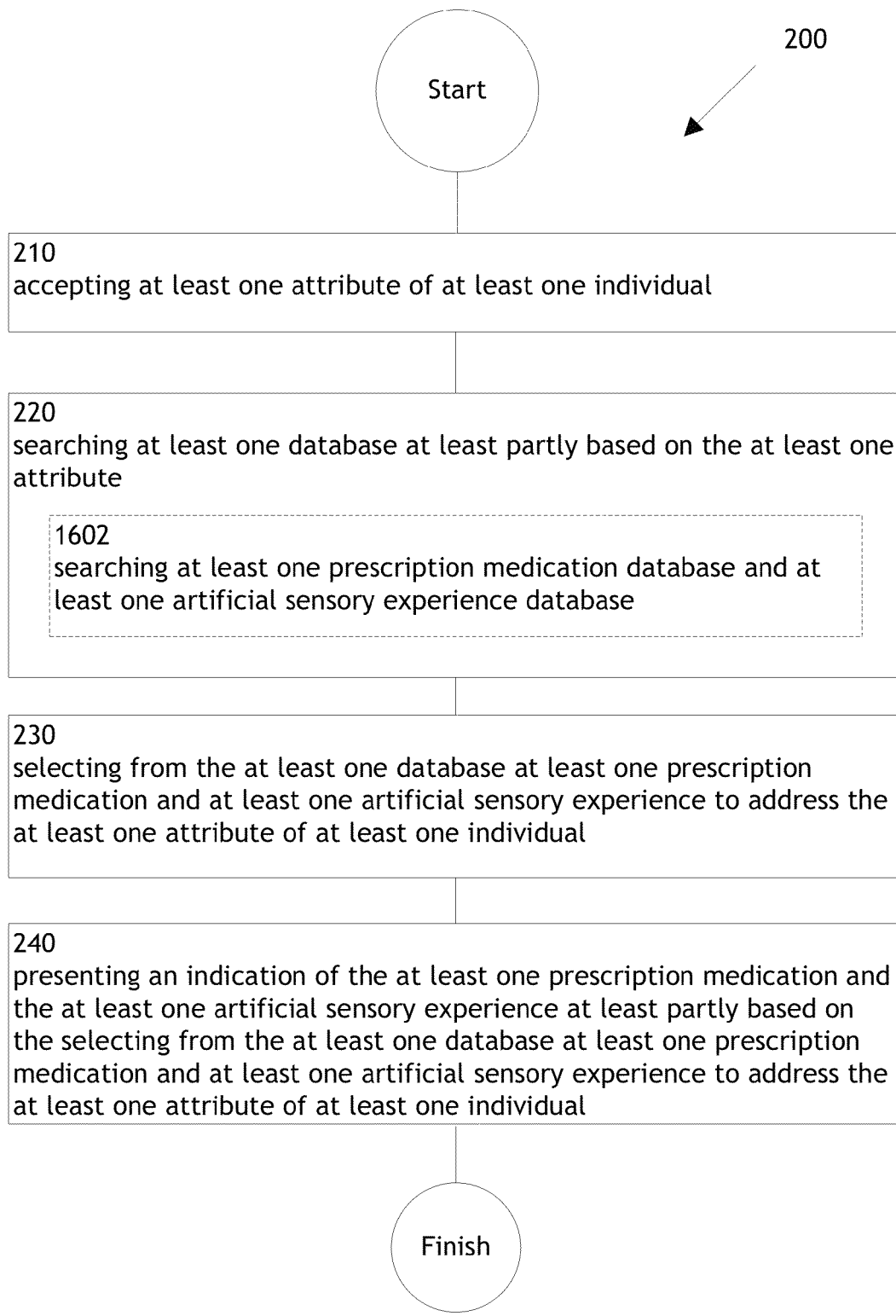
FIG. 16 illustrates an alternative embodiment of the operational flow of FIG. 2.

FIG. 16 illustrates alternative embodiments of the example operational flow 200 of FIG. 2. FIG. 16 illustrates example embodiments where operation 220 may include at least one additional operation. Additional operations may include an operation 1602.

Operation 1602 illustrates searching at least one prescription medication database and at least one artificial sensory experience database. For example, as shown in FIG. 1, querier module 104 may search at least one prescription medication database and at least one artificial sensory experience database. In one example, querier module 104 searches a medication database 124 and an artificial sensory experience database 126. A database may include a collection of data organized for convenient access. The database may include information digitally stored in a memory device 112, as at least a portion of at least one database entry 114, and/or in network storage 110. In some instances, the database may include information stored non-digitally such as at least a portion of a book, a paper file, and/or a non-computerized index and/or catalog. Non-computerized information may be received by acceptor module 102 by scanning or by manually entering the information into a digital format. A prescription database and/or medication database may include any database associated with at least one prescription medication and may be available to health care professionals and/or the public. An artificial sensory experience database may include any database associated with at least one artificial sensory experience and may include a database accessible by the public and/or a health care provider. In some instances, acceptor module 102 and/or querier module 104 may include one or more computer processors.

Figure 17:
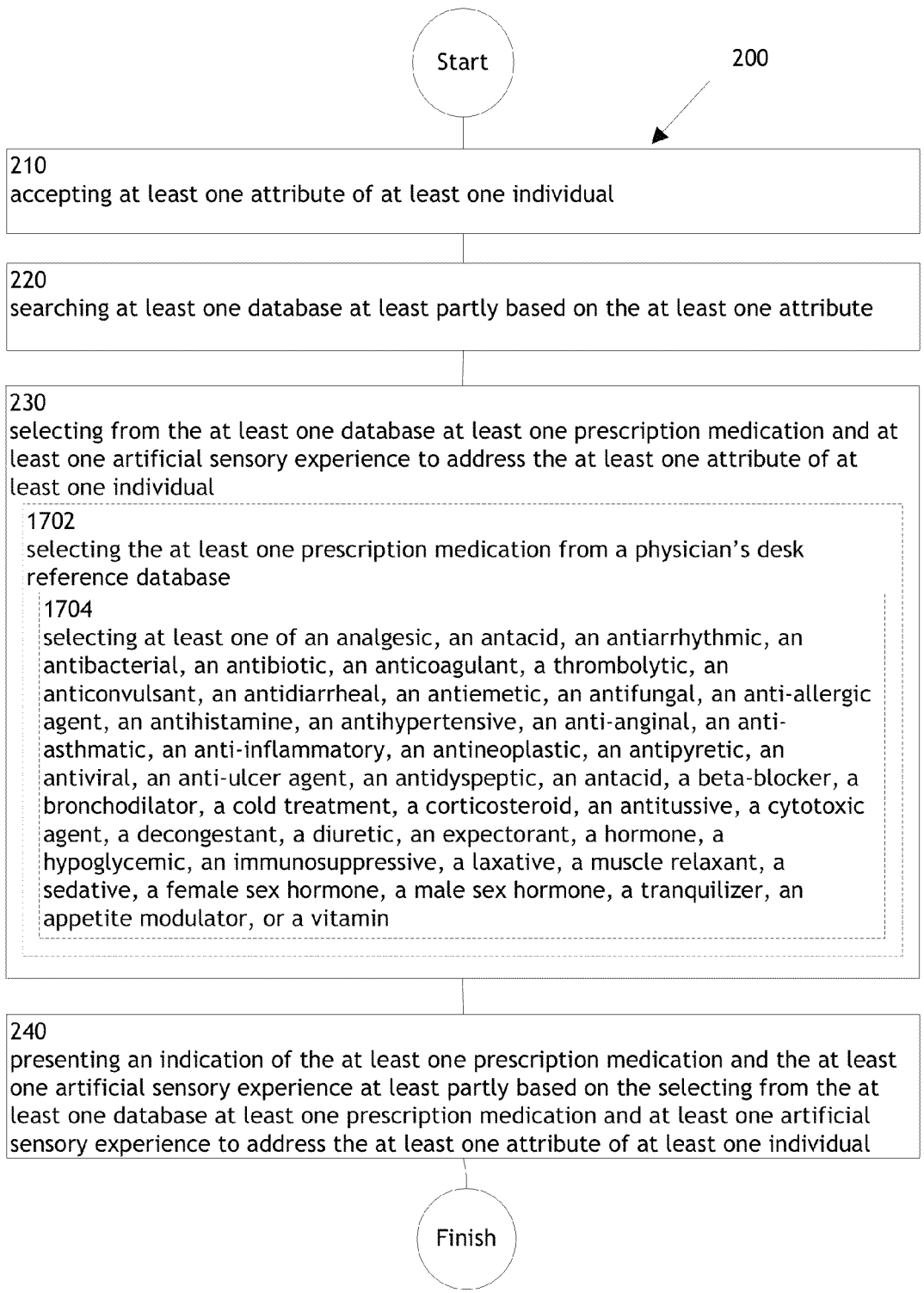
FIG. 17 illustrates an alternative embodiment of the operational flow of FIG. 2.

FIG. 17 illustrates alternative embodiments of the example operational flow 200 of FIG. 2. FIG. 17 illustrates example embodiments where operation 230 may include at least one additional operation. Additional operations may include an operation 1702, and/or an operation 1704.

Operation 1702 illustrates selecting the at least one prescription medication from a physician's desk reference database. For example, as shown in FIG. 1, selector module 106 may select the at least one prescription medication from a physician's desk reference database. In one example, selector module 106 selects the at least one prescription medication from a physician's desk reference database 122, such as a PDR psychiatry database. In some instances, selector module 106 may include a computer processor.

Operation 1704 illustrates selecting at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, an antitussive, a cytotoxic agent, a decongestant, a diuretic, an expectorant, a hormone, a hypoglycemic, an immunosuppressive, a laxative, a muscle relaxant, a sedative, a female sex hormone, a male sex hormone, a tranquilizer, an appetite modulator, or a vitamin. For example, as shown in FIG. 1, selector module 106 may select at least one of an analgesic, an antacid, an antiarrhythmic, an antibacterial, an antibiotic, an anticoagulant, a thrombolytic, an anticonvulsant, an antidiarrheal, an antiemetic, an antifungal, an anti-allergic agent, an antihistamine, an antihypertensive, an anti-anginal, an anti-asthmatic, an anti-inflammatory, an antineoplastic, an antipyretic, an antiviral, an anti-ulcer agent, an antidyspeptic, an antacid, a beta-blocker, a bronchodilator, a cold treatment, a corticosteroid, a cough suppressant, an antitussive, a cytotoxic agent, a decongestant, a diuretic, an expectorant, a hormone, a hypoglycemic, an immunosuppressive, a Laxative, a muscle relaxant, a sedative, a female sex hormone, a male sex hormone, a tranquilizer, an appetite modulator, or a vitamin. An analgesic may include a drug and/or other medication suitable for relieving pain. Additionally, an analgesic may be effective for relieving different degrees of pain. Some examples of an analgesic may include narcotics such as morphine or oxycodone, non-narcotics, an NSAID such as aspirin or naproxen or ibuprofen, and/or acetaminophen. An antacid may include a substance for neutralizing stomach acid, such as a proton pump inhibitor. Some examples of an antacid may include it eprazole and/or a pharmaceutical composition containing aluminum hydroxide, magnesium hydroxide, aluminum carbonate, calcium carbonate, sodium bicarbonate, hydrotalcite, bismuth subsalicylate, magaldrate, and/or simethicone.

An antiarrhythmic may include a drug for controlling a heartbeat irregularity. Some examples of an antiarrhythmic may include a beta blocker such as propanolol, and/or lidocaine, verapamil, and/or quinidine. An antibacterial may include a drug used to treat an infection. Some examples of an antibacterial may include amoxicillin and/or ciprofloxacin. An antibiotic may include a drug made from naturally occurring and/or synthetic substances for combating a bacterial infection. Some examples of an antibiotic may include penicillin, streptomycin, and/or sulfonamide-based drugs. An anticoagulant may include an agent for preventing blood clots. An example of an anticoagulant may include a vitamin K antagonist, such as warfarin, and/or aspirin. A thrombolytic may help dissolve and disperse a blood clot and may be prescribed for patients with recent arterial or venous thrombosis. A thrombolytic may be derived from *Streptomyces* spp. and/or recombinant DNA technology and may include streptokinase, urokinase, and/or a tissue plasminogen activator (TPA) such as alteplase.

An anticonvulsant may include a pharmaceutical administered for the prevention of seizures. Some examples of an anticonvulsant may include a barbiturate, a carbamate, a fatty acid derivative, and/or a sulfonamide. An antidiarrheal may include a drug utilized for the relief of diarrhea. Some examples of an antidiarrheal may include an antispasmodic such as diphenoxylate and loperamide, a bismuth compound, a bulking agent, and/or an absorbent. An antiemetic may include a drug used to treat nausea and vomiting. Some examples of an antiemetic may include a 5-HT3 receptor antagonist, a dopamine antagonist, and/or a histamine. An antifungal may include a drug used to treat fungal infections, the most common of which affect the hair, skin, nails, and/or mucous membranes. Some examples of antifungals may include polyene antifungals, imidazole and triazole antifungals, and/or allylamines. An anti-allergenic agent may include an agent characterized by preventing and/or reducing the effect of an allergen. Some examples of an anti-allergenic may include an antihistamine, cortisone, hydrocortisone, and/or epinephrine. An antihistamine may include an agent used for counteracting the effects of histamine. Some examples of an antihistamine may include a H1-receptor antagonist and/or a H2-receptor antagonist. An antihypertensive may include drugs utilized for lowering blood pressure. Some examples of an antihypertensive may include a diuretic, an adrenergic receptor antagonist, and/or an ACE inhibitor. An anti-anginal may include an agent used for preventing and/or reducing angina and/or chest pain. Some examples of an anti-anginal may include aspirin, ranolazine, and/or ivabradine. An anti-asthmatic may include an agent for preventing and/or reducing asthma and/or its effects. Some examples of an anti-asthmatic may include albuterol, an inhaled steroid, for example budesonide or fluticasone, and/or ipratropium bromide.

An anti-inflammatory may include an agent utilized to reduce inflammation and/or to treat redness, heat, swelling, and/or increased blood flow associated for example, that seen with an infection or injury, or in many chronic diseases such as rheumatoid arthritis and gout. Some anti-inflammatories may include steroids, and/or NSAIDs such as naproxen, ibuprofen, and/or aspirin. An antineoplastic may include drugs used to treat cancer and to inhibit and/or prevent the development of tumors. Some antineoplastics may include alkylating agents, antimetabolites, enzymes, enzyme inhibitors, immune modulators, and taxoids. An antipyretic may include a drug used to reduce a fever. Some examples of an antipyretic may include aspirin and/or acetaminophen. An antiviral may include a drug used to treat viral infections and/or to provide temporary protection against viral infections such as influenza. Some examples of an antiviral may include an interferon, acyclovir, ribavirin, and/or oseltamivir. An anti-ulcer agent may include an agent used for preventing and/or lessening the effect of an ulcer, including stomach ulcers, mouth ulcers, or other types of ulcers. Some examples of an anti-ulcer agent may include a bismuth compound, a prostaglandin analogue, and/or cimetidine. An antidyspeptic may include an agent used for treating and/or preventing dyspepsia. Some examples of an antidyspeptic may include simethicone and/or a proton pump inhibitor, such as esomeprazole. An antacid may include a substance, often a base, which may counteract stomach acidity. Some examples of an antacid may include magnesium hydroxide, aluminum hydroxide, calcium carbonate, and/or bismuth subsalicytate. A beta-blocker may include a beta-adrenergic blocking agent utilized for reducing the oxygen needs of the heart by reducing the heartbeat rate. Some examples of a beta-blocker may include propranolol, esmolol, bisoprolol, and/or timolol. A bronchodilator may include an agent utilized for opening the bronchial tubes within the lungs when the tubes have become narrowed, for example, by muscle spasm and may be used for treating asthma. Some examples of a bronchodilator may include albuterol and/or ipratropium bromide. A cold treatment may include an agent utilized for treating aches, pains, and/or fever accompanying a cold. Some cold treatments may include aspirin, acetaminophen, a decongestant, an antihistamine, and/or caffeine.

A corticosteroid may include a hormonal preparation used as an anti-inflammatory for arthritis or asthma and/or treating some malignancies or compensating for a deficiency of natural hormones. Some examples of a corticosteroid may include cortisol and/or aldosterone. A cough suppressant may include an agent used to soothe irritation caused by coughing and/or to prevent coughing. Some examples of a cough suppressant may include codeine, an antihistamine, and/or dextromethorphan. An antitussive may include a cough suppressant. A cytotoxic agent may include a drug used for killing and/or damaging cells. Some examples of a cytotoxic agent may include actinomycin-D, azathioprine, bleomycin, melphalan, busulphan, doxorubicin, etoposide, an antineoplastic agent, and/or an apoptotic agent. A decongestant may include an agent for reducing the swelling of the mucous membranes lining the nose and/or throat. Some examples of a decongestant may include pseudoephedrine and phenytephrine. A diuretic may include an agent for increasing the quantity of urine produced by the kidneys and passed out of the body. Some examples of a diuretic may include hydrochlorothiazide, spironolactone, mannitol, and/or glucose. An expectorant may include an agent for stimulating the flow of saliva, loosening and thinning mucus in airways, and/or promoting a more productive cough as to eliminate phlegm from the respiratory tract. An example of an expectorant may include guaifenesin. A hormone may include molecules produced naturally by the endocrine glands. Some examples of a hormone may include steroid hormones, amine-derived hormones, peptide hormones, and/or lipid and phospholipid-derived hormones. A hypoglycemic may include an agent for lowering the level of glucose in the blood. Some examples of a hypoglycemic may include a sulfonylurea, a meglitinide, a biguanide, a thiazotidinedione, and/or a alpha-glucosidase inhibitor. An immunosuppressive may include an agent for preventing or reducing the body's normal reaction to invasion by disease and/or foreign tissues. Some examples of an immunosuppressive may include a drug such as a corticosteroid, cyclosporine, rapamycin, which acts on immunophilins, and/or an antibody.

A laxative may include an agent for increasing the frequency and ease of bowel movements. Some examples of a laxative may include methylcellulose, docusate, mineral oil, and/or magnesium hydroxide. A muscle relaxant may include an agent utilized for relieving muscle spasms. Some examples of a muscle relaxant may include neuromuscular blocking drugs, carisoprodol, cyclobenzaprine, metaxalone, a benzodiazepine and/or a tranquilizer. A sedative may include a substance which depresses the central nervous system and may result in calmness, relaxation, reduction of anxiety, sleepiness, and/or slowed breathing. Some examples of a sedative may include zolpidem, and/or eszopiclone. A female sex hormone may include a hormone responsible for the development of female secondary sexual characteristics. Some examples of a female sex hormone may include estrogen and progesterone. A male sex hormone may include a hormone responsible for the development of secondary male sexual characteristics. One example of a mate sex hormone may include testosterone. Sex hormone-related agents may include agents metabolically related to sex hormones. Examples of sex hormone-related agents may include sterols, androgens (testosterone), progestogens estrogens (estradiols, estrone), follicle-stimulating hormone, luteinizing hormone, inhibin B, anti-Mullerian hormone thyroid-related hormones. A tranquilizer may include any drug having a calming and/or sedative effect. Some examples of a tranquilizer may include an antidepressant, a barbiturate, and/or a benzodiazepine. An appetite modulator may include an agent used for regulating and/or adjusting appetite. Some examples of an appetite modulator may include recombinant PYY 3-36 and/or sibutramine. A vitamin may include chemicals essential in relatively small quantities for good health. Some examples of a vitamin may include Vitamin A, Vitamin C, Vitamin D, and/or Vitamin K.

In one instance, selector module 106 can select an analgesic and an antipsychotic for subsequent presentation, perhaps in response to accepting a pain symptom and a hallucination symptom as the at least one attribute. In some instances, selector module 106 may include a computer processor.

Figure 18:
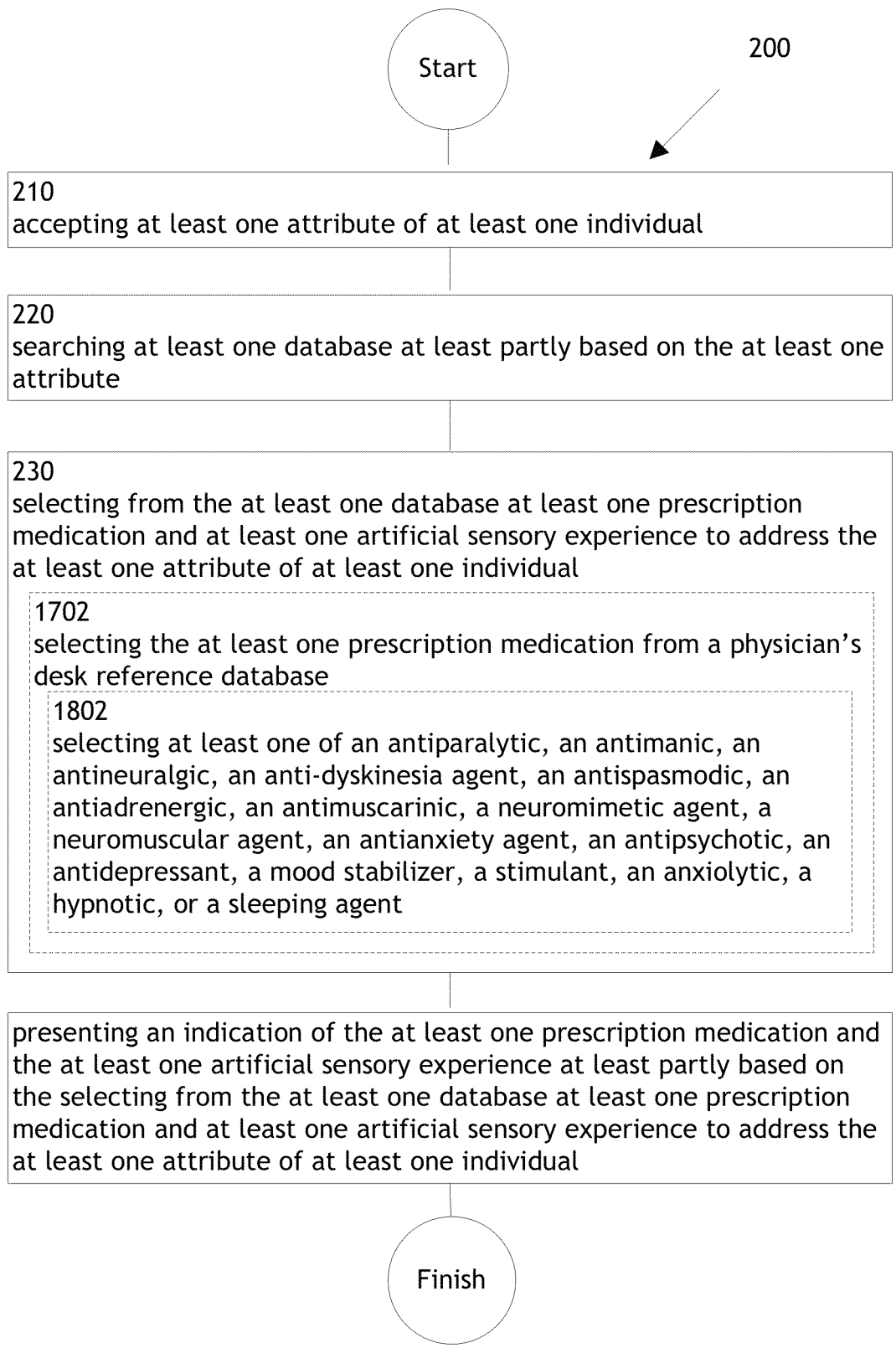
FIG. 18 illustrates an alternative embodiment of the operational flow of FIG. 2.

FIG. 18 illustrates alternative embodiments of the example operational flow 200 of FIG. 2. FIG. 18 illustrates example embodiments where operation 230 may include at least one additional operation. Additional operations may include an operation 1802. Further, operation 1802 illustrates selecting at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety agent, an antipsychotic, an antidepressant, a mood stabilizer, a stimulant, an anxiolytic, a hypnotic, or a sleeping agent. For example, as shown in FIG. 1, selector module 106 may select at least one of an antiparalytic, an antimanic, an antineuralgic, an anti-dyskinesia agent, an antispasmodic, an antiadrenergic, an antimuscarinic, a neuromimetic agent, a neuromuscular agent, an antianxiety drug, an antipsychotic, an antidepressant, a mood stabilizer, a stimulant, an anxiolytic, a hypnotic, and/or a sleeping agent such as a long-acting barbiturate. In one example, selector module 106 selects an antianxiety drug and a sleeping agent. An antiparalytic may include an agent used for preventing the loss of and/or recovering muscle function. One example of an antiparalytic may include methylprednisolone. An antimanic may include an agent used for treating and/or suppressing mania. Some examples may include lamotrigine and/or carbamazepine. An antineuralgic may include an agent for relieving paroxysmal nerve pain. One example of an antineuralgic may include carbamazepine. An anti-dyskinesia agent may include an agent used for reducing and/or preventing dyskinesia, including involuntary muscle movement. One example of an anti-dyskinesia agent may include methylenedioxymethamphetamine. An antispasmodic may include a drug or an herb that suppresses smooth muscle contraction. Some examples of an antispasmodic may include dicyclomine and/or hyoscyamine. An antiadrenergic may include a medication for inhibiting the functioning of the sympathetic nervous system. Some examples of an antiadrenergic may include clonidine and/or mecamylamine. An antimuscarinic may include an agent for reducing the activity of the muscarinic acetylcholine receptor. Some examples of an antimuscarinic may include atropine and/or hyoscine. A neuromimetic agent may include an agent that mimics the response of an effector organ to nerve impulses. A neuromuscular agent may block neuromuscular transmission at the neuromuscular junction and cause paralysis of the affected skeletal muscles. Some examples of a neuromuscular agent may include atracurium and/or vecuronium. An antianxiety drug may include a drug for suppressing anxiety and relaxing the muscles. An antianxiety drug may include a sedative, a tranquilizer, an anxiolytic, such as a benzodiazepine, alprazolam and/or diazepam, an antidepressant, a short-acting barbiturate, and/or an herbal treatment, such as chamomile, kava extract, Kratom, and/or valerian. An antipsychotic may include a group of drugs commonly used to treat psychosis and may include phenothiazines, thioxanthenes, butyrophenones, risperidone, amisulpride, and/or other suitable drugs. An antidepressant may include a psychiatric medication or other substance, such as a nutrient or herb, used for alleviating depression or dysthymia. Some examples of an antidepressant may include a selective serotonin reuptake inhibitor, such as Prozac and/or Zoloft, and/or a serotonin-norepinephrine reuptake inhibitor, such as Cymbalta. A mood stabilizer may include a psychiatric medication used to treat mood disorders characterized by intense and sustained mood shifts. Some examples of a mood stabilizer may include lithium carbonate and/or lamotrigine. A stimulant may include substances that may temporarily increase alertness and awareness, such as caffeine, ephedrine, and/or nicotine. An anxiolytic may include a substance used for the treatment of anxiety, such as a benzodiazepine and/or a barbiturate. A hypnotic may include substances that induce sleep, such as a barbiturate and/or an antihistamine (diphenhydramine). A sleeping agent may include any number of medications for helping a person sleep and/or stay asleep and may include benzodiazepines, antidepressants, melatonin, and/or antihistamines as well as other suitable substances. In some instances, selector module 106 may include a computer processor.

Figure 19:
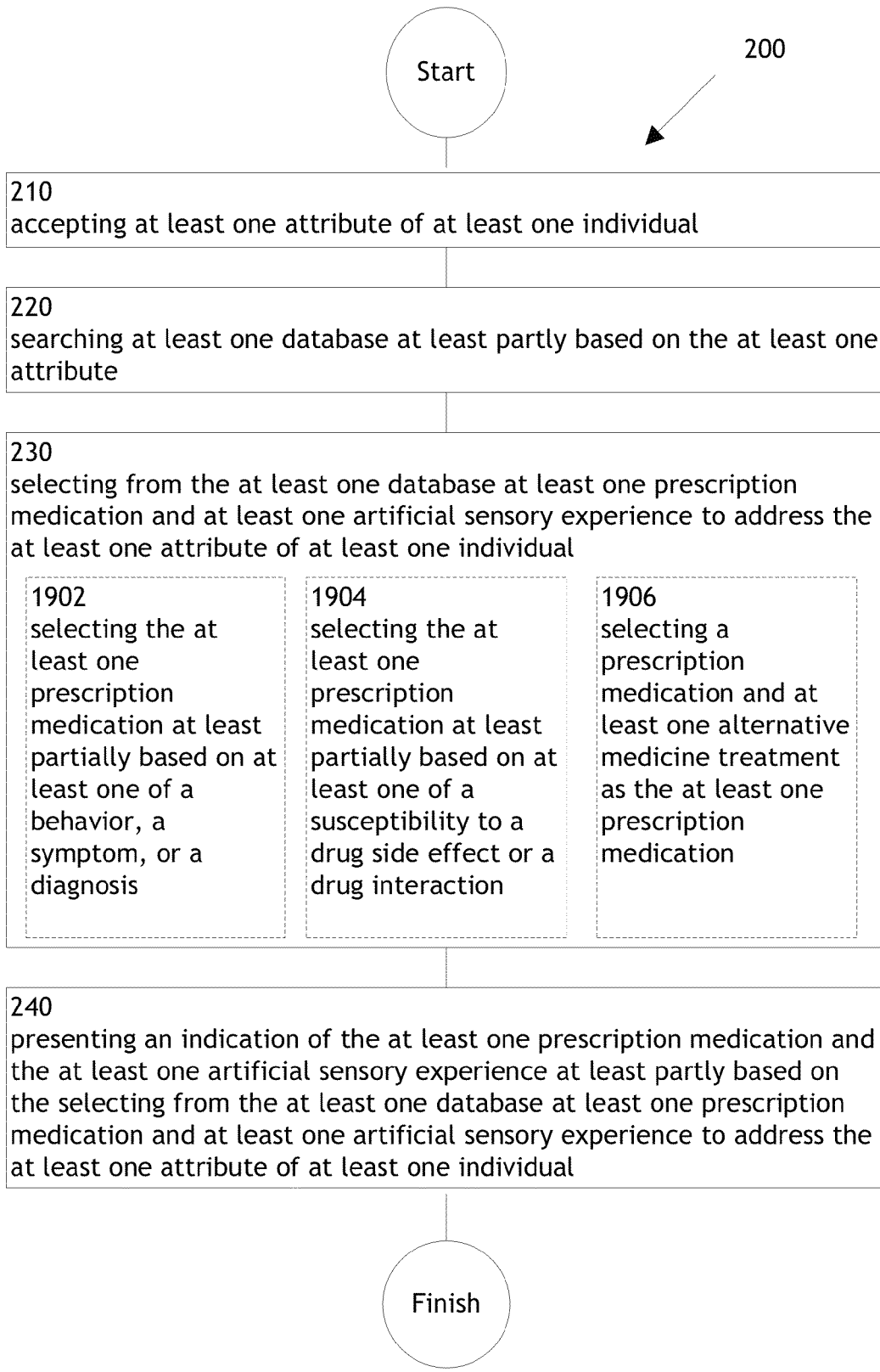
FIG. 19 illustrates an alternative embodiment of the operational flow of FIG. 2.

FIG. 19 illustrates alternative embodiments of the example operational flow 200 of FIG. 2. FIG. 19 illustrates example embodiments where operation 230 may include at least one additional operation. Additional operations may include an operation 1902, an operation 1904, and/or an operation 1906.

Operation 1902 illustrates selecting the at least one prescription medication at least partially based on at least one of a behavior, a symptom, or a diagnosis. For example, as shown in FIG. 1, selector module 106 may select the at least one prescription medication at least partially based on at least one of a behavior, a symptom, or a diagnosis. In one instance, selector module 106 can select a prescription medication based on a diagnosis. A behavior may include the manner a person behaves toward other people and/or a certain circumstance. A symptom may include a subjective indicator of a health problem reported by an individual, or a sign of a health problem noticed by another, perhaps a doctor. A symptom may be evidence of a disease, a disability, an impairment, and/or a condition. A diagnosis may include an identification of a disease, a disability, an impairment, and/or a condition. In some instances, selector module 106 may include a computer processor.

Operation 1904 illustrates selecting the at least one prescription medication at least partially based on at least one of a susceptibility to a drug side effect or a drug interaction. For example, as shown in FIG. 1, selector module 106 may select the at Least one prescription medication at least partially based on at Least one of a susceptibility to a drug side effect or a drug interaction. In one instance, selector module 106 can select a prescription medication based on a susceptibility to a drug side effect including an allergy. A susceptibility to a drug side effect may include a probability a certain person may be vulnerable to a side effect associated with a specific drug and/or medication. A susceptibility to a drug side effect may include predisposition to a particular drug side effect or class of drug side effects, such as upset stomach associated with aspirin formulations. A drug reaction may include a possible response a person may exhibit resulting from at least one drug and/or medication administered to the person. A drug reaction may include an allergy and/or a drug and/or medication interaction with a separate drug and/or medication. In some instances, selector module 106 may include a computer processor.

Operation 1906 illustrates selecting a prescription medication and at least one alternative medicine treatment as the at least one prescription medication. For example, as shown in FIG. 1, selector module 106 may select a prescription medication and at least one alternative medicine treatment as the at least one prescription medication. In one instance, selector module 106 can select a prescription medication and at least one alternative medicine treatment as the at Least one prescription medication. A prescription medication may include a medication, drug, and/or treatment available only with written instructions from a doctor, dentist, and/or other licensed professional. An alternative medicine treatment may include medical and/or nutraceutical treatments and/or practices utilized instead of standard medical treatments. Some examples of alternative medicine treatments may include chiropractic, herbal medicine, acupuncture, homeopathy, naturopathy, and/or spiritual devotions. In some instances, selector module 106 may include a computer processor.

Figure 20:
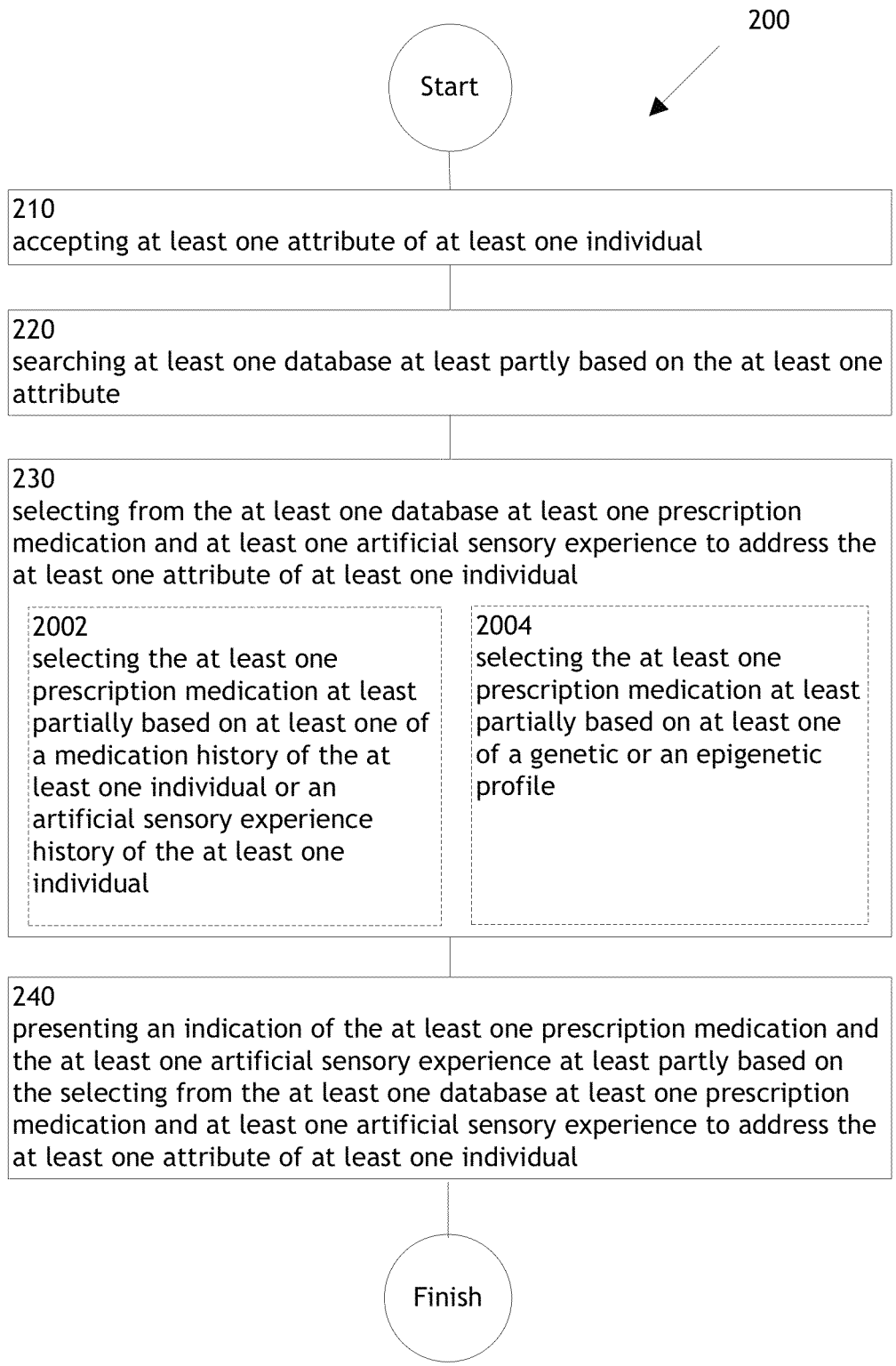
FIG. 20 illustrates an alternative embodiment of the operational flow of FIG. 2.

FIG. 20 illustrates alternative embodiments of the example operational flow 200 of FIG. 2. FIG. 20 illustrates example embodiments where operation 230 may include at least one additional operation. Additional operations may include an operation 2002, and/or an operation 2004.

Operation 2002 illustrates selecting the at least one prescription medication at least partially based on at least one of a medication history of the at least one individual or an artificial sensory experience history of the at least one individual. For example, as shown in FIG. 1, selector module 106 may select the at least one prescription medication at Least partially based on at least one of a medication history of the at least one individual or an artificial sensory experience history of the at least one individual. In one example, selector module 106 can select a prescription medication based on a medication history of an individual named Jennifer Harris or an anonymous individual. A medication history may include any record of administered medications and/or drugs that may exist for an individual. An artificial sensory experience history may include any record of an artificial sensory experience associated with an individual. In some instances, selector module 106 may include a computer processor.

Operation 2004 illustrates selecting the at least one prescription medication at least partially based on at least one of a genetic or an epigenetic profile. For example, as shown in FIG. 1, selector module 106 may select the at least one prescription medication at least partially based on at least one of a genetic or an epigenetic profile. In one instance, selector module 106 can select a prescription medication based on a genetic profile. A genetic profile may include hereditary information encoded in the genetic sequence of an individual. An epigenetic profile may include information regarding chromatin and/or DNA modifications that are stable over rounds of cell division but do not involve changes in the underlying DNA sequence of the organism, such as histone acetylation and/or DNA methylation. Other epigenetic information may be found in higher-order chromatin structure. In some instances, selector module 106 may include a computer processor.

Figure 21:
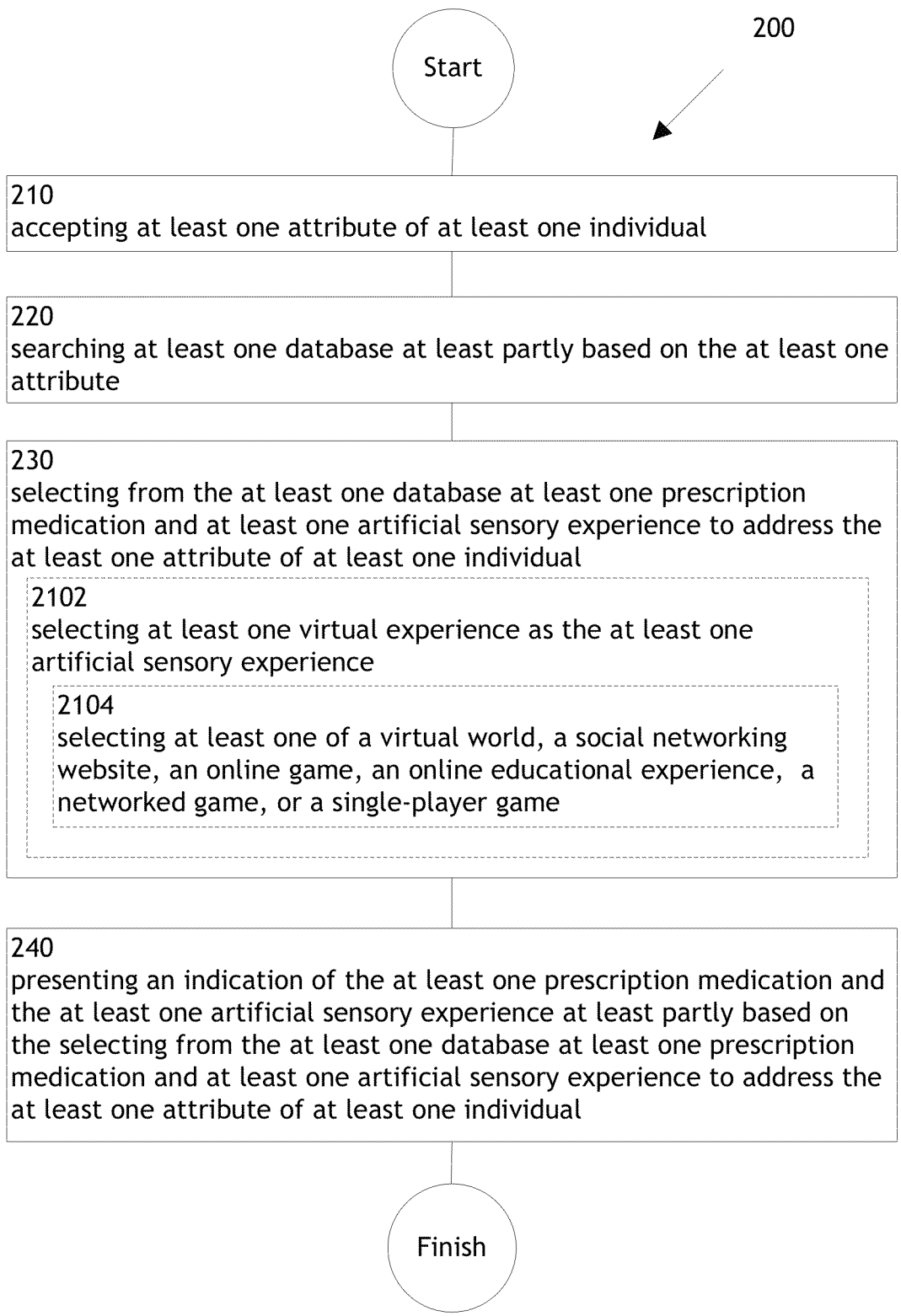
FIG. 21 illustrates an alternative embodiment of the operational flow of FIG. 2.

FIG. 21 illustrates alternative embodiments of the example operational flow 200 of FIG. 2. FIG. 21 illustrates example embodiments where operation 230 may include at Least one additional operation. Additional operations may include an operation 2102, and/or an operation 2104.

Operation 2102 illustrates selecting at Least one virtual experience as the at least one artificial sensory experience. For example, as shown in FIG. 1, selector module 106 may select at least one virtual experience as the at Least one artificial sensory experience. In one example, selector module 106 can select a virtual experience as the artificial sensory experience. A virtual experience may include an experience with a computer-simulated environment. Such a virtual experience may be interactive or non-interactive. Some examples of a virtual experience may include an experience with a virtual world, a simulated reality, a computer game, and/or a virtual tour, and may involve input devices such as a keyboard, a mouse, an accelerometer-containing input device, and/or a wired glove. A virtual experience may also involve a visual and/or auditory monitoring device such as a video monitor, goggles, loudspeakers, or the like. Examples of a virtual experience include second life, snow world, or the Like. In some instances, selector module 106 may include a computer processor.

Operation 2104 illustrates selecting at Least one of a virtual world, a social networking website, an online game, an online educational experience, a networked game, or a single-player game. For example, as shown in FIG. 1, selector module 106 may select at least one of a virtual world, a social networking website, an online game, an online educational experience, a networked game, or a single-player game. In one instance, selector module 106 can select a virtual world. A virtual world may include a computer-based simulated environment intended for its users to inhabit and interact via avatars, such as second life. A social networking website may include a website for observing and/or interacting with one or more personal and/or professional relationships between individuals. Some examples of a social networking website may include MySpace, GeoCities, Facebook, and/or LinkedIn. In one instance, selector module 106 may select Facebook as the social networking website and may include directions to Facebook to implement a color scheme including bright colors, such as yellow and light blue, for preventing the onset of depression in a depression prone viewer. An online game may include a game played over a network, such as hardwired terminals, a wireless network, a modem network, a video console, and/or the Internet. Some online games may include virtual worlds and/or virtual communities. Examples of online games may include World of Warcraft (WoW), Final Fantasy XI, Lineage II, Guild Wars, and/or RuneScape. An online educational experience may include a tutorial, a lesson, and/or an online class. Some examples of an online educational experience may include a HTML tutorial, an online piano lesson, and/or an online degree program from the University of Phoenix. A networked game may include any game played by more than one player and may be played on a computer. An example of a networked game may include World of Warcraft (WoW). A single-player game may include any game that can be played by one player and that may or may not be played on a computer. Examples of a single-player game includes solitaire, puzzle games such as Tetris, Call of Duty, and Guitar Hero. In some instances, selector module 106 may include a computer processor.

Figure 22:
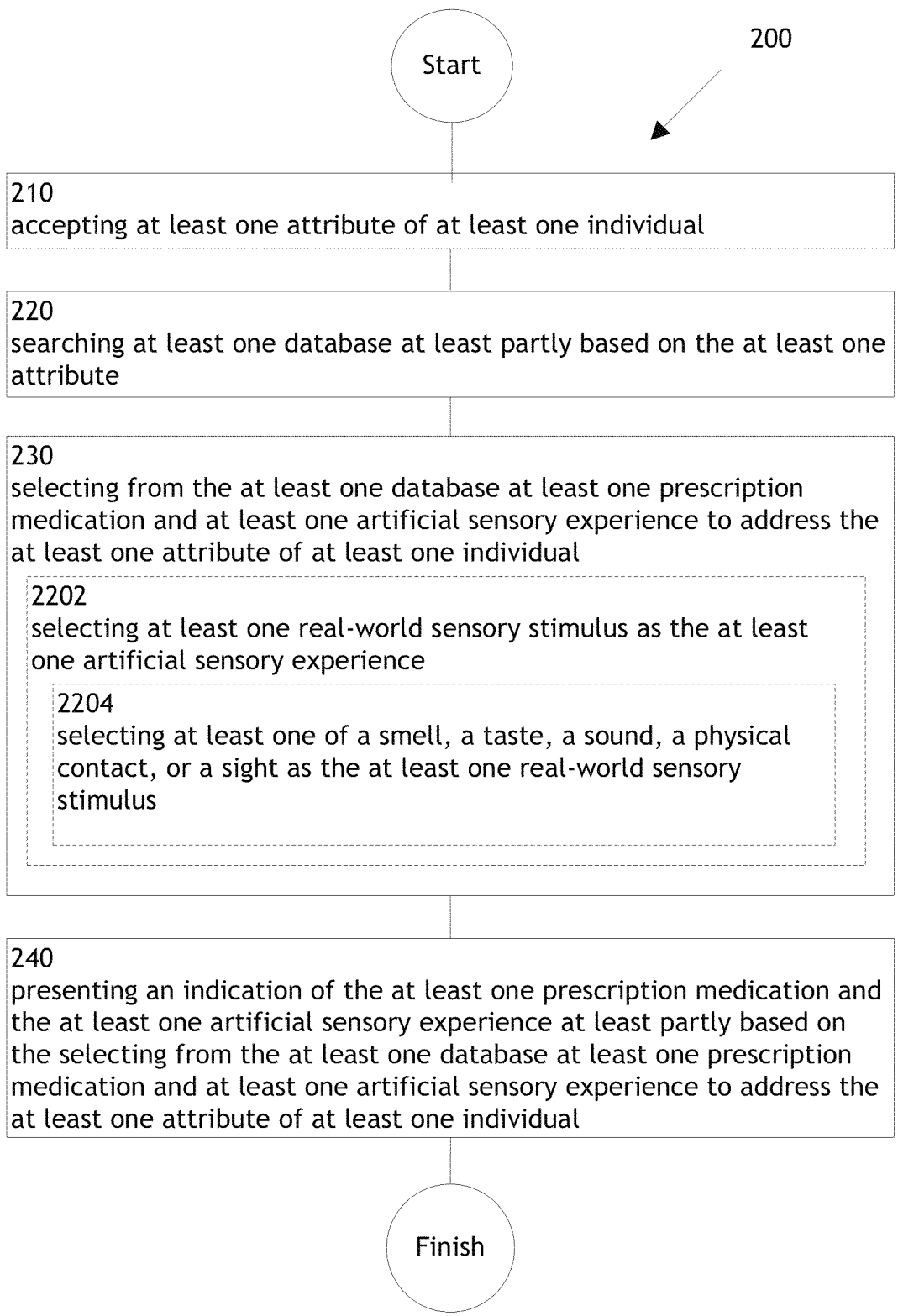
FIG. 22 illustrates an alternative embodiment of the operational flow of FIG. 2.

FIG. 22 illustrates alternative embodiments of the example operational flow 200 of FIG. 2. FIG. 22 illustrates example embodiments where operation 230 may include at least one additional operation. Additional operations may include an operation 2202, and/or an operation 2204.

Operation 2202 illustrates selecting at least one real-world sensory stimulus as the at least one artificial sensory experience. For example, as shown in FIG. 1, selector module 106 may select at least one real-world sensory stimulus as the at least one artificial sensory experience. In one instance, selector module 106 can select a real-world sensory stimulus including an aroma as an artificial sensory experience. Some examples of a real-world sensory stimulus may include aromas and/or smelts, sounds, sights, touch, pressure, temperature and/or heat, and/or vibration. In some instances, selector module 106 may include a computer processor. Further, operation 2204 illustrates selecting at least one of a smell, a taste, a sound, a physical contact, or a sight as the at least one real-world sensory stimulus. For example, as shown in FIG. 1, selector module 106 may select at least one of a smelt, a taste, a sound, a physical contact, or a sight as the at least one real-world sensory stimulus. In one example, selector module 106 selects a smell and a taste as a real-world sensory stimulus. A smell may include any property detected by the nose and/or olfactory system. A taste may include any flavor and/or property detected by the tongue and/or taste buds. A sound may include any sound wave that may be detected by the eardrum. A physical contact may include anything related to touch, feet, and/or detection by the skin and/or body, and/or physical activity including exercise. In one instance, selector module 106 may select a physical contact including physical exercise associated with participating in playing a tennis game on a Nintendo Wii video game console, for example. A sight may include any image, and/or light detected by the eyes. In some instances, selector module 106 may include a computer processor.

Figure 23:
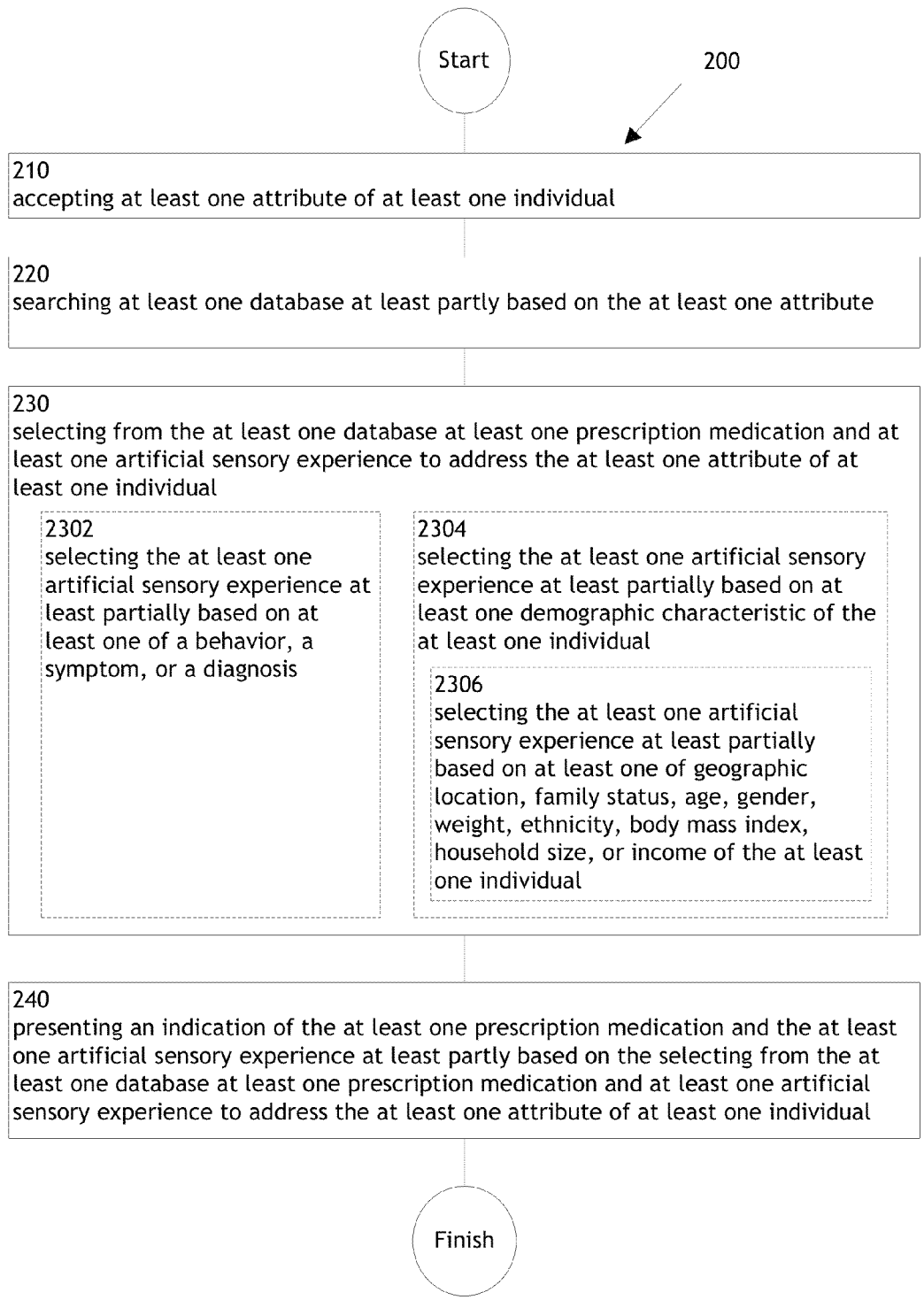
FIG. 23 illustrates an alternative embodiment of the operational flow of FIG. 2.

FIG. 23 illustrates alternative embodiments of the example operational flow 200 of FIG. 2. FIG. 23 illustrates example embodiments where operation 230 may include at least one additional operation. Additional operations may include an operation 2302, an operation 2304, and/or an operation 2306.

Operation 2302 illustrates selecting the at least one artificial sensory experience at least partially based on at least one of a behavior, a symptom, or a diagnosis. For example, as shown in FIG. 1, selector module 106 may select the at least one artificial sensory experience at Least partially based on at Least one of a behavior, a symptom, or a diagnosis. In one example, selector module 106 can select an artificial sensory experience based on behavior entered by a user 118 via a user interface 116. A behavior may include the manner in which a person and/or thing acts and/or reacts. A symptom may include a manifestation, sign, and/or an indication of the presence of a disease and/or some other disorder and/or abnormality. A diagnosis may include identifying a disease and/or condition by its signs and/or symptoms. For example, selector module 106 and/or system 100 may select an immersive virtual reality experience as the at Least one artificial sensory experience at least partially based on a pain symptom and/or a third-degree burn diagnosis. In some instances, selector module 106 may include a computer processor.

Operation 2304 illustrates selecting the at least one artificial sensory experience at least partially based on at least one demographic characteristic of the at Least one individual. For example, as shown in FIG. 1, selector module 106 may select the at least one artificial sensory experience at least partially based on at least one demographic characteristic of the at least one individual. In one example, selector module 106 can select an artificial sensory experience based on a demographic characteristic the at Least one individual. A demographic characteristic may include a socioeconomic, age, gender, and/or other similar factor defining a certain population. For example, selector module 106 and/or system 100 may select a virtual reality experience such as a Sesame Street or Disney-themed experience as the at least one artificial sensory experience at least partially based on an indication that the individual is aged 6-10 years old. In some instances, selector module 106 may include a computer processor.

Further, operation 2306 illustrates selecting the at Least one artificial sensory experience at least partially based on at least one of geographic location, family status, age, gender, weight, ethnicity, body mass index, household size, or income of the at least one individual. For example, as shown in FIG. 1, selector module 106 may select the at Least one artificial sensory experience at Least partially based on at least one of geographic location, family status, age, gender, weight, ethnicity, body mass index, household size, or income of the at least one individual. In one example, selector module 106 can select the artificial sensory experience based on an age and a weight associated with the at least one individual. A geographic Location may include a location where an individual currently resides, has resided in the past, and/or has visited. A family status may include marital status, status and/or presence of children, and/or the status and/or health of extended family. In some instances, selector module 106 may include a computer processor.

Figure 24:
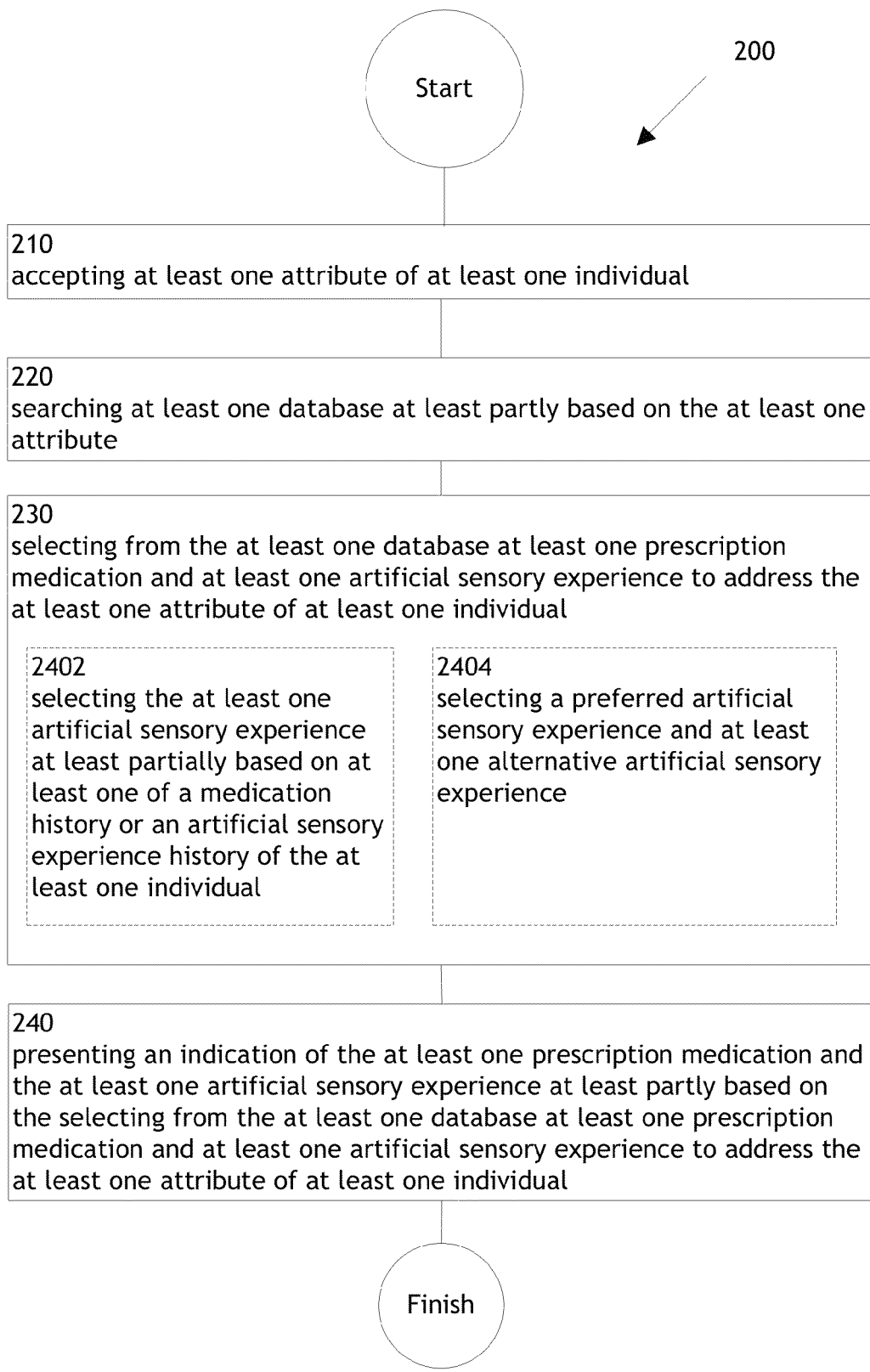
FIG. 24 illustrates an alternative embodiment of the operational flow of FIG. 2.

FIG. 24 illustrates alternative embodiments of the example operational flow 200 of FIG. 2. FIG. 24 illustrates example embodiments where operation 230 may include at least one additional operation. Additional operations may include an operation 2402, and/or an operation 2404.

Operation 2402 illustrates selecting the at least one artificial sensory experience at Least partially based on at least one of a medication history or an artificial sensory experience history of the at least one individual. For example, as shown in FIG. 1, selector module 106 may select the at least one artificial sensory experience at Least partially based on at least one of a medication history or an artificial sensory experience history of the at least one individual. In one instance, selector module 106 can select an artificial sensory experience based on an artificial sensory experience history of the at least one individual. An artificial sensory experience history may include any record of at least one administered artificial sensory experience history. For example, system 100 and/or selector module 106 may select a modified facebook webpage having a cheerful color scheme at least partly based on a facebook usage history for an individual with signs of depression. In some instances, selector module 106 may include a computer processor.

Operation 2404 illustrates selecting a preferred artificial sensory experience and at least one alternative artificial sensory experience. For example, as shown in FIG. 1, selector module 106 may select a preferred artificial sensory experience and at Least one alternative artificial sensory experience. In one example, selector module 106 can select a preferred artificial sensory experience and at least one alternative artificial sensory experience. A preferred artificial sensory experience may include a more desirable artificial sensory experience due to a lack of and/or a reduced level of side effects, reduced impact upon the individual, and/or increased compatibility with another medications and/or treatment. An alternative artificial sensory experience may include any artificial sensory experience in addition to the preferred artificial sensory experience and may be less desirable than the preferred artificial sensory experience due to side effects and/or increased impact upon the individual. In some instances, selector module 106 may include a computer processor.

Figure 25:
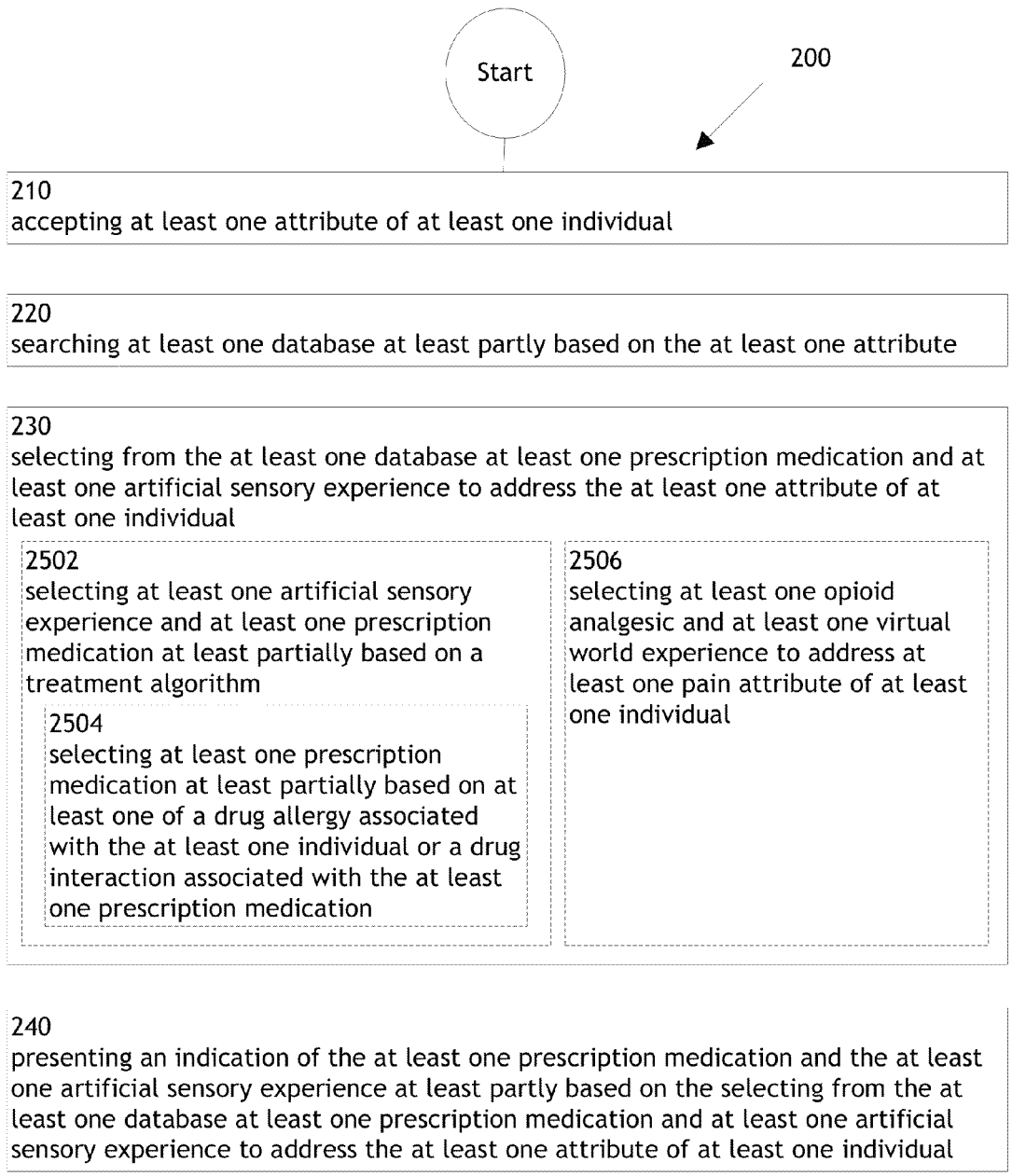
FIG. 25 illustrates an alternative embodiment of the operational flow of FIG. 2.

FIG. 25 illustrates alternative embodiments of the example operational flow 200 of FIG. 2. FIG. 25 illustrates example embodiments where operation 230 may include at least one additional operation. Additional operations may include an operation 2502, an operation 2504, and/or an operation 2506.

Operation 2502 illustrates selecting at least one artificial sensory experience and at least one prescription medication at least partially based on a treatment algorithm. For example, as shown in FIG. 1, selector module 106 may select at least one artificial sensory experience and at least one prescription medication at least partially based on a treatment algorithm. In one instance, selector module 106 can select an artificial sensory experience and a prescription medication based on a computer software treatment algorithm. A treatment algorithm may include any computation, formula, statistical survey, and/or look-up table for determining and/or selecting a suitable artificial sensory experience and prescription medication combination. Some examples may include a computer software algorithm, a calculator, a flowchart, and/or a decision tree. For example, system 100 and/or selector module 106 may, based on an accepted pain symptom of an individual, access a lookup chart that matches the pain symptom with a pain medication, such as naproxen, and a virtual experience, such as World of Warcraft. Such a combination therapy may be particularly effective in ameliorating the pain symptom in the individual. In some instances, selector module 106 may include a computer processor.

Further, operation 2504 illustrates selecting at least one prescription medication at least partially based on at least one of a drug allergy associated with the at least one individual or a drug interaction associated with the at least one prescription medication. For example, as shown in FIG. 1, selector module 106 may select at least one prescription medication at least partially based on at Least one of a drug allergy associated with the at least one individual or a drug interaction associated with the at least one prescription medication. In one example, selector module 106 can select a prescription medication based on a drug allergy associated with the at least one individual. A drug allergy may include any allergy to a drug and/or drug intolerance. Some examples of a drug allergy may include penicillin allergies, codeine allergies, and/or allergies to a dye in a drug. A drug interaction may include an undesirable and/or unwanted reaction between two or more drugs and/or medications. For example, the system 100 and/or selector module 106 can select a prescription medication other than those that might cause a side effect in an individual, perhaps because of a known predisposition to the side effect (e.g., an allergy) or because of a known drug-drug interaction relevant to the individual based on the individual's medication regimen. In this way, risk of side effects can be lessened. In some instances, selector module 106 may include a computer processor.

Operation 2506 illustrates selecting at least one ° plaid analgesic and at least one virtual world experience to address at Least one pain attribute of at Least one individual. For example, as shown in FIG. 1, selector module 106 may select from a prescription medication database at Least one opioid analgesic and at Least one virtual world experience to address at least one pain attribute of at least one individual. In one example, selector module 106 can select an opioid analgesic including morphine and a virtual world experience including an online game to address a pain attribute of at least one individual named Mary Andersen. In some instances, selector module 106 may include a computer processor.

Figure 26:
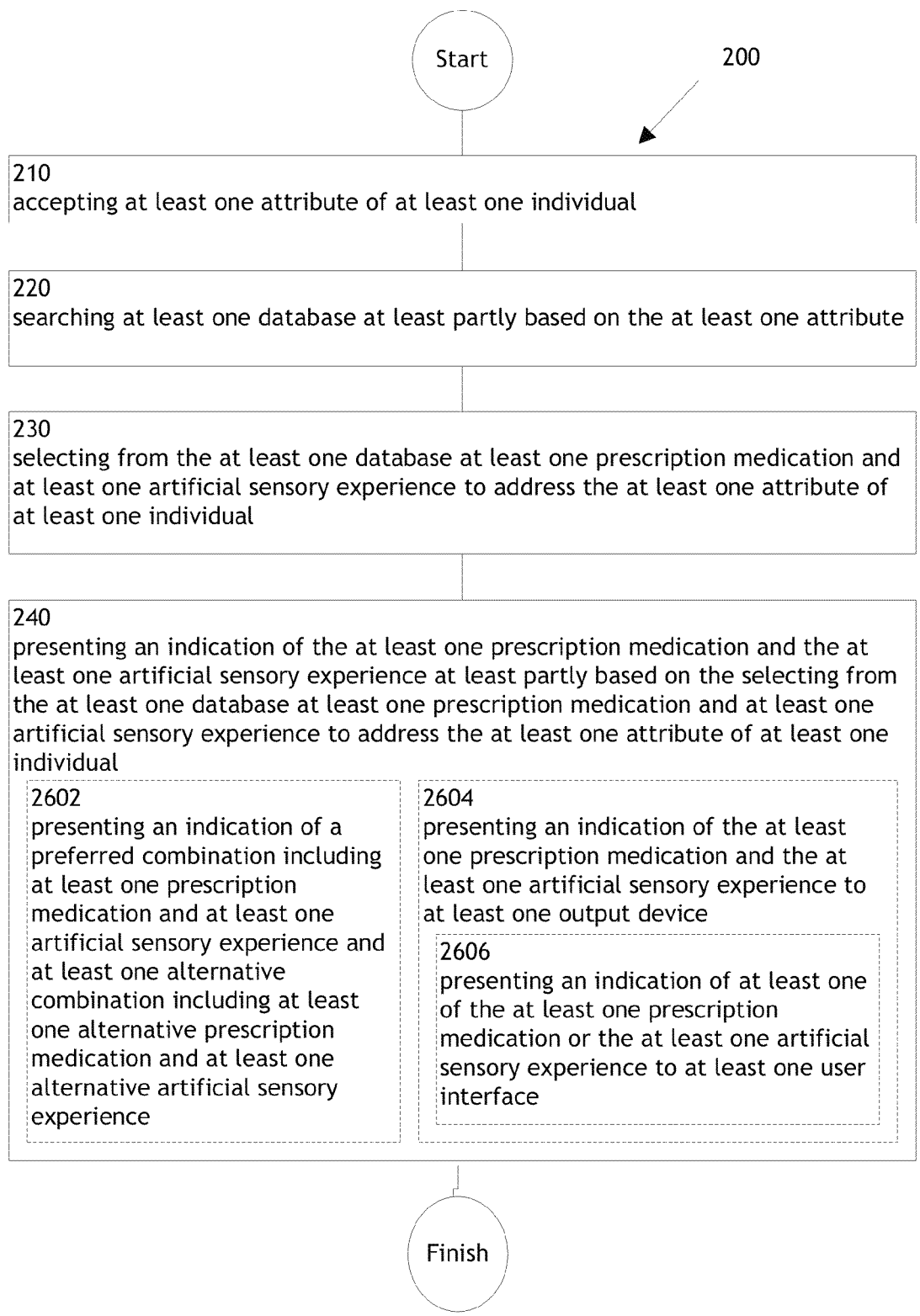
FIG. 26 illustrates an alternative embodiment of the operational flow of FIG. 2.

FIG. 26 illustrates alternative embodiments of the example operational flow 200 of FIG. 2. FIG. 26 illustrates example embodiments where operation 240 may include at Least one additional operation. Additional operations may include an operation 2602, an operation 2604, and/or an operation 2606.

Operation 2602 illustrates presenting an indication of a preferred combination including at least one prescription medication and at least one artificial sensory experience and at least one alternative combination including at least one alternative prescription medication and at least one alternative artificial sensory experience. For example, as shown in FIG. 1, presenter module 108 may present an indication of a preferred combination including at least one prescription medication and at least one artificial sensory experience and at Least one alternative combination including at least one alternative prescription medication and at least one alternative artificial sensory experience. In one instance, presenter module 108 can present an indication of a preferred combination to an individual 134 including a prescription medication and an artificial sensory experience along with an alternative combination including an alternative prescription medication and an alternative artificial sensory experience. Individual 134 may include a single individual, multiple individuals, and/or an entity. A preferred combination may include a more desirable combination due to a lack of and/or a reduced number of and/or level of side effects, reduced impact upon the administered individual, and/or increased compatibility with another medications and/or treatment. An alternative combination may include any combination in addition to the preferred combination and may be ostensibly less desirable than the preferred artificial sensory experience because of a potential side effect and/or impact upon the administered individual. Presentation of alternative combinations may provide benefits to the individual in terms of accessibility, affordability, and/or personal preference of medication and/or artificial sensory experience. In some instances, presenter module 108 may include a computer processor.

Operation 2604 illustrates presenting an indication of the at least one prescription medication and the at least one artificial sensory experience to at least one output device. For example, as shown in FIG. 1, presenter module 108 may present an indication of the at least one prescription medication and the at least one artificial sensory experience to at least one output device. In one example, presenter module 108 can present an indication of a prescription medication and an artificial sensory experience to an output device 130 including a printer at a health clinic. An output device may include any hardware device configured for receiving computer output. Some examples of an output device may include a printer, a monitor, a mobile phone, a speaker, and/or a visual display unit. The output device may be used by individual 134. In some instances, presenter module 108 may include a computer processor.

Further, operation 2606 illustrates presenting an indication of at Least one of the at least one prescription medication or the at least one artificial sensory experience to at least one user interface. For example, as shown in FIG. 1, presenter module 108 may present an indication of at least one of the at least one prescription medication or the at least one artificial sensory experience to at least one user interface. In one instance, presenter module 108 can present an indication of a prescription medication and an artificial sensory experience to a user interface. A user interface may include means by which an individual may interact with a system. Some examples of a user interface may include a touchscreen, a graphical user interface, a tactile interface, and/or a Live user interface, in some instances, presenter module 108 may include a computer processor.

Figure 27:
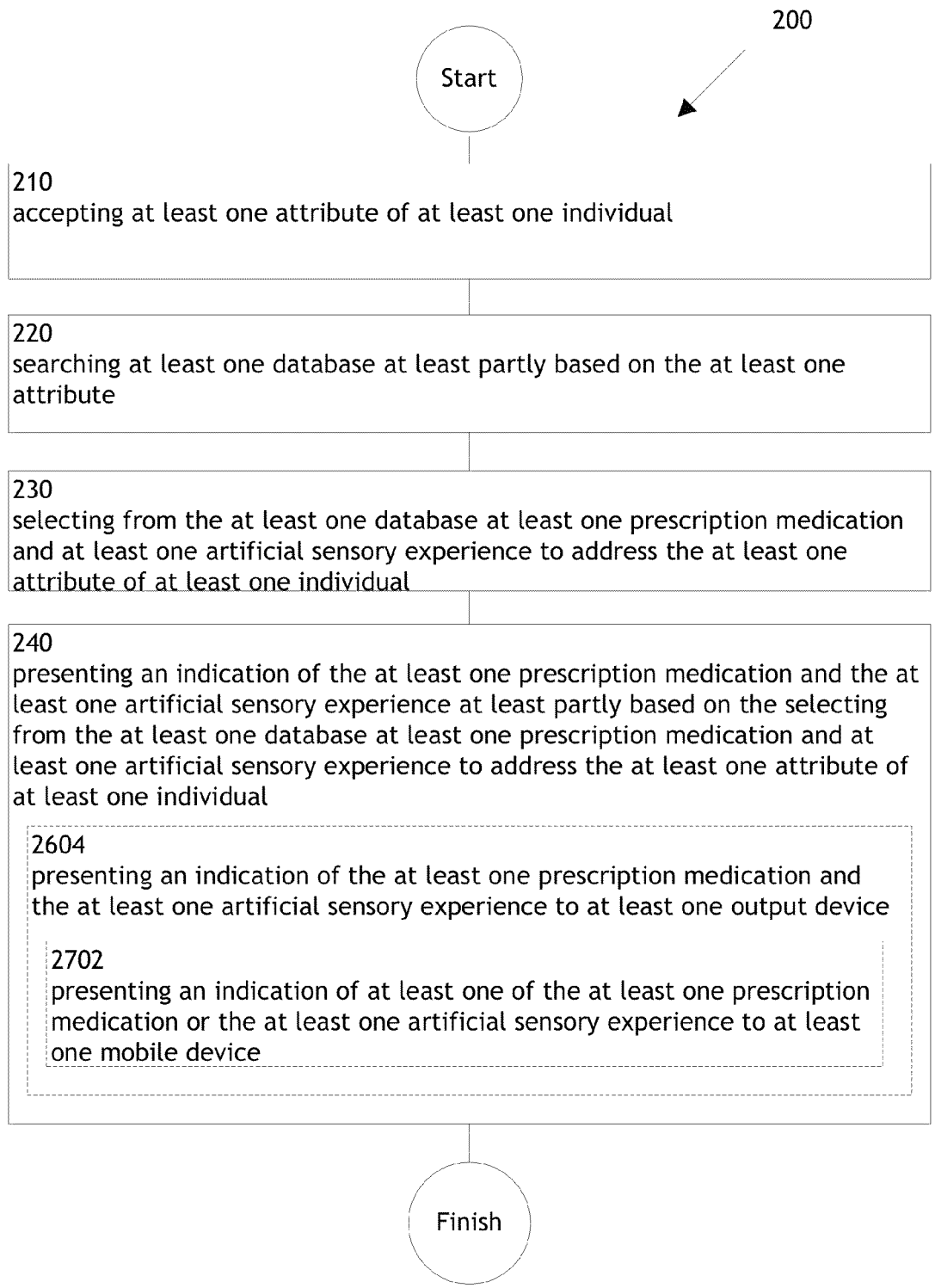
FIG. 27 illustrates an alternative embodiment of the operational flow of FIG. 2.

FIG. 27 illustrates alternative embodiments of the example operational flow 200 of FIG. 2. FIG. 27 illustrates example embodiments where operation 240 may include at least one additional operation. Additional operations may include an operation 2702. Further, operation 2702 illustrates presenting an indication of at Least one of the at Least one prescription medication or the at least one artificial sensory experience to at Least one mobile device. For example, as shown in FIG. 1, presenter module 108 may present an indication of at (east one of the at least one prescription medication or the at Least one artificial sensory experience to at least one mobile device. In one instance, presenter module 108 can present an indication of a prescription medication to a mobile device 132. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager, in some instances, presenter module 108 may include a computer processor.

Figure 28:
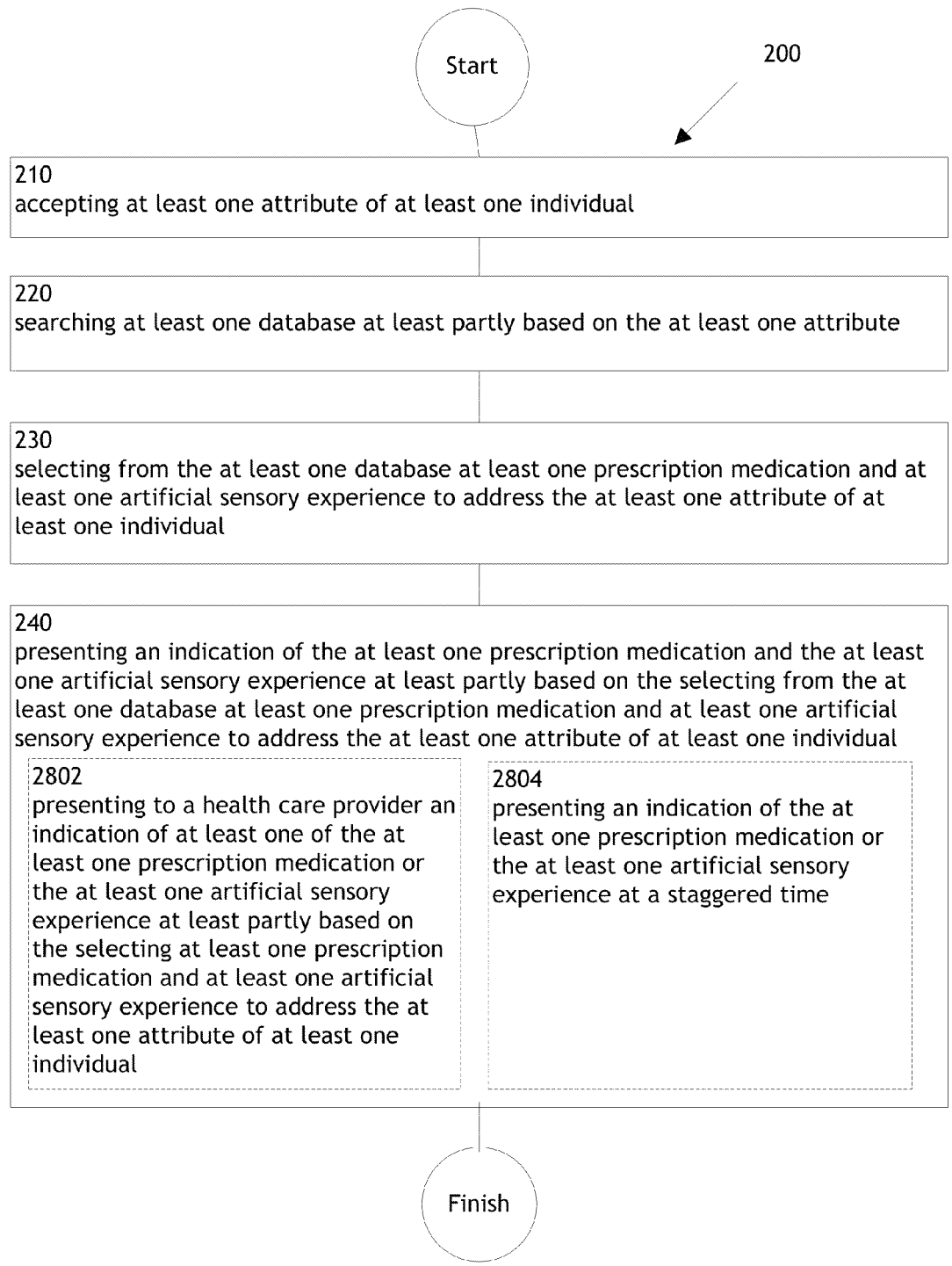
FIG. 28 illustrates an alternative embodiment of the operational flow of FIG. 2.

FIG. 28 illustrates alternative embodiments of the example operational flow 200 of FIG. 2. FIG. 28 illustrates example embodiments where operation 240 may include at Least one additional operation. Additional operations may include an operation 2802, and/or an operation 2804.

Operation 2802 illustrates presenting to a health care provider an indication of at Least one of the at least one prescription medication or the at (east one artificial sensory experience at Least partly based on the selecting at Least one prescription medication and at Least one artificial sensory experience to address the at least one attribute of at least one individual. For example, as shown in FIG. 1, presenter module 108 may present to a health care provider an indication of at Least one of the at least one prescription medication or the at least one artificial sensory experience at least partly based on the selecting at least one prescription medication and at least one artificial sensory experience to address an attribute of an individual. In one example, presenter module 108 can present to a health care provider 128 an indication of a prescription medication based on the selecting at least one prescription medication and at least one artificial sensory experience to address the at least one attribute 120 of at least one individual. A health care provider may include a pharmacy, a pharmaceutical company, a medical device company, a research institution, a computer software and/or computer hardware company, a website, a nurse and/or a physician. In some instances, presenter module 108 may include a computer processor.

Operation 2804 illustrates presenting an indication of the at least one prescription medication or the at least one artificial sensory experience at a staggered time. For example, as shown in FIG. 1, presenter module 108 may present an indication of at least one of the at least one prescription medication or the at least one artificial sensory experience at a staggered time. In one example, presenter module 108 can present an indication of a series of prescription medications and an artificial sensory experience at staggered times. A staggered time may include presenting an indication of the at least one drug and/or artificial sensory experience at overlapping times and/or at different times, including alternating times. For example, at least one drug and an artificial sensory experience may be administered at an initial time and the same or a different drug may be administered when the first-administered at Least one drug is at its peak effect. In another example, at least one drug and an artificial sensory experience may be administered at an initial time and the same or a different drug may be administered when the first administered at least one drug is at its lowest effect. In another example, an artificial sensory experience may be administered at an initial time and at least one prescription medication at a later time. The at least one artificial sensory experience and/or the at Least one prescription medication may be administered at any number of times either concurrently, partially concurrently, or not concurrently. In some instances, presenter module 108 may include a computer processor.

Figure 29:
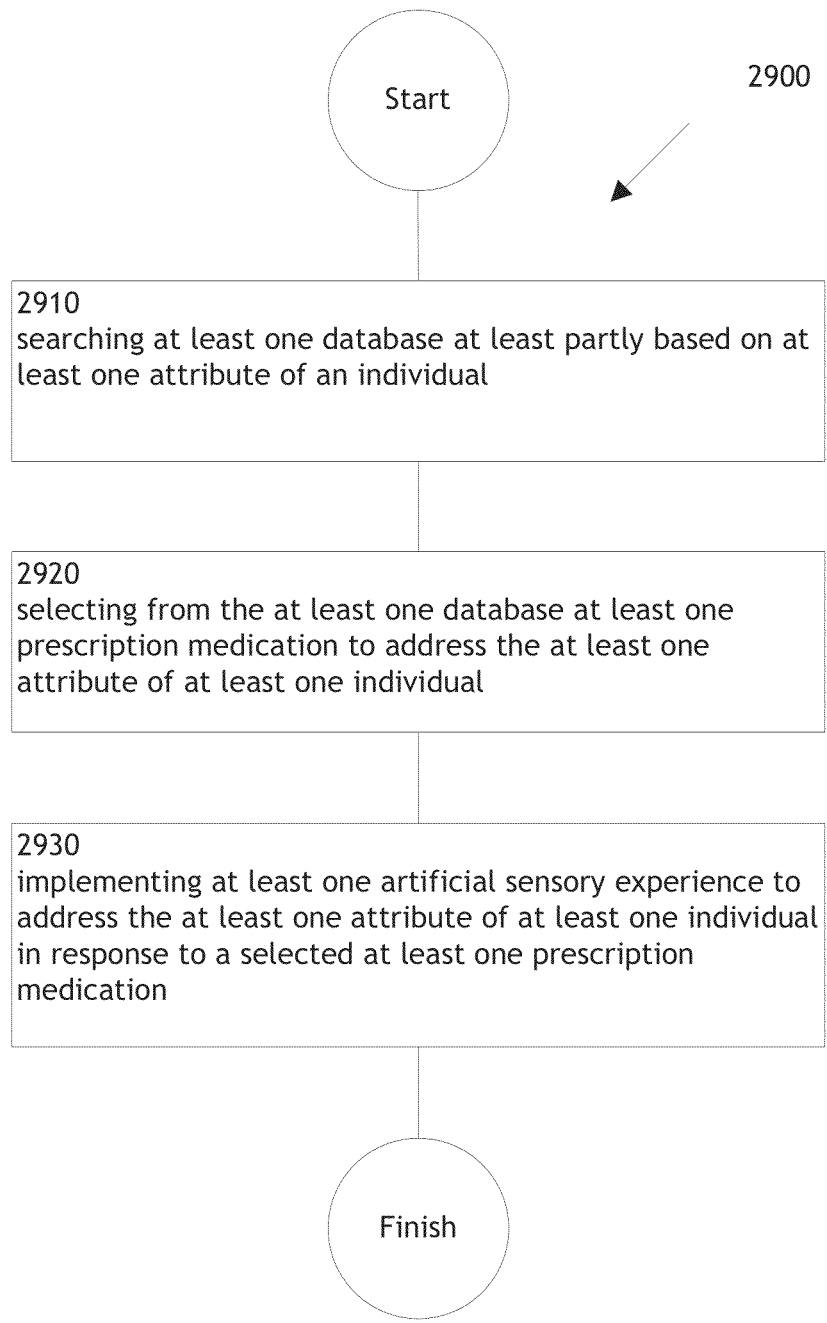
FIG. 29 illustrates an operational flow representing example operations related to selecting a combination of at least one prescription medication and at Least one artificial sensory experience.

FIG. 29 illustrates an operational flow 2900 representing example operations related to querying at least one database at least partly based on at least one attribute of an individual, selecting from the at least one database at Least one prescription medication to address the at least one attribute of at Least one individual, and/or implementing at least one artificial sensory experience to address the at least one attribute of at least one individual in response to a selected at least one prescription medication. In FIG. 29, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 2900 moves to an operation 2910. Operation 2910 depicts querying at least one database at Least partly based on at least one attribute of an individual. For example, as shown in FIG. 1, querier module 104 may search at Least one database at least partly based on at least one attribute of an individual. In one instance, querier module 104 may search medication database 124 and artificial sensory experience database 126 based on an attribute 120 including an indication of hypertension associated with an individual named John Smith. In some instances, querier module 104 may include a computer processor.

Then, operation 2920 depicts selecting from the at least one database at least one prescription medication to address the at least one attribute of at least one individual. For example, as shown in FIG. 1, selector module 106 may select from the at Least one database at Least one prescription medication to address the at least one attribute of at Least one individual. In one example and continuing with the previous example, selector module 106 may select from medication database 124 and artificial sensory experience database 126 a prescription medicine for addressing the attribute 120 including an indication of hypertension associated with an individual named John Smith. In some instances, selector module 106 may include a computer processor.

Then, operation 2930 depicts implementing at Least one artificial sensory experience to address the at least one attribute of at Least one individual in response to a selected at least one prescription medication. For example, as shown in FIG. 1, implementer module 138 may implement at least one artificial sensory experience to address the at Least one attribute of at Least one individual in response to a selected at least one prescription medication. In one instance and continuing with the previous example, implementer module 106 may implement an artificial sensory experience including a virtual world for addressing the attribute 120 including an indication of hypertension associated with an individual named John Smith in response to a selected prescription medication from a medication database 124. In some instances, selector module 106 may include a computer processor.

Figure 30:
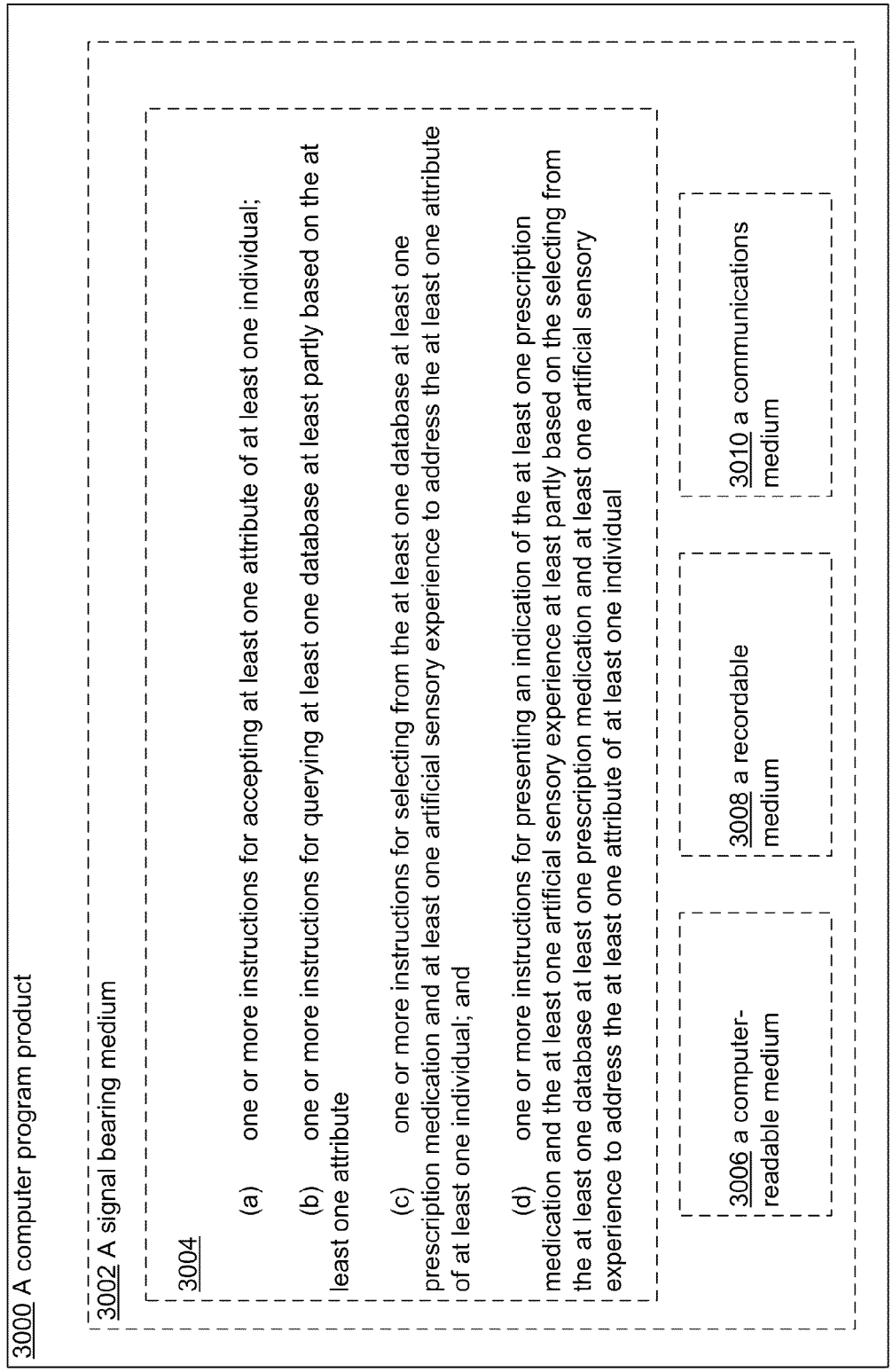
FIG. 30 illustrates a computer program product related to selecting a combination of at Least one prescription medication and at least one artificial sensory experience.

FIG. 30 illustrates a partial view of an example computer program product 3000 that includes a computer program 3004 for executing a computer process on a computing device. An embodiment of the example computer program product 3000 is provided using a signal-bearing medium 3002, and may include one or more instructions for accepting at (east one attribute of at least one individual; one or more instructions for querying at least one database at least partly based on the at least one attribute; one or more instructions for selecting from the at least one database at least one prescription medication and at least one artificial sensory experience to address the at least one attribute of at least one individual; and one or more instructions for presenting an indication of the at (east one prescription medication and the at Least one artificial sensory experience at Least partly based on the selecting from the at least one database at least one prescription medication and at Least one artificial sensory experience to address the at Least one attribute of at least one individual. The one or more instructions may be, for example, computer executable and/or Logic-implemented instructions. In one implementation, the signal-bearing medium 3002 may include a computer-readable medium 3006. In one implementation, the signal bearing medium 3002 may include a recordable medium 3008. In one implementation, the signal bearing medium 3002 may include a communications medium 3010.

Figure 31:
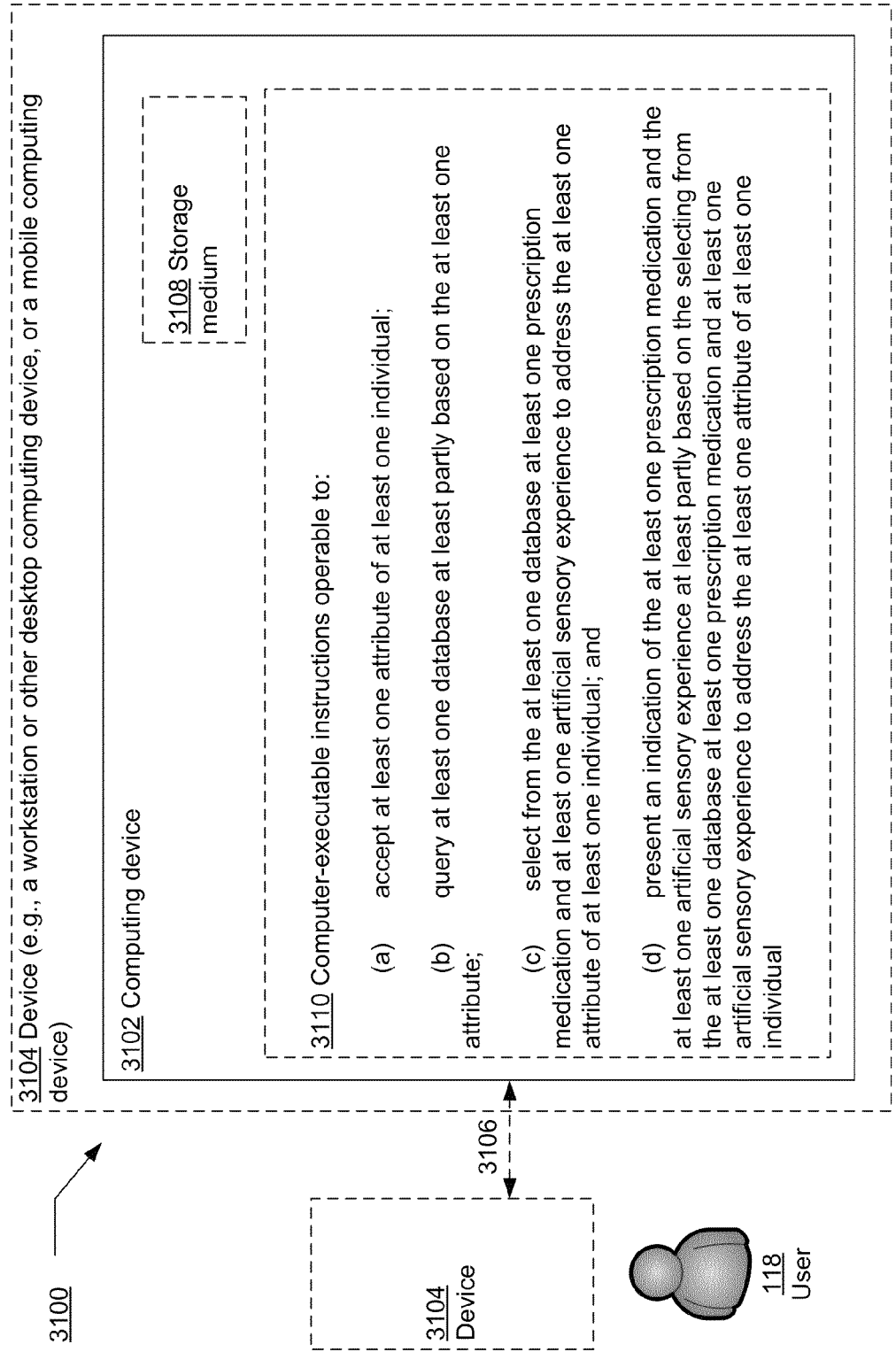
FIG. 31 illustrates a system related to selecting a combination of at least one prescription medication and at least one artificial sensory experience.

FIG. 31 illustrates an example system 3100 in which embodiments may be implemented. The system 3100 includes a computing system environment. The system 3100 also illustrates the user 118 using a device 3104, which is optionally shown as being in communication with a computing device 3102 by way of an optional coupling 3106. The optional coupling 3106 may represent a local, wide-area, or peer-to-peer network, or may represent a bus that is internal to a computing device (e.g., in example embodiments in which the computing device 3102 is contained in whole or in part within the device 3104). A storage medium 3108 may be any computer storage media.

The computing device 3102 includes computer-executable instructions 3110 that when executed on the computing device 3102 cause the computing device 3102 to accept at least one attribute of at least one individual; query at least one database at least partly based on the at least one attribute; select from the at least one database at least one prescription medication and at Least one artificial sensory experience to address the at least one attribute of at least one individual; and present an indication of the at least one prescription medication and the at least one artificial sensory experience at least partly based on the selecting from the at least one database at Least one prescription medication and at Least one artificial sensory experience to address the at least one attribute of at Least one individual. As referenced above and as shown in FIG. 31, in some examples, the computing device 3102 may optionally be contained in whole or in part within the device 3104.

In FIG. 31, then, the system 3100 includes at least one computing device (e.g., 3102 and/or 3104). The computer-executable instructions 3110 may be executed on one or more of the at least one computing device. For example, the computing device 3102 may implement the computer-executable instructions 3110 and output a result to (and/or receive data from) the computing device 3104. Since the computing device 3102 may be wholly or partially contained within the computing device 3104, the device 3104 also may be said to execute some or all of the computer-executable instructions 3110, in order to be caused to perform or implement, for example, various ones of the techniques described herein, or other techniques.

The device 3104 may include, for example, a portable computing device, workstation, or desktop computing device. In another example embodiment, the computing device 3102 is operable to communicate with the device 3104 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Figure 32:
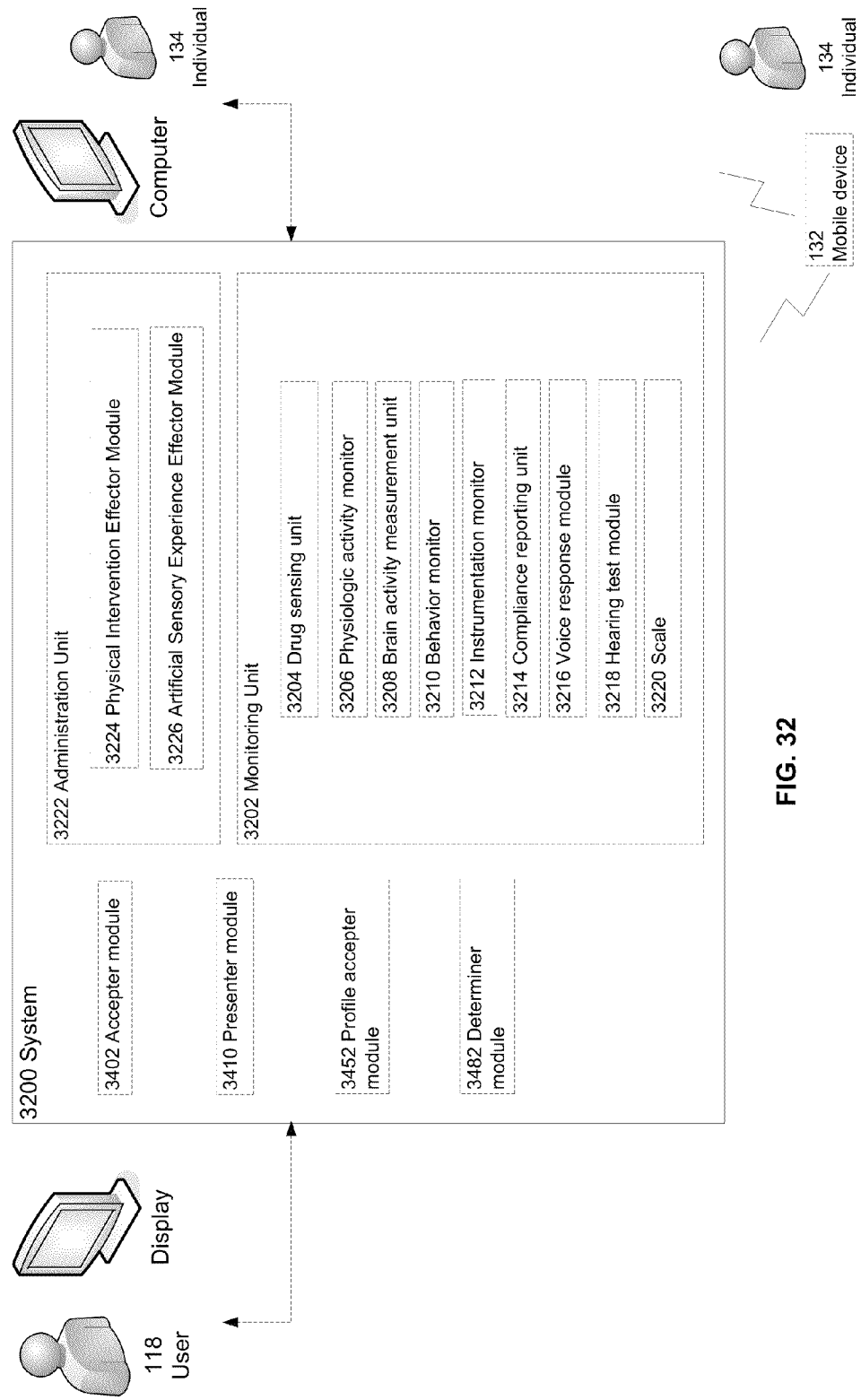
FIG. 32 illustrates an exemplary environment in which one or more technologies may be implemented.

FIG. 32 illustrates system 3200 for accepting an indication of a schedule for administration of a bioactive agent to an individual, presenting an indication of an artificial sensory experience at Least partly based on the accepting an indication of the schedule for administration of the bioactive agent to the individual, and/or accepting an indication of at least one of a pharmacokinetic or pharmacodynamic profile of a bioactive agent. The system 3200 may include accepter module 3402, presenter module 3410, profile accepter module 3452, monitoring unit 3202, determiner module 3482, and/or administration unit 3222. Administration unit 3222 may include physical intervention effector module 3224 and/or artificial sensory experience effector module 3226. Monitoring unit 3202 may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Additionally, system 3200 may include mobile device 132.

Figure 33:
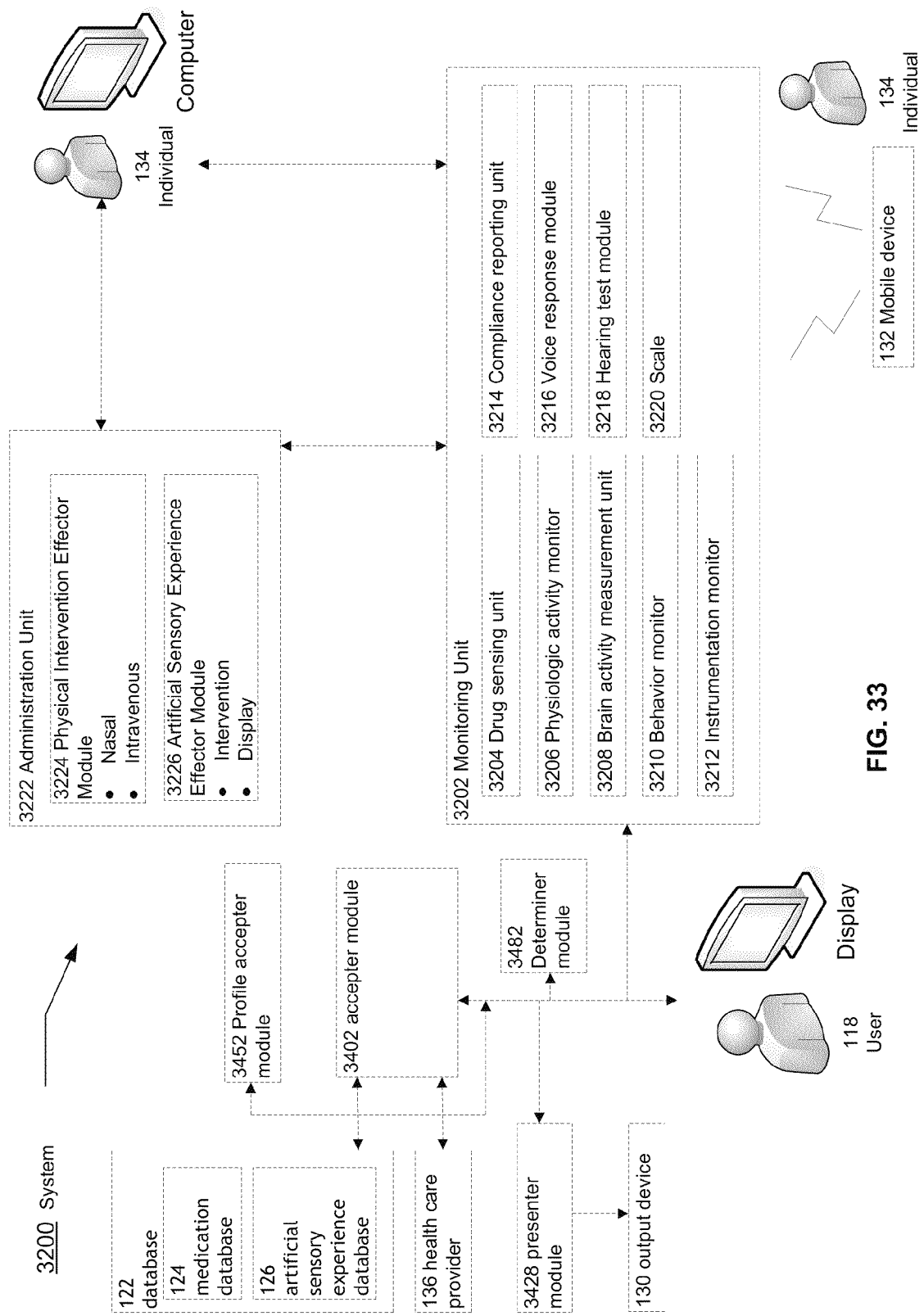
FIG. 33 illustrates an exemplary environment in which one or more technologies may be implemented.

FIG. 33 illustrates system 3200 for accepting an indication of a schedule for administration of a bioactive agent to an individual, presenting an indication of an artificial sensory experience at least partly based on the accepting an indication of the schedule for administration of the bioactive agent to the individual, and/or accepting an indication of at least one of a pharmacokinetic or pharmacodynamic profile of a bioactive agent. The system 3200 may include accepter module 3402, presenter module 3410, profile accepter module 3452, determiner module 3482, monitoring unit 3202, and/or administration unit 3222. Accepter module 3402 may receive and/or transmit information and/or data to and/or from user 118, database 122, presenter module 3410, profile accepter module 3452, and/or health care provider 136. Database 122 may include medication database 124 and/or artificial sensory experience database 126. Monitoring unit 3202 may monitor individual 134 and may include drug sensing unit 3204, physiologic activity monitor 3206, brain activity measurement unit 3208, behavior monitor 3210, instrumentation monitor 3212, compliance reporting unit 3214, voice response module 3216, hearing test module 3218, and/or scale 3220. Administration unit 3222 may include physical intervention effector module 3224 and/or artificial sensory experience effector module 3226. Additionally, mobile device 132 may communicate with acceptor module 3402, presenter module 3410, profile accepter module 3452, healthcare provider 136, user 118, individual 134, monitoring unit 3202, and/or administration unit 3222.

Figure 34:
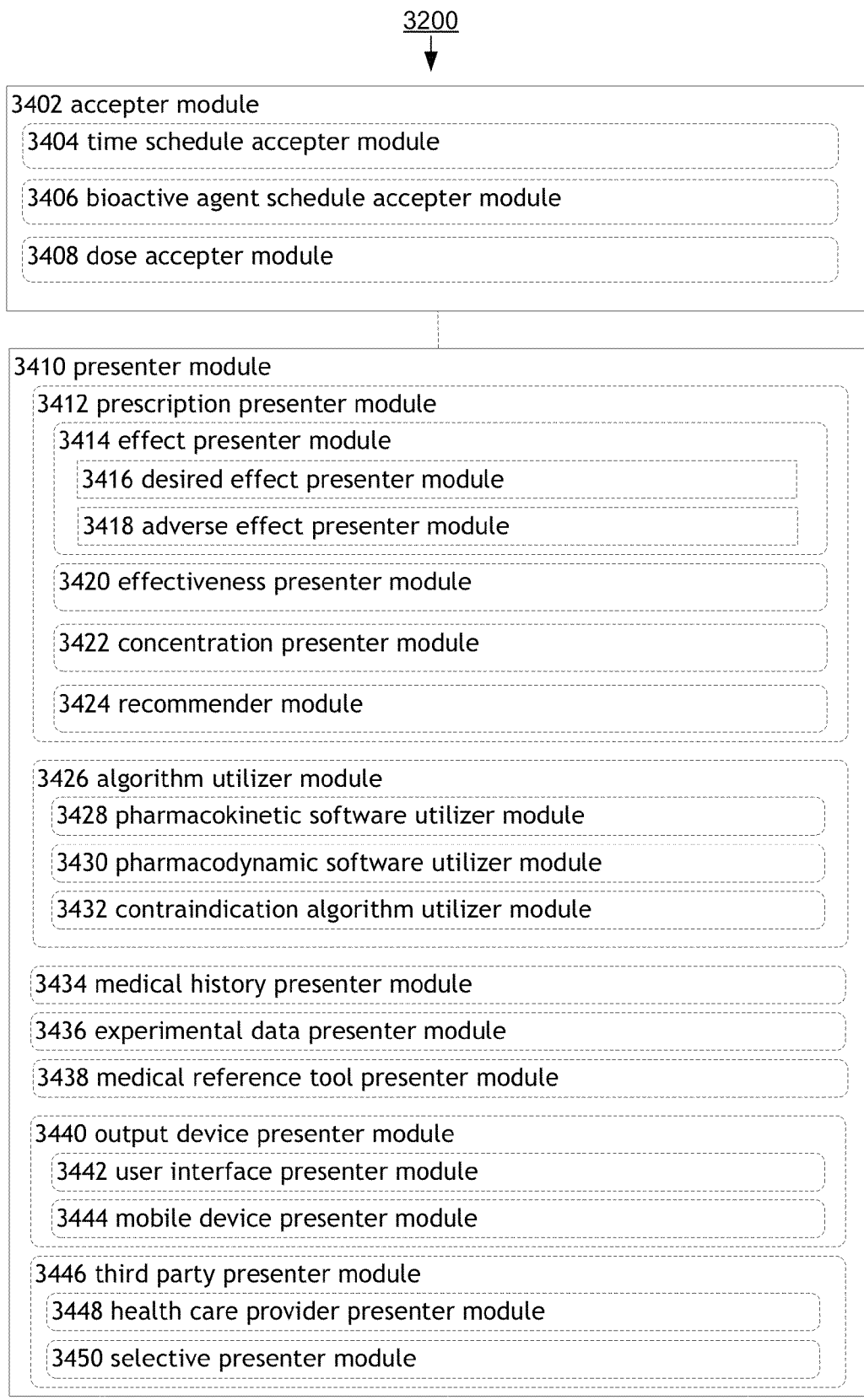
FIG. 34 illustrates an exemplary environment in which one or more technologies may be implemented.

FIG. 34 further illustrates system 3200 including accepter module 3402 and/or presenter module 3410. Accepter module 3402 may include time schedule accepter module 3404, bioactive agent schedule accepter module 3406, and/or dose accepter module 3408. Presenter module 3410 may include prescription presenter module 3412, algorithm utilizer module 3426, medical history presenter module 3434, experimental data presenter module 3436, medical reference tool presenter module 3438, output device presenter module 3440, and/or third party presenter module 3446. Prescription presenter module 3412 may include effect presenter module 3414, effectiveness presenter module 3420, concentration presenter module 3422, and/or recommender module 3424. Effect presenter module 3414 may include desired effect presenter module 3416 and/or adverse effect presenter module 3418. Algorithm utilizer module 3426 may include pharmacokinetic software utilizer module 3428, pharmacodynamic software utilizer module 3430, and/or contraindication algorithm utilizer module 3432. Output device presenter module 3440 may include user interface presenter module 3442 and/or mobile device presenter module 3444. Third party presenter module 3446 may include health care provider presenter module 3448 and/or selective presenter module 3450.

Figure 35:
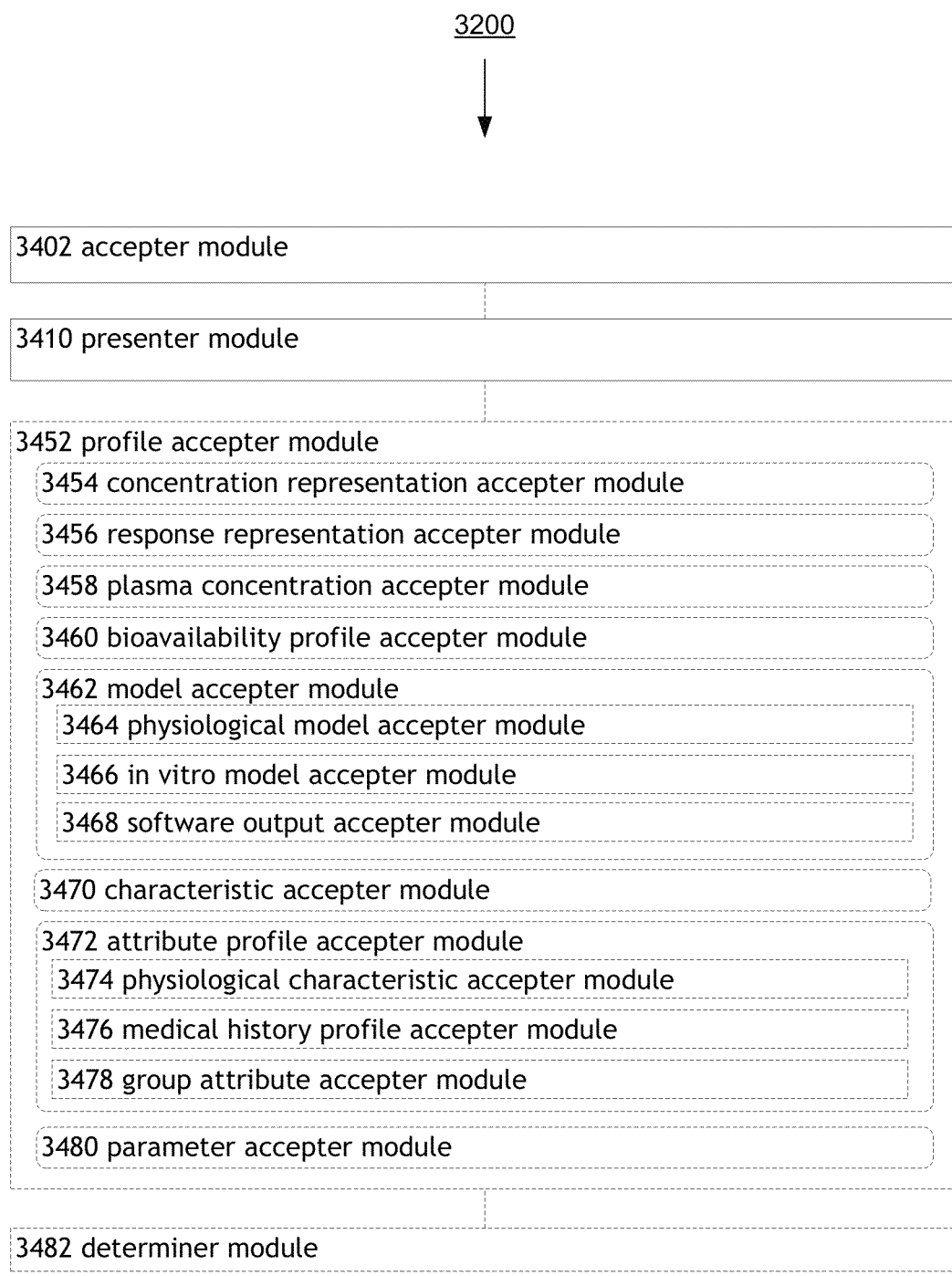
FIG. 35 illustrates an exemplary environment in which one or more technologies may be implemented.

FIG. 35 further illustrates system 3200 including accepter module 3402, presenter module 3428, profile accepter module 3452, and/or determiner module 3482. Profile accepter module 3452 may include concentration representation accepter module 3454, response representation accepter module 3456, plasma concentration accepter module 3458, bioavailability profile accepter module 3460, model accepter module 3462, characteristic accepter module 3470, attribute profile accepter module 3472, and/or parameter accepter module 3480. Model accepter module 3462 may include physiological model accepter module 3464, in vitro model accepter module 3466, and/or software output accepter module 3468. Attribute profile accepter module 3472 may include physiological characteristic accepter module 3474, medical history profile accepter module 3476, and/or group attribute accepter module 3478.

System 3200 generally represents instrumentality for accepting an indication of a schedule for administration of a bioactive agent to an individual, presenting an indication of an artificial sensory experience at Least partly based on the accepting an indication of the schedule for administration of the bioactive agent to the individual, and/or accepting an indication of at least one of a pharmacokinetic or pharmacodynamic profile of a bioactive agent. The operations of accepting an indication of a schedule for administration of a bioactive agent to an individual, presenting an indication of an artificial sensory experience at least partly based on the accepting an indication of the schedule for administration of the bioactive agent to the individual, and/or accepting an indication of at least one of a pharmacokinetic or pharmacodynamic profile of a bioactive agent may be accomplished electronically, such as with a set of interconnected electrical components, an integrated circuit, and/or a computer processor.

Figure 36:
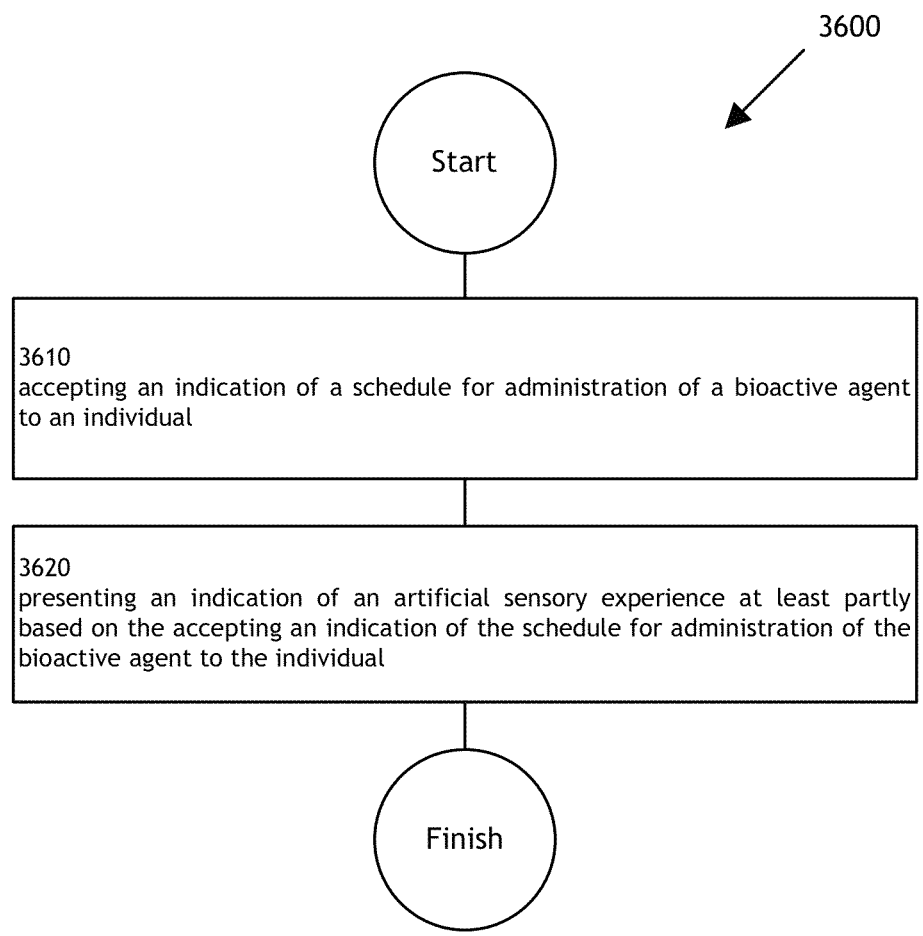
FIG. 36 illustrates an operational flow representing example operations related to presenting an indication of an artificial sensory experience.

FIG. 36 illustrates an operational flow 3600 representing example operations related to accepting an indication of a schedule for administration of a bioactive agent to an individual and/or presenting an indication of an artificial sensory experience at least partly based on the accepting an indication of the schedule for administration of the bioactive agent to the individual. In FIG. 36 and in following figures that include various examples of operational flows, discussion and explanation may be provided with respect to the above-described examples of FIGS. 32 through 35, and/or with respect to other examples and contexts. However, it should be understood that the operational flows may be executed in a number of other environments and contexts, and/or in modified versions of FIGS. 32 through 35. Also, although the various operational flows are presented in the sequence(s) illustrated, it should be understood that the various operations may be performed in other orders than those which are illustrated, or may be performed concurrently.

After a start operation, the operational flow 3600 moves to operation 3610. Operation 3610 depicts accepting an indication of a schedule for administration of a bioactive agent to an individual. For example, as shown in FIGS. 32 through 35, accepter module 3402 may accept an indication of a schedule for administration of a bioactive agent to an individual. In one embodiment, accepter module 3402 may accept an indication of a schedule for an intravenous administration of an opioid to an individual. In this embodiment, the schedule may include specific times and/or methods that the bioactive agent may be administered. For example, a time schedule may specify that an individual should receive a specific dose of morphine every two hours. In another example, an administration schedule may specify that an opioid should be administered intravenously at night and orally during waking hours. In some instances, accepter module 3402 may include a computer processor and/or a user interface coupled to the computer processor.

Then, operation 3620 depicts presenting an indication of an artificial sensory experience at least partly based on the accepting an indication of the schedule for administration of the bioactive agent to the individual. For example, as shown in FIGS. 32 through 35, presenter module 3410 may present an indication of an artificial sensory experience at least partly based on the accepting an indication of the schedule for administration of the bioactive agent to the individual. In one embodiment, presenter module 3410 may present an indication of a virtual world configured for distracting an individual at least partly based on accepting an indication of a bioactive agent administration time schedule. In this embodiment, the bioactive administration schedule may be coordinated so that an artificial sensory experience is administered when a bioactive agent may be less effective. Coordinating an artificial sensory experience administration schedule may serve to more efficiently distract and/or reduce, for example, an individual's pain during a period of low bioactive agent concentration in an individual's blood. In some instances, presenter module 3410 may include a computer processor, a display, and/or a printer.

Figure 37:
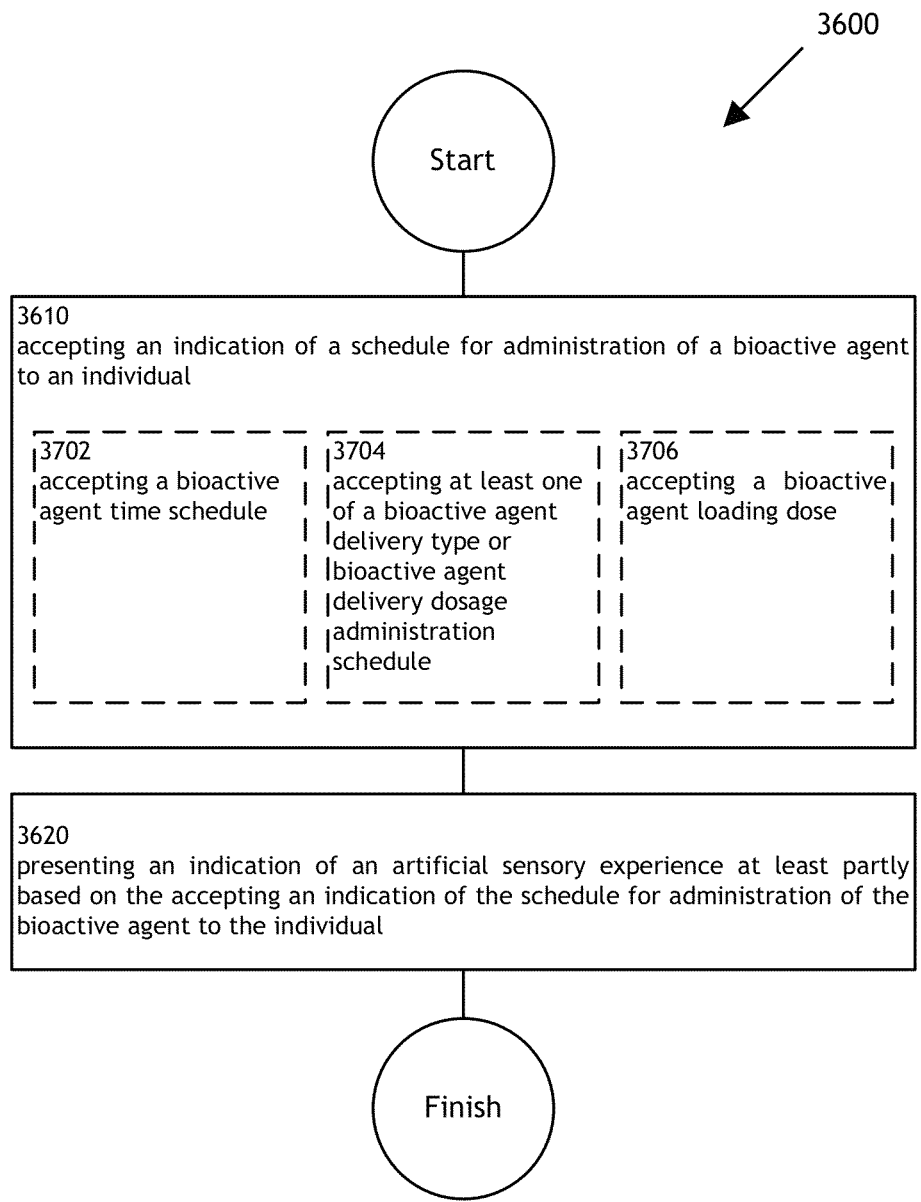
FIG. 37 illustrates an alternative embodiment of the operational flow of FIG. 36.

FIG. 37 illustrates alternative embodiments of the example operational flow 3600 of FIG. 36. FIG. 37 illustrates example embodiments where operation 3610 may include at least one additional operation. Additional operations may include operation 3702, operation 3704, and/or operation 3706.

Operation 3702 illustrates accepting a bioactive agent time schedule. For example, as shown in FIGS. 32 through 35, time schedule accepter module 3404 may accept a bioactive agent time schedule. In one embodiment, accepter module 3404 may accept a bioactive agent time schedule which specifies that an opioid, such as morphine, should be administered every two hours. A bioactive agent time schedule may specify, for example, the exact and/or appropriate time a bioactive agent should be administered. Additionally, a bioactive agent time schedule may specify different bioactive agents and/or combinations of bioactive agents, delivery methods for administering a bioactive agent, and/or bioactive agent dosage. Accepting a bioactive agent time schedule may include accepting from a computer processor, accepting from a memory device, and/or accepting from a user input. In one example, accepter module 3404 may accept a bioactive agent time schedule configured for printing on a medication blister pack, such as that described in Steinnaget, U.S. Pat. No. 4,974,729, which is incorporated herein by reference. In an additional example, accepter module 3404 may accept a bioactive agent time schedule from a device configured to remind an individual when to take medication, such as that in Goetz, U.S. Pat. No. 6,314,384, which is incorporated herein by reference. In some instances, accepter module 3404 may include a computer processor.

Operation 3704 illustrates accepting at least one of a bioactive agent delivery type or bioactive agent delivery dosage administration schedule. For example, as shown in FIGS. 32 through 35, bioactive agent schedule accepter module 3406 may accept at least one of a bioactive agent delivery type schedule or a bioactive agent delivery dosage administration schedule. Accepting a bioactive agent time schedule may include accepting from a computer processor, accepting from a memory device, and/or accepting from a user input. In one embodiment, bioactive agent schedule accepter module 3406 may accept a bioactive agent delivery type schedule specifying an intravenous administration of an opioid. In this embodiment, the bioactive agent time schedule may indicate that the opioid only be administered intravenously. In another embodiment, bioactive agent schedule accepter module 3406 may accept a bioactive agent delivery dosage specifying a first opioid administration dosage for a first time period, such as during an individual's awake hours, and a second opioid administration dosage for a second time period, such as during an individual's sleeping hours. In some instances, bioactive agent schedule accepter module 3406 may include a computer processor.

Operation 3706 illustrates accepting a bioactive agent loading dose. For example, as shown in FIGS. 32 through 35, dose accepter module 3408 may accept a bioactive agent loading dose. A loading dose may include an initial dose that is higher than a maintenance and/or average dose. Often, a loading dose may be used for a bioactive agent that is eliminated from an individual's body slowly. In one embodiment, dose accepter module 3408 may accept a phenytoin sodium loading dose for treatment of epileptic seizures. Some other bioactive agents a loading dose may be used with may include digoxin, teicoplanin, voriconazole, and/or procainamide. In some instances, dose accepter module 3408 may include a computer processor.

Figure 38:
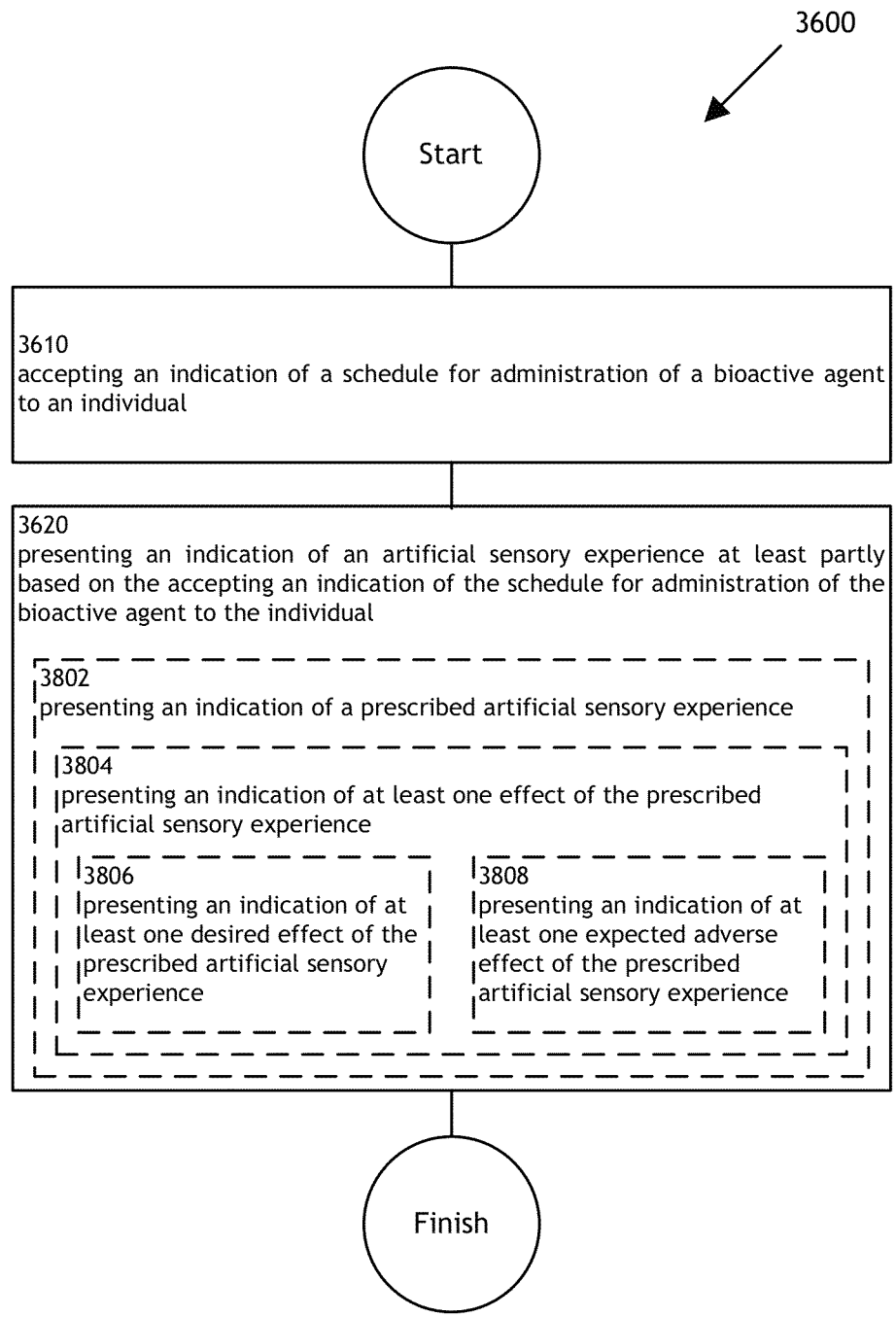
FIG. 38 illustrates an alternative embodiment of the operational flow of FIG. 36.

FIG. 38 illustrates alternative embodiments of the example operational flow 3600 of FIG. 36. FIG. 38 illustrates example embodiments where operation 3620 may include at least one additional operation. Additional operations may include operation 3802, operation 3804, operation 3806, and/or operation 3808.

Operation 3802 illustrates presenting an indication of a prescribed artificial sensory experience. For example, as shown in FIGS. 32 through 35, prescription presenter module 3412 may present an indication of a prescribed artificial sensory experience. A prescribed artificial sensory experience may include any artificial sensory experience prescribed by a health care professional, such as a physician, a mental health specialist, a nurse, a physical therapist, an occupational therapist, a chiropractor, and/or a homeopathic practitioner. In one embodiment, prescription presenter module 3412 may present an indication of a virtual world prescribed by a psychiatrist. In this embodiment, the prescribed virtual world may be configured to be administered in conjunction with a prescribed bioactive agent. Administering a prescribed bioactive agent in conjunction with a prescribed artificial sensory experience may serve to increase efficacy of the combined therapy, for example, by serving as a distraction from pain. In some instances, prescription presenter module 3412 may include a computer processor and/or a display device, such as a computer monitor and/or a printer.

Further, operation 3804 illustrates presenting an indication of at least one effect of the prescribed artificial sensory experience. For example, as shown in FIGS. 32 through 35, effect presenter module 3414 may present an indication of at least one effect of the prescribed artificial sensory experience. In one embodiment, effect presenter module 3414 may present an indication of at least one effect of the prescribed artificial sensory experience. An effect may include a reaction and/or thing that occurs as a result of the artificial sensory experience. For example, an effect may include a side effect, a desired effect, and/or an adverse effect. Some examples of an effect may include an increased bioactive agent efficacy, dizziness, and/or a decreased heart rate. In some instances, effect presenter module 3414 may include a computer processor.

Further, operation 3806 illustrates presenting an indication of at least one desired effect of the prescribed artificial sensory experience. For example, as shown in FIGS. 32 through 35, desired effect presenter module 3416 may present an indication of at least one desired effect of the prescribed artificial sensory experience. Some examples of a desired effect may include effects such as an increased bioactive agent efficacy, a cured illness and/or condition, and/or a changed behavior. In one embodiment, desired effect presenter module 3416 may present an indication of an increased opioid efficacy measured by self pain evaluation by an individual. In some instances, desired effect presenter module 3416 may include a computer processor and/or a display, such as a monitor and/or a printer.

Further, operation 3808 illustrates presenting an indication of at least one expected adverse effect of the prescribed artificial sensory experience. For example, as shown in FIGS. 32 through 35, adverse effect presenter module 3418 may present an indication of an expected adverse effect of the prescribed artificial sensory experience. An adverse effect may include a harmful and/or undesired effect resulting from an intervention, such as an artificial sensory experience. Some examples of an adverse effect may include headache, dizziness, depression, bleeding, seizure, and/or fever. In one embodiment, adverse effect presenter module 3418 may present an indication of fever in an individual while being administered a prescribed artificial sensory experience and bioactive agent. In some instances, adverse effect presenter module 3418 may include a computer processor, a display device, such as a monitor and/or printer, and/or medical instrumentation, such as a thermometer configured for measuring a body temperature.

Figure 39:
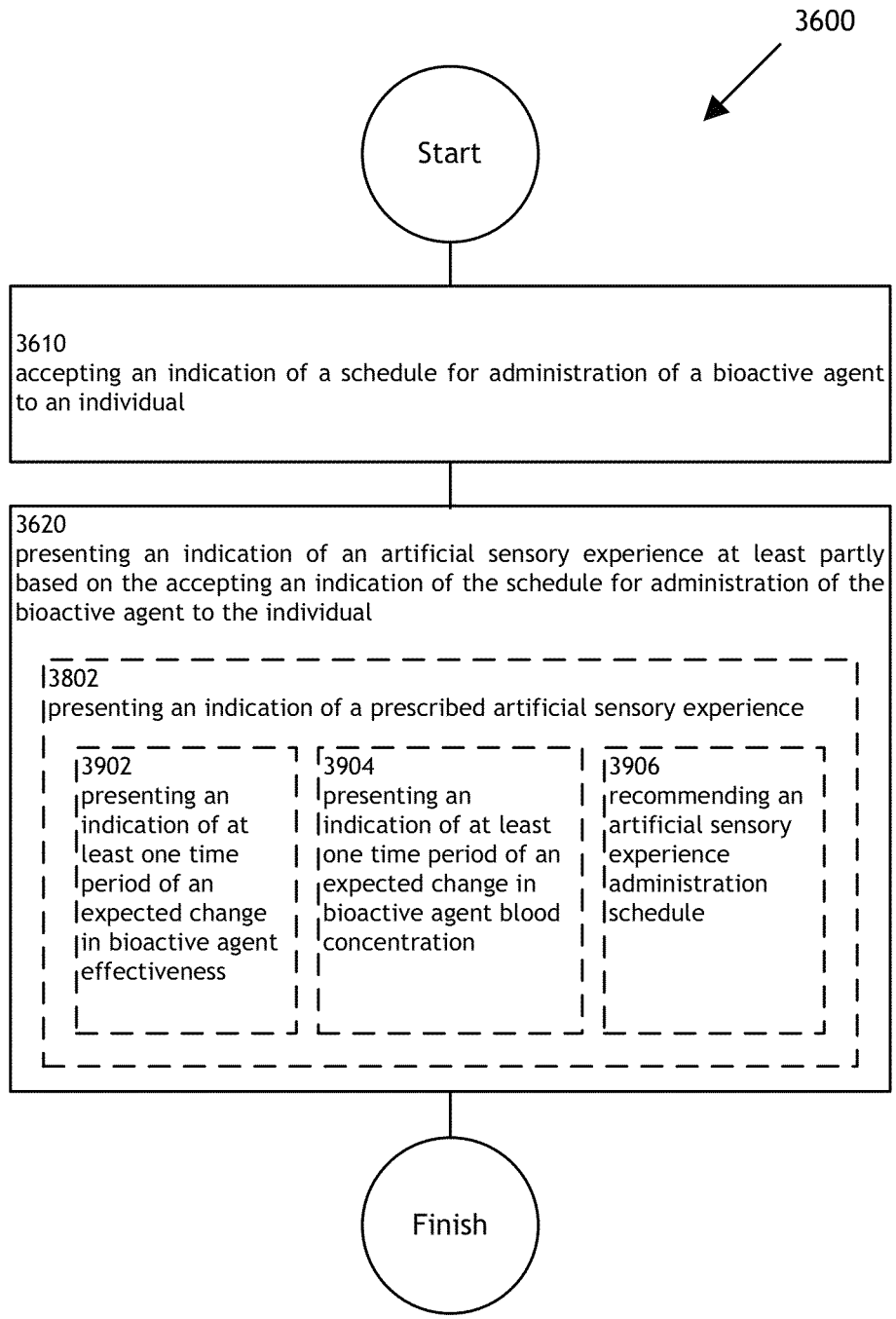
FIG. 39 illustrates an alternative embodiment of the operational flow of FIG. 36.

FIG. 39 illustrates alternative embodiments of the example operational flow 3600 of FIG. 36. FIG. 39 illustrates example embodiments where operation 3620 may include at Least one additional operation. Additional operations may include operation 3902, operation 3904, and/or operation 3906. Further, operation 3902 illustrates presenting an indication of at Least one time period of an expected change in bioactive agent effectiveness. For example, as shown in FIGS. 32 through 35, effectiveness presenter module 3420 may present an indication of at least one time period of an expected change in bioactive agent effectiveness. In one embodiment, effectiveness presenter module 3420 may present an indication of a time period when an opioid is expected to decrease in effectiveness. Such an indication of decrease and/or change in bioactive agent effectiveness may serve to indicate an appropriate time period for administering and/or modifying an artificial sensory experience to compensate for a change in bioactive agent efficacy. In another embodiment, effectiveness presenter module 3420 may present an indication of a time period where a blood stream morphine concentration drops. This time period of tow blood stream morphine concentration may be appropriate for presenting an immersive virtual world for serving as a distraction to any increase in pain caused by towered morphine concentration. In some instances, effectiveness presenter module 3420 may include a computer processor.

Further, operation 3904 illustrates presenting an indication of at least one time period of an expected change in bioactive agent blood concentration. For example, as shown in FIGS. 32 through 35, concentration presenter module 3422 may present an indication of at least one time period of an expected change in bioactive agent blood concentration. In one embodiment, concentration presenter module 3422 may present an indication of a one hour time period of an expected change in hydrocodone blood concentration. Indicating a time period of a change in blood concentration may serve to help determine an artificial sensory experience administration schedule. For example, if a bioactive agent blood concentration is expected to be reduced during a certain time period, an artificial sensory experience configured for distracting an individual from pain may be selected for administration during that time period. In some instances, concentration presenter module 3422 may include a computer processor and/or a display device, such as a printer and/or a computer monitor.

Further, operation 3906 illustrates recommending an artificial sensory experience administration schedule. For example, as shown in FIGS. 32 through 35, recommender module 3424 may recommend an artificial sensory experience administration schedule. In one embodiment, recommender module 3424 may recommend a time schedule for administration of a virtual world experience. A time schedule may be recommended by taking into account factors involving the individual and/or the bioactive agent. For example, efficacy of the bioactive agent versus time may be a factor, such as a time period when the bioactive agent is less effective. Efficacy of the bioactive agent may be a factor in determining when an artificial sensory experience is administered because of the potential for the artificial sensory experience to compensate for a changed bioactive agent efficacy. An additional factor may include an attribute of the individual, such as how a bioactive agent and/or specific artificial sensory experience affects the individual, for example a side effect. Another example of recommending an artificial sensory experience may be found in Akazawa et al., U.S. Pat. No. 7,155,680, which is incorporated herein by reference. In some instances, recommender module 3424 may include a computer processor.

Figure 40:
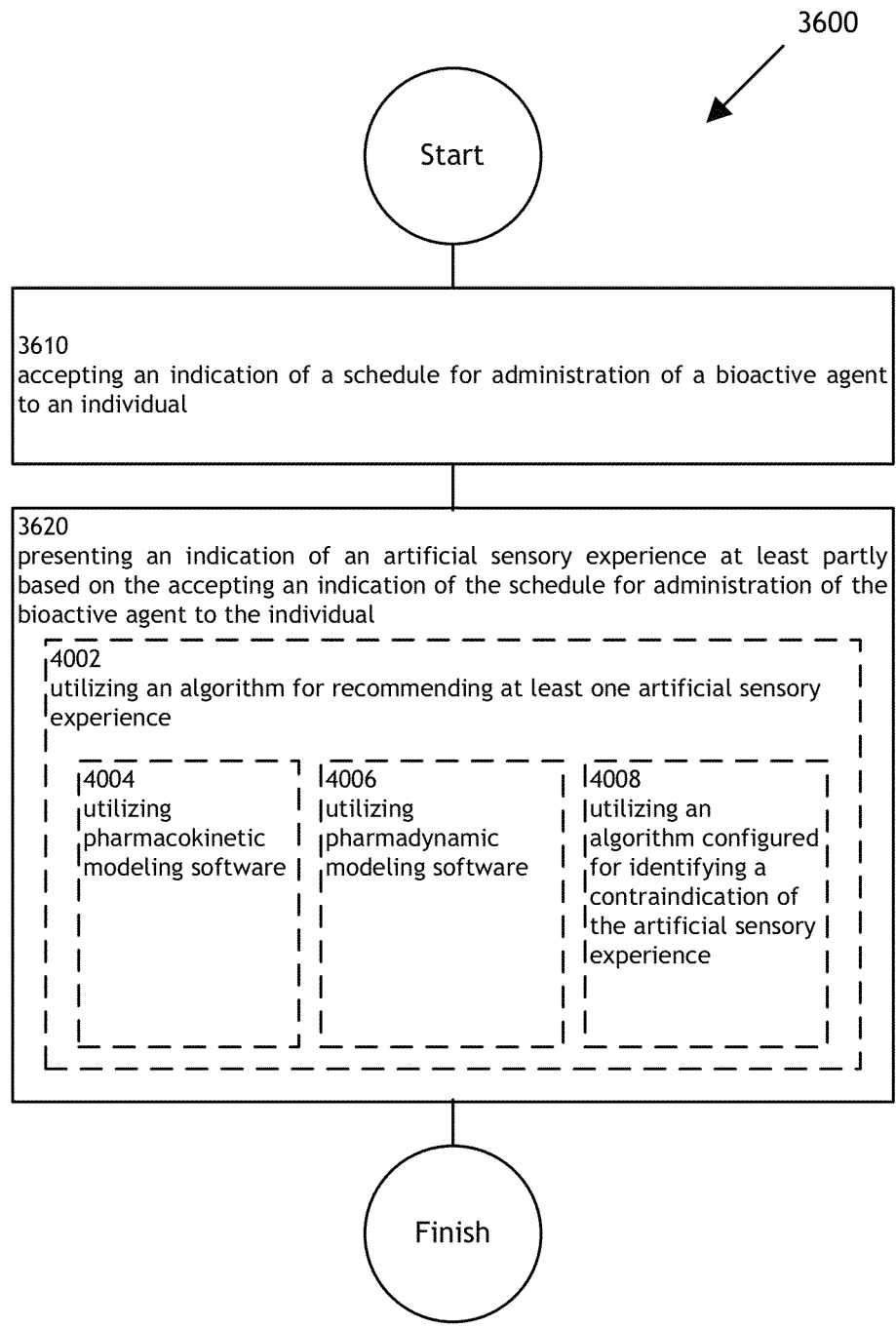
FIG. 40 illustrates an alternative embodiment of the operational flow of FIG. 36.

FIG. 40 illustrates alternative embodiments of the example operational flow 3600 of FIG. 36. FIG. 40 illustrates example embodiments where operation 3620 may include at least one additional operation. Additional, operations may include operation 4002, operation 4004, operation 4006, and/or operation 4008.

Operation 4002 illustrates utilizing an algorithm for recommending at least one artificial sensory experience. For example, as shown in FIGS. 32 through 35, algorithm utilizer module 3426 may utilize an algorithm for recommending at least one artificial sensory experience. An algorithm for recommending an artificial sensory experience may include any computation, formula, statistical survey, and/or look-up table for determining and/or selecting a suitable artificial sensory experience. Some examples may include a computer software algorithm, a calculator, a flowchart, and/or a decision tree. In one embodiment, algorithm utilizer module 3426 may utilize an algorithm that uses an inputted indication of an analgesic, such as oxycodone, and determines a suitable artificial sensory experience by analyzing periods of low blood concentration of the oxycodone. In this embodiment, algorithm utilizer module 3426 may recommend an artificial sensory experience that may be effective in pain distraction when bioactive agent blood concentration may be reduced but before an additional dose may be available. In some instances, algorithm utilizer module 3426 may include a computer processor.

Further, operation 4004 illustrates utilizing pharmacokinetic modeling software. For example, as shown in FIGS. 32 through 35, pharmacokinetic software utilizer module 3428 may utilize pharmacokinetic modeling software. In one embodiment, pharmacokinetic software utilizer module 3428 may utilize modeling software to determine and display characteristics regarding a specific bioactive agent. Pharmacokinetic modeling software may include software configured for displaying pharmacokinetic information for a specific bioactive agent, such as a pharmacokinetic profile. Additionally, pharmacokinetic modeling software may analyze and compare a specific bioactive agent and/or a pharmacokinetic profile with an artificial sensory experience and make a recommendation based on, for example, low bioactive blood concentration. An additional example of utilizing pharmacokinetic modeling software may be found in Bachman et al., U.S. Patent Publication No. 2006/0161408, which is incorporated herein by reference. Some examples of pharmacokinetic software may include acslXtreme, available from Aegis Technologies Group, Inc., West Austin, Tex., and GastroPlus, available from Simulations Plus, Inc., Lancaster, Calif. In some instances, pharmacokinetic software utilizer module 3428 may include a computer processor. Further, operation 4006 illustrates utilizing pharmacodynamic modeling software. For example, as shown in FIGS. 32 through 35, pharmacodynamic software utilizer module 3430 may utilize pharmacodynamic modeling software. In one embodiment, pharmacodynamic software utilizer module 3430 may utilize pharmacodynamic modeling software for determining an appropriate artificial sensory experience based on how a specific bioactive agent, such as morphine, affects an individual. Utilizing pharmacodynamic software may be useful for determining an appropriate artificial sensory experience that may compensate for a period of tow bioactive agent blood concentration. An appropriate artificial sensory experience may compensate for reduced bioactive agent efficacy by acting as a distraction when the bioactive agent concentration may be reduced. One example of pharmacodynamic modeling software may include GastroPlus, available from Simulations Plus, Inc., Lancaster, Calif. In some instances, pharmacodynamic software utilizer module 3430 may include a computer processor.

Further, operation 4008 illustrates utilizing an algorithm configured for identifying a contraindication of the artificial sensory experience. For example, as shown in FIGS. 32 through 35, contraindication algorithm utilizer module 3432 may utilize an algorithm configured for identifying a contraindication of the artificial sensory experience. A contraindication of an artificial sensory experience may include giving an indication against the advisability of the artificial sensory experience. For example, contraindication algorithm utilizer module 3432 may utilize an algorithm that considers an individual's personal medical history, such as a phobia, and may recommend not prescribing a certain artificial sensory experience, which may include an object that may trigger the phobia. Contraindication algorithm utilizer module 3432 may identify a contraindication of an artificial sensory experience for reasons such as an adverse effect and/or inefficacy. In some instances, contraindication algorithm utilizer module 3432 may include a computer processor.

Figure 41:
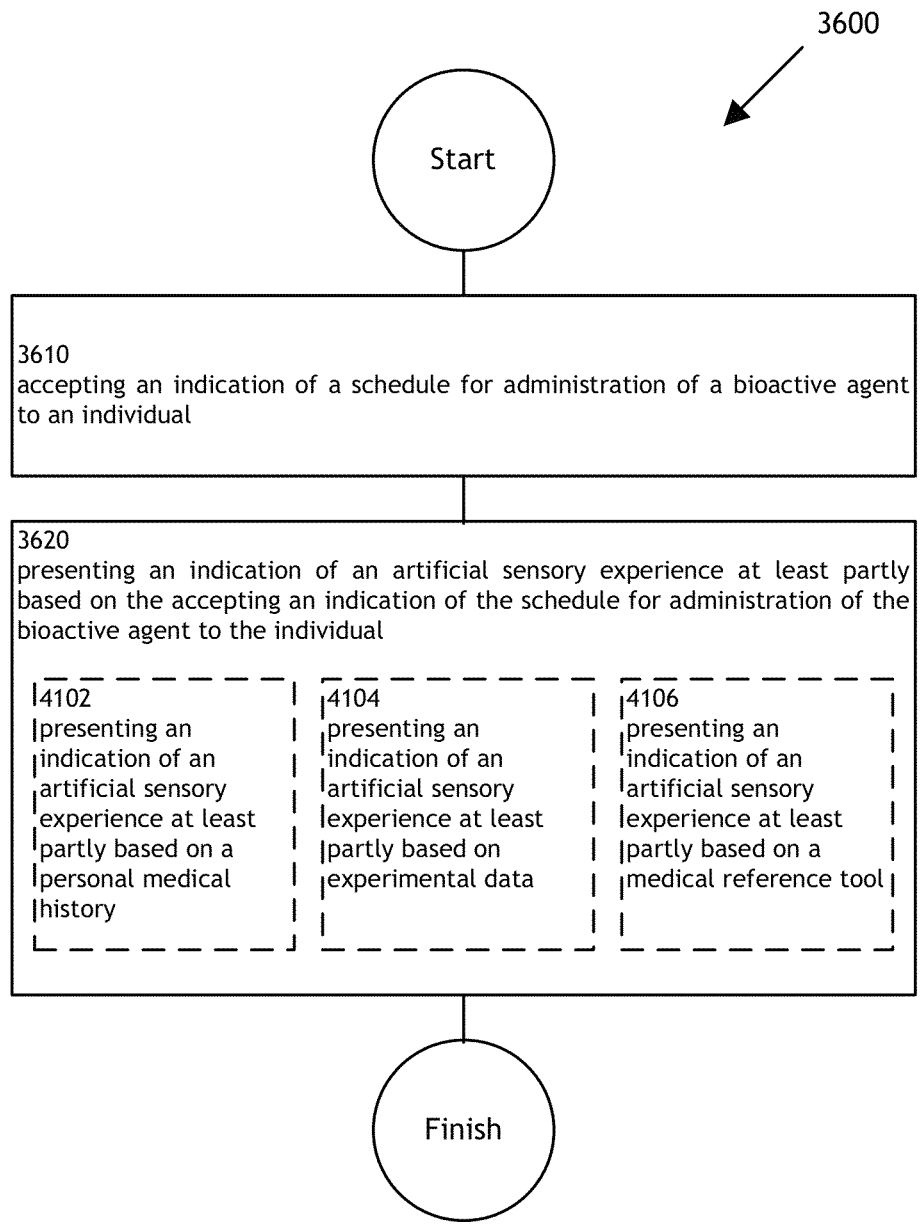
FIG. 41 illustrates an alternative embodiment of the operational flow of FIG. 36.

FIG. 41 illustrates alternative embodiments of the example operational flow 3600 of FIG. 36. FIG. 41 illustrates example embodiments where operation 3620 may include at least one additional operation. Additional operations may include operation 4102, operation 4104, and/or operation 4106.

Operation 4102 illustrates presenting an indication of an artificial sensory experience at least partly based on a personal medical history. For example, as shown in FIGS. 32 through 35, medical history presenter module 3434 may present an indication of an artificial sensory experience at least partly based on a personal medical history. A medical history may include a personal history and/or a family history. A personal medical history may include a list of previous illnesses, symptoms, medicines, treatments, health risk factors, operations, and/or doctor visits associated with at least one individual. A personal and/or a family medical history may include life history and/or social history characteristics such as smoking, drinking, drug use, sexual history, exercise history, eating history, nutraceutical history, or the like. In one embodiment, medical history presenter module 3434 may present an indication of a suitable virtual world based on a personal medical history. In this embodiment, the personal medical history may indicate that an individual may be averse to a certain virtual world, such as a virtual world with rapid animation that may cause nausea. In some instances, medical history presenter module 3434 may include a computer processor and/or a display device, such as a computer monitor and/or a printer.

Operation 4104 illustrates presenting an indication of an artificial sensory experience at Least partly based on experimental data. For example, as shown in FIGS. 32 through 35, experimental data presenter module 3436 may present an indication of an artificial sensory experience at least partly based on experimental data. Experimental data may include any data from an experiment, such as a clinical trial. The experiment may be an experiment including an individual and/or a group of people. In one embodiment, experimental data presenter module 3436 may present an indication of a virtual world suitable for an individual based on a clinical trial involving a group of 1,000 people showing a certain success rate for reducing a phobia, such as fear of heights. In some instances, experimental data presenter module 3436 may include a computer processor and/or a display device, such as a computer monitor, a mobile phone, and/or a printer.

Operation 4106 illustrates presenting an indication of an artificial sensory experience at least partly based on a medical reference tool. For example, as shown in FIGS. 32 through 35, medical reference tool presenter module 3438 may present an indication of an artificial sensory experience at least partly based on a medical reference tool. A medical reference tool may include a reference book, a reference database, and/or reference software. Some examples of a medical reference book may include a medical dictionary, a medical journal, and/or a book of drug interactions. One example of a reference database may include the National Cancer Center Cancer Image Reference (NCC-CIR) database and/or DynaMed. Some examples of reference software may include Skyscape software for a mobile phone and/or MedAlert. In one embodiment, medical reference tool presenter module 3438 may present an indication of an artificial sensory experience based on a reference database, such as a database including data from a clinical trial. In some instances, medical reference tool presenter module 3438 may include a computer processor and/or a display device, such as a mobile phone, a printer, and/or a computer monitor.

Figure 42:
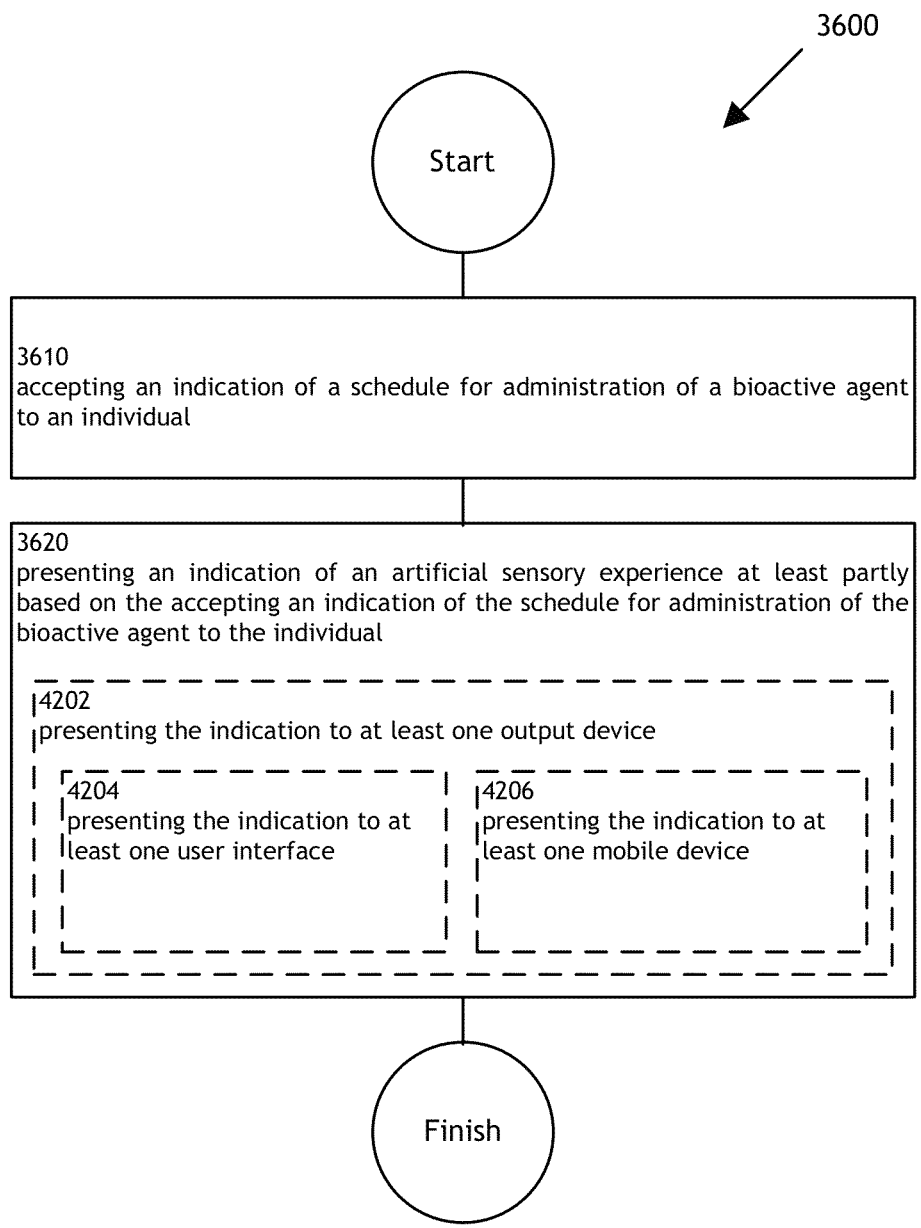
FIG. 42 illustrates an alternative embodiment of the operational flow of FIG. 36.

FIG. 42 illustrates alternative embodiments of the example operational flow 3600 of FIG. 36. FIG. 42 illustrates example embodiments where operation 3620 may include at least one additional operation. Additional operations may include operation 4202, operation 4204, and/or operation 4206.

Operation 4202 illustrates presenting the indication to at least one output device. For example, as shown in FIGS. 32 through 35, output device presenter module 3440 may present to at Least one output device. In one example, output device presenter module 3440 may present an indication of a combination prescription medication and an artificial sensory experience therapy to an output device 130, such as a printer and/or monitor at a health clinic. An output device may include any hardware device configured for receiving computer output. Some examples of an output device may include a printer, a monitor, a mobile phone, a speaker, and/or a visual display unit. The output device 130 may be used by individual 134. In some instances, output device presenter module 3440 may include a computer processor.

Further, operation 4204 illustrates presenting the indication to at least one user interface. For example, as shown in FIGS. 32 through 35, user interface presenter module 3442 may present to at least one user interface. In one embodiment, user interface presenter module 3442 may present to a touchscreen device. A user interface may include means by which an individual may interact with a system. Some examples of a user interface may include a touchscreen, a graphical user interface, a tactile interface, and/or a live user interface. In some instances, user interface presenter module 3442 may include a computer processor.

Further, operation 4206 illustrates presenting the indication to at least one mobile device. For example, as shown in FIGS. 32 through 35, mobile device presenter module 3444 may present to at least one mobile device. In one embodiment, mobile device presenter module 3444 may present to a mobile phone. A mobile device may include a portable computing device and may have wireless connection capability. Some examples of a mobile device may include a laptop or notebook computer, a personal digital assistant (PDA), an ipod, a smartphone, an Enterprise digital assistant (EDA), and/or a pager. In some instances, mobile device presenter module 3444 may include a computer processor.

Figure 43:
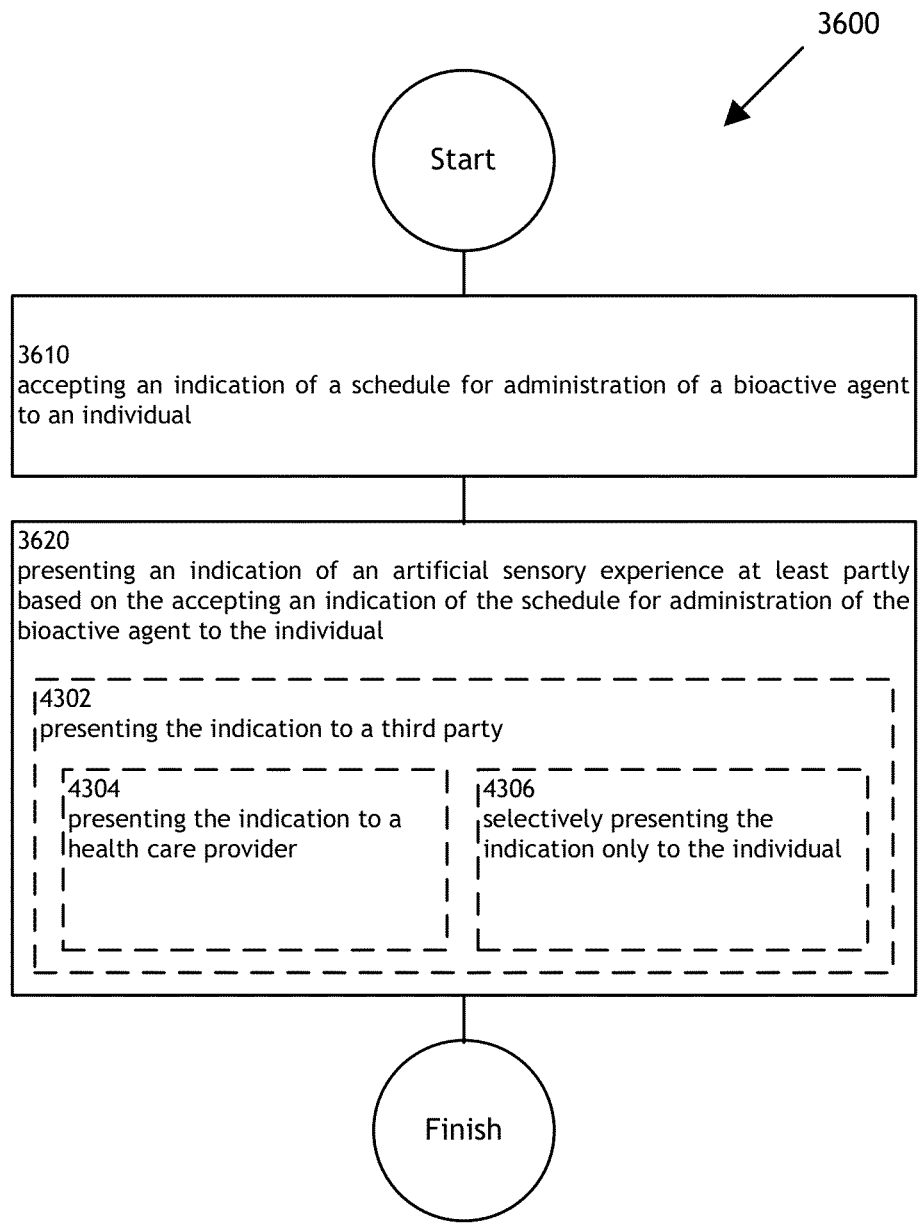
FIG. 43 illustrates an alternative embodiment of the operational flow of FIG. 36.

FIG. 43 illustrates alternative embodiments of the example operational flow 3600 of FIG. 36. FIG. 43 illustrates example embodiments where operation 3620 may include at least one additional operation. Additional operations may include operation 4302, operation 4304, and/or operation 4306.

Operation 4302 illustrates presenting the indication to a third party. For example, as shown in FIGS. 32 through 35, third party presenter module 3446 may present to an individual's physician. A third party may include a party that is an independent party, person, and/or entity. Some examples of a third party may include a physician, a medical database, a hospital, a law enforcement agency, and/or a pharmacy. One example of reporting to a third party may include creating displays and reports for aggregating data from therapy results, further discussed in Bair et al., U.S. Pat. No. 6,067,523, which is incorporated herein by reference. In some instances, third party presenter module 3446 may include a computer processor and/or a communications device, such as a monitor and network link.

Further, operation 4304 illustrates presenting the indication to a health care provider. For example, as shown in FIGS. 32 through 35, health care provider presenter module 3448 may present to a health care provider. A health care provider may include a pharmacy, a pharmaceutical company, a medical device company, a research institution, a computer software and/or computer hardware company, a website, a nurse and/or a physician. In one embodiment, health care provider presenter module 3448 may present to a physician a prescribed combination artificial sensory experience and bioactive agent therapy via a secured website. In some instances, health care provider presenter module 3448 may include a computer processor.

Further, operation 4306 illustrates selectively presenting the indication only to the individual. For example, as shown in FIGS. 32 through 35, selective presenter module 3450 may selectively present only to the individual. Selective presenting may include limiting and/or blocking access of an individual's compliance results and/or a prescribed therapy, such as a prescribed artificial sensory experience and/or bioactive agent to a specific party. For example, selective presenter module 3450 may present only to individual 134 and may keep results of a certain combination therapy confidential. In one embodiment, an encryption key may be employed to protect selected information. In an additional example, selective presenter module 3450 may report only to a law enforcement agency and/or representative, such as a probation officer, and not to individual 134. In some instances, selective presenter module 3450 may include a computer processor.

Figure 44:
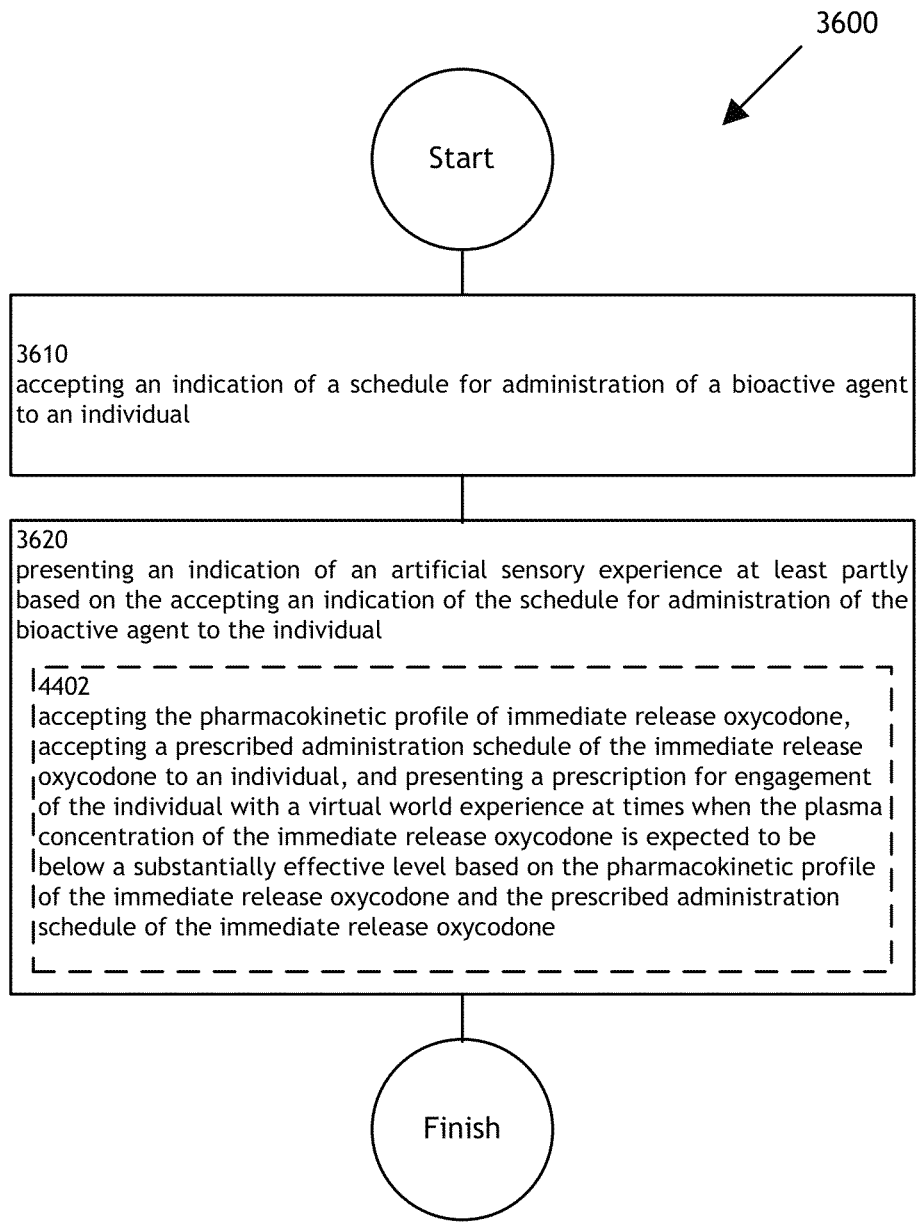
FIG. 44 illustrates an alternative embodiment of the operational flow of FIG. 36.

FIG. 44 illustrates alternative embodiments of the example operational flow 3600 of FIG. 36. FIG. 44 illustrates example embodiments where operation 3620 may include at least one additional operation. Additional operations may include an operation 4402.

Operation 4402 illustrates accepting the pharmacokinetic profile of immediate release oxycodone, accepting a prescribed administration schedule of the immediate release oxycodone to an individual, and presenting a prescription for engagement of the individual with a virtual world experience at times when the plasma concentration of the immediate release oxycodone is expected to be below a substantially effective level based on the pharmacokinetic profile of the immediate release oxycodone and the prescribed administration schedule of the immediate release oxycodone. For example, as shown in FIGS. 32 through 35, accepter module 3402 and presenter module 3410 may accept the pharmacokinetic profile of immediate release oxycodone, accept a prescribed administration schedule of the immediate release oxycodone to an individual, and present a prescription for engagement of the individual with a virtual world experience at times when the plasma concentration of the immediate release oxycodone is expected to be below a substantially effective level based on the pharmacokinetic profile of the immediate release oxycodone and the prescribed administration schedule of the immediate release oxycodone. In some instances, accepter module 3402 and presenter module 3410 may include, for example, a computer processor, a printer, a handheld mobile device, and/or a computer display.

Figure 45:
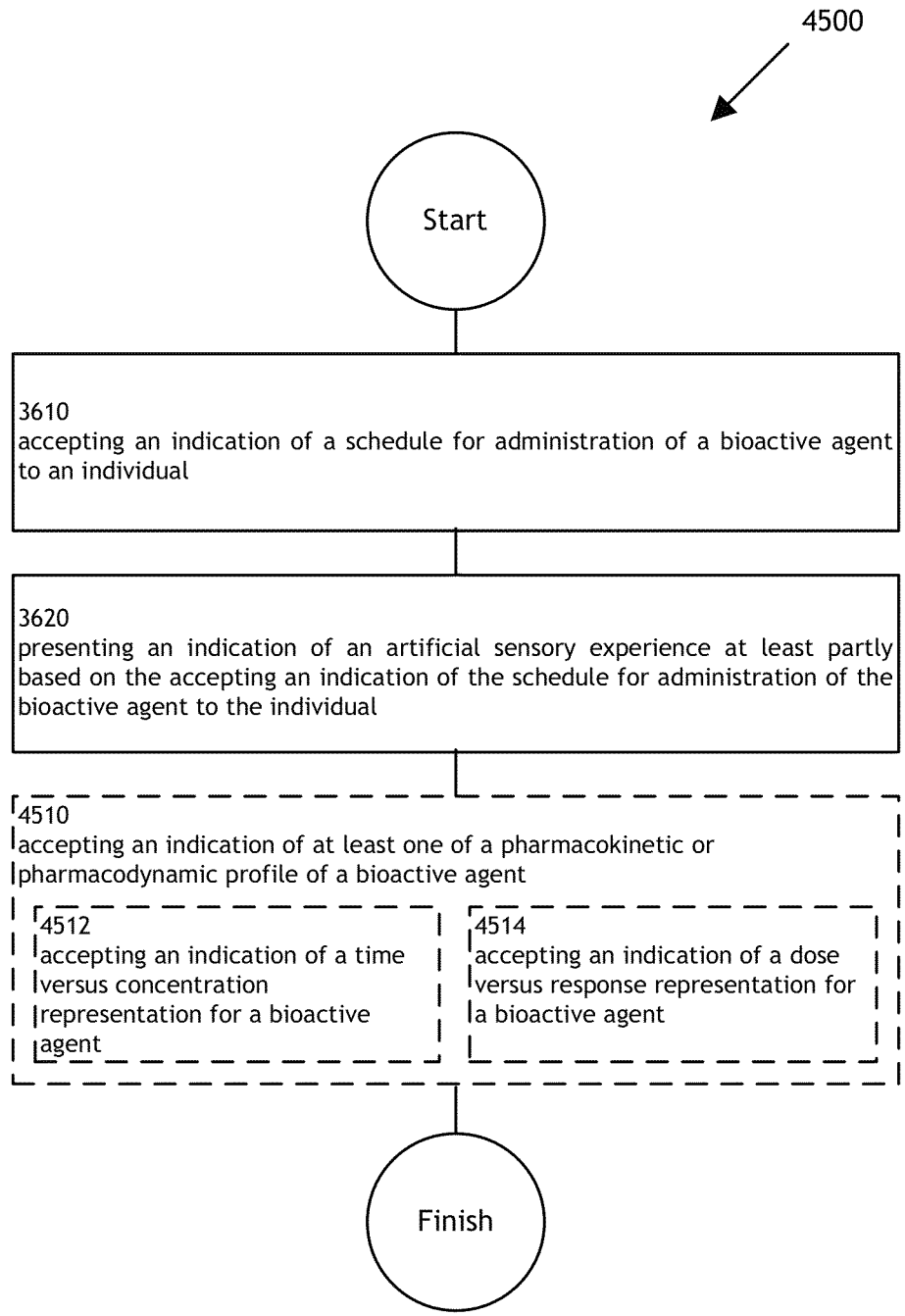
FIG. 45 illustrates an alternative embodiment of the operational flow of FIG. 36.

FIG. 45 illustrates an operational flow 4500 representing example operations related to accepting an indication of a schedule for administration of a bioactive agent to an individual, presenting an indication of an artificial sensory experience at least partly based on the accepting an indication of the schedule for administration of the bioactive agent to the individual, and accepting an indication of at least one of a pharmacokinetic or pharmacodynamic profile of a bioactive agent. FIG. 45 illustrates an example embodiment where the example operational flow 3600 of FIG. 36 may include at least one additional operation. Additional operations may include operation 4510, operation 4512, and/or operation 4514.

After a start operation, operation 3610, and operation 3620, the operational flow 4500 moves to operation 4510. Operation 4510 illustrates accepting an indication of at least one of a pharmacokinetic or pharmacodynamic profile of a bioactive agent. For example, as shown in FIGS. 32 through 35, profile accepter module 3452 may accept an indication of a pharmacokinetic and/or a pharmacodynamic profile of a bioactive agent. A bioactive agent pharmacokinetic profile may include information regarding how the bioactive agent is affected by the body. A pharmacokinetic profile may include information such as absorption, distribution, metabolism, and/or elimination. A bioactive agent pharmacodynamic profile may include information regarding how a bioactive agent is affected by the body, such as routes and/or mechanisms of bioactive agent absorption and excretion, the bioactive agent biotransformation in the body, and/or the rate of a bioactive agent action. In one embodiment, profile accepter module 3452 may accept an indication of a pharmacokinetic profile for codeine including, for example, a metabolism rate. In another embodiment, profile accepter module 3452 may accept an indication of a pharmacodynamic profile for methadone. In some instances, profile accepter module 3452 may include a computer processor and/or a user interface.

Operation 4512 illustrates accepting an indication of a time versus concentration representation for a bioactive agent. For example, as shown in FIGS. 32 through 35, concentration representation accepter module 3454 may accept an indication of a time versus concentration representation for a bioactive agent. In one embodiment, concentration representation accepter module 3454 may accept an indication of a time versus concentration representation for a regiment of prescribed morphine. A time versus concentration representation may serve to indicate time periods of reduced and/or changed bioactive agent effectiveness. A determination of reduced and/or changed bioactive agent effectiveness may indicate a suitable time period for administering an artificial sensory experience, which may serve as an additional distraction and/or compensation. In some instances, concentration representation accepter module 3454 may include a computer processor.

Operation 4514 illustrates accepting an indication of a dose versus response representation for a bioactive agent. For example, as shown in FIGS. 32 through 35, response representation accepter module 3456 may accept an indication of a dose versus response representation for bioactive agent. In one embodiment, response representation accepter module 3456 may accept an indication of a dose versus response representation for fluoxetine hydrochloride. A dose versus response representation may serve to indicate a proper bioactive agent dosage for a desired response of an individual while the individual experiences an artificial sensory experience. In some instances, response representation accepter module 3456 may include a computer processor.

Figure 46:
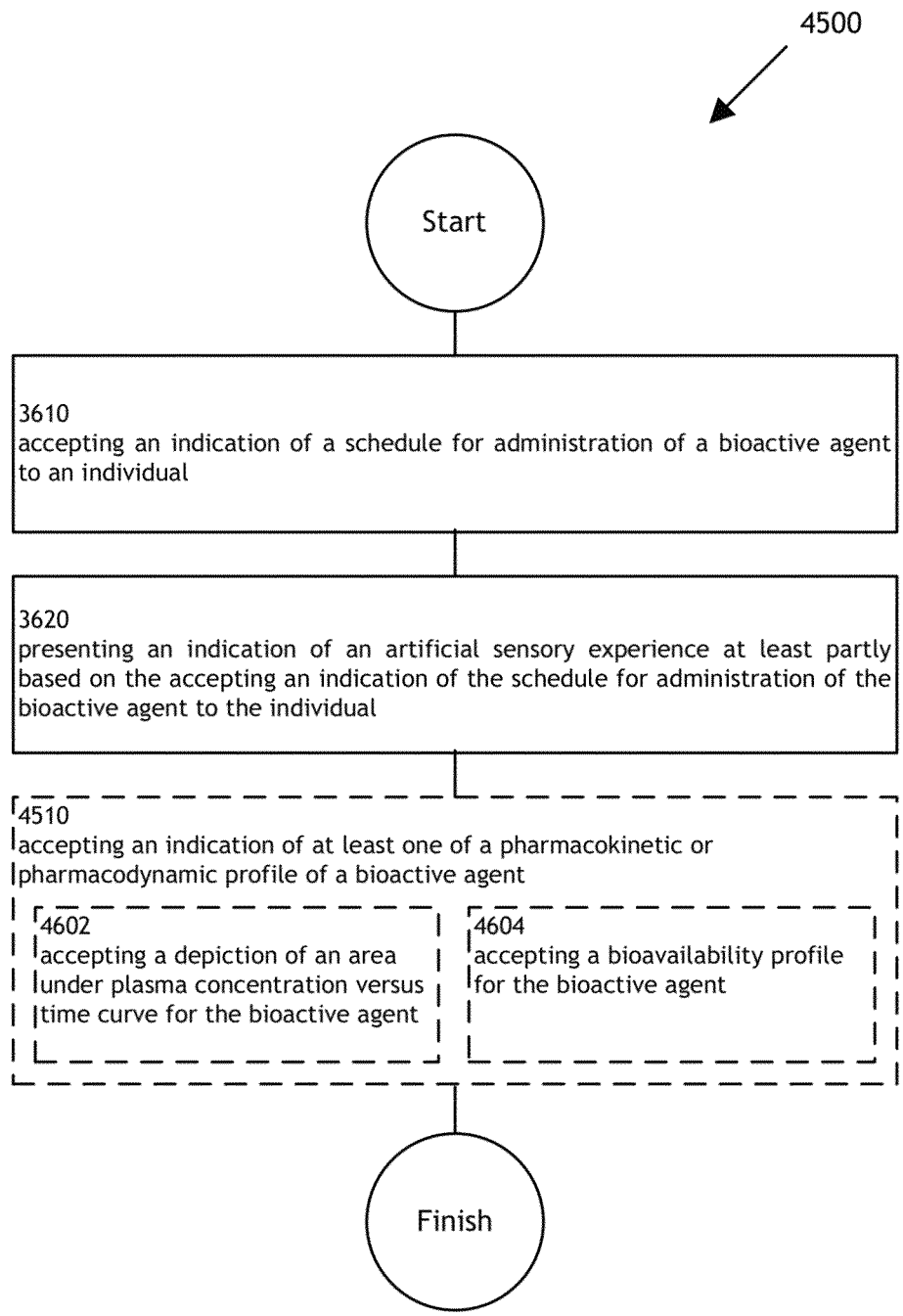
FIG. 46 illustrates an alternative embodiment of the operational flow of FIG. 36.

FIG. 46 illustrates alternative embodiments of the example operational flow 4500 of FIG. 45. FIG. 46 illustrates example embodiments where operation 4510 may include at least one additional operation. Additional operations may include operation 4602, and/or operation 4604.

Operation 4602 illustrates accepting a depiction of an area under plasma concentration versus time curve for the bioactive agent. For example, as shown in FIGS. 32 through 35, plasma concentration accepter module 3458 may accept a depiction of an area under plasma concentration versus time curve for the bioactive agent. In one embodiment, plasma concentration accepter module 3458 may accept a depiction of an area under plasma concentration versus time curve for fentanyl. An area under plasma concentration versus time curve may be useful for determining an appropriate time period to administer an artificial sensory experience configured to serve as a distraction and compensate for a reduced bioactive agent efficacy, in some instances, plasma concentration accepter module 3458 may include a computer processor.

Operation 4604 illustrates accepting a bioavailability profile for the bioactive agent. For example, as shown in FIGS. 32 through 35, bioavailability profile accepter module 3460 may accept a bioavailability profile for the bioactive agent. In one embodiment, bioavailability profile accepter module 3460 may accept a bioavailability profile for hydromorphone. A bioavailability profile may include information describing the fraction of a bioactive agent dose that may reach systemic circulation in an unchanged state or is therapeutically active. In another embodiment, bioavailability profile accepter module 3460 may accept a bioavailability profile for a combination hydrocodone/paracetamol oral medication. In some instances, bioavailability profile accepter module 3460 may include a computer processor.

Figure 47:
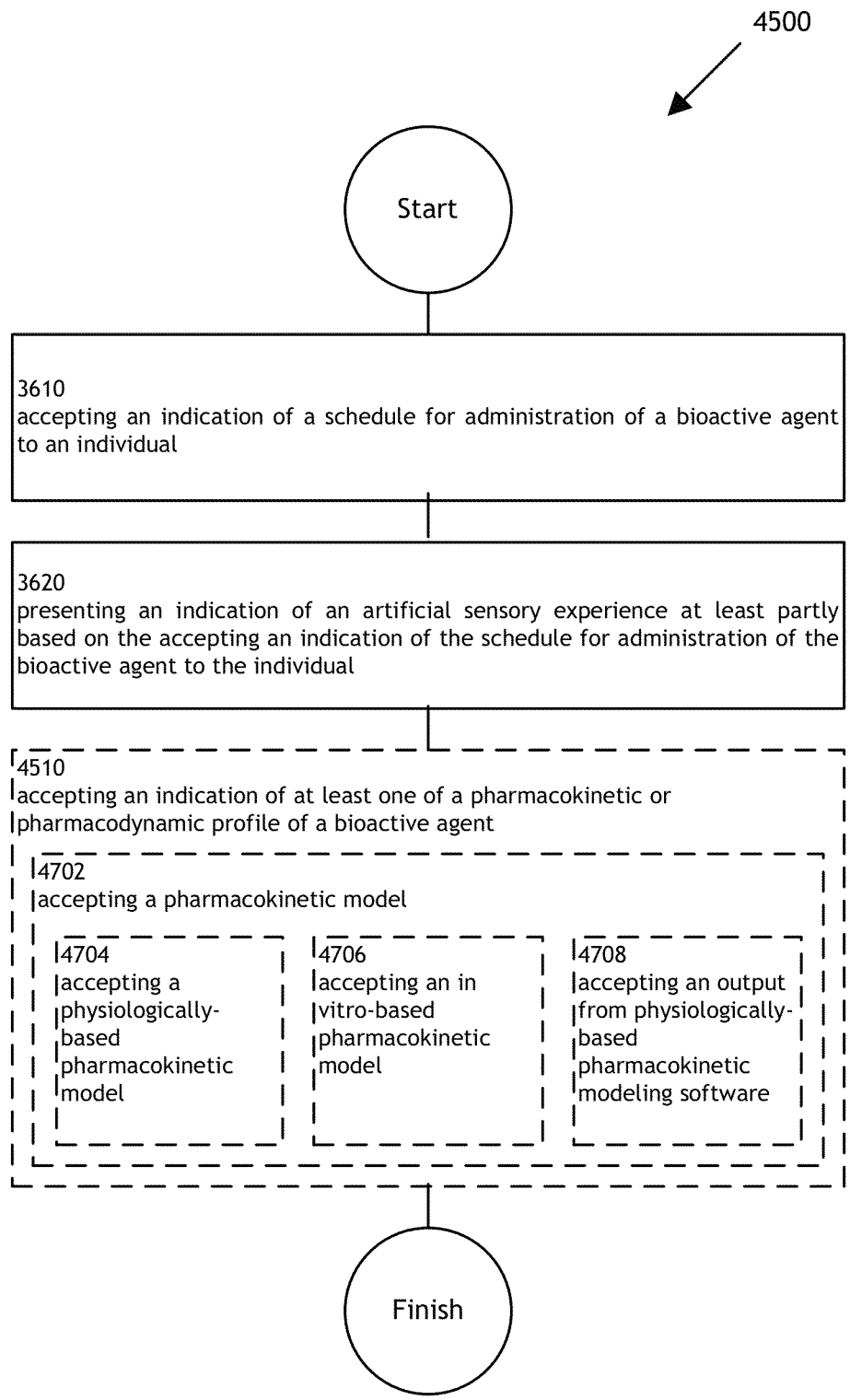
FIG. 47 illustrates an alternative embodiment of the operational flow of FIG. 36.

FIG. 47 illustrates alternative embodiments of the example operational flow 4500 of FIG. 45. FIG. 47 illustrates example embodiments where operation 4510 may include at least one additional operation. Additional operations may include operation 4702, operation 4704, operation 4706, and/or operation 4708.

Operation 4702 illustrates accepting a pharmacokinetic model. For example, as shown in FIGS. 32 through 35, model accepter module 3462 may accept a pharmacokinetic model. A pharmacokinetic profile may include information regarding bioactive agent absorption, distribution, metabolism, and/or elimination. In one embodiment, model accepter module 3462 may accept a pharmacokinetic model including a model derived by computer software. A pharmacokinetic model may include, for example, a one-compartment model or a two-compartment model. A one-compartment model may be suitable for a bioactive agent that rapidly equilibrates in a tissue compartment. A two-compartment model may be suitable for a bioactive agent that slowly equilibrates in a tissue compartment. Additionally, a pharmacokinetic model may be presented as a data plot, such as a plot of plasma drug concentration versus time. In some instances, model accepter module 3462 may include a computer processor.

Further, operation 4704 illustrates accepting a physiologically-based pharmacokinetic model. For example, as shown in FIGS. 32 through 35, physiological model accepter module 3464 may accept a physiologically-based pharmacokinetic model. In one embodiment, physiological model accepter module 3464 may accept a pharmacokinetic model based on weight and height. A pharmacokinetic model based on weight and height may present pharmacokinetic information based on physiological attributes of an individual or a group of individuals. For example, a physiologically-based pharmacokinetic model may be derived from a clinical trial by using the results only from a group of individuals meeting a specific weight and height requirement. Other physiologic attributes a pharmacokinetic model may be based from may include age, gender, allergy information, and/or racial background. Accepting and/or utilizing a physiologically-based pharmacokinetic model may serve to more accurately determine a pharmacokinetic model for an individual. In some instances, physiological model accepter module 3464 may include a computer processor.

Further, operation 4706 illustrates accepting an in vitro-based pharmacokinetic model. For example, as shown in FIGS. 32 through 35, in vitro model accepter module 3466 may accept an in vitro-based pharmacokinetic model. An in vitro-based pharmacokinetic model may include a model derived from a controlled experiment outside of a living organism. One example of an in vitro experiment may include an experiment in a test tube. In one embodiment, in vitro model accepter module 3466 may accept an in vitro-based pharmacokinetic model for morphine developed from a test tube experiment located in a research laboratory. One example of in vitro-based pharmacokinetic modeling software may include DDDPlus, available from Simulations Plus, Inc. Another example of utilizing a physiologic-based simulation model at least partially based on in vitro data may be found in Grass et al., U.S. Pat. No. 6,647,358, which is incorporated herein by reference. In some instances, in vitro model accepter module 3466 may include a computer processor.

Further, operation 4708 illustrates accepting an output from physiologically-based pharmacokinetic modeling software. For example, as shown in FIGS. 32 through 35, software output accepter module 3468 may accept an output from physiologically-based pharmacokinetic modeling software. In one embodiment, software output accepter module 3468 may accept an output from physiologically-based pharmacokinetic modeling software. Accepting an output may include, for example, accepting a digital file with pharmacokinetic information and/or accepting printed information, such as a plasma drug concentration versus time graphed depiction. Some examples of physiologically-based pharmacokinetic modeling software may include, for example, acstXtreme, GNU MCSim, PK-Sim, Simcyp, and/or GastroPlus. In some instances, software output accepter module 3468 may include a computer processor.

Figure 48:
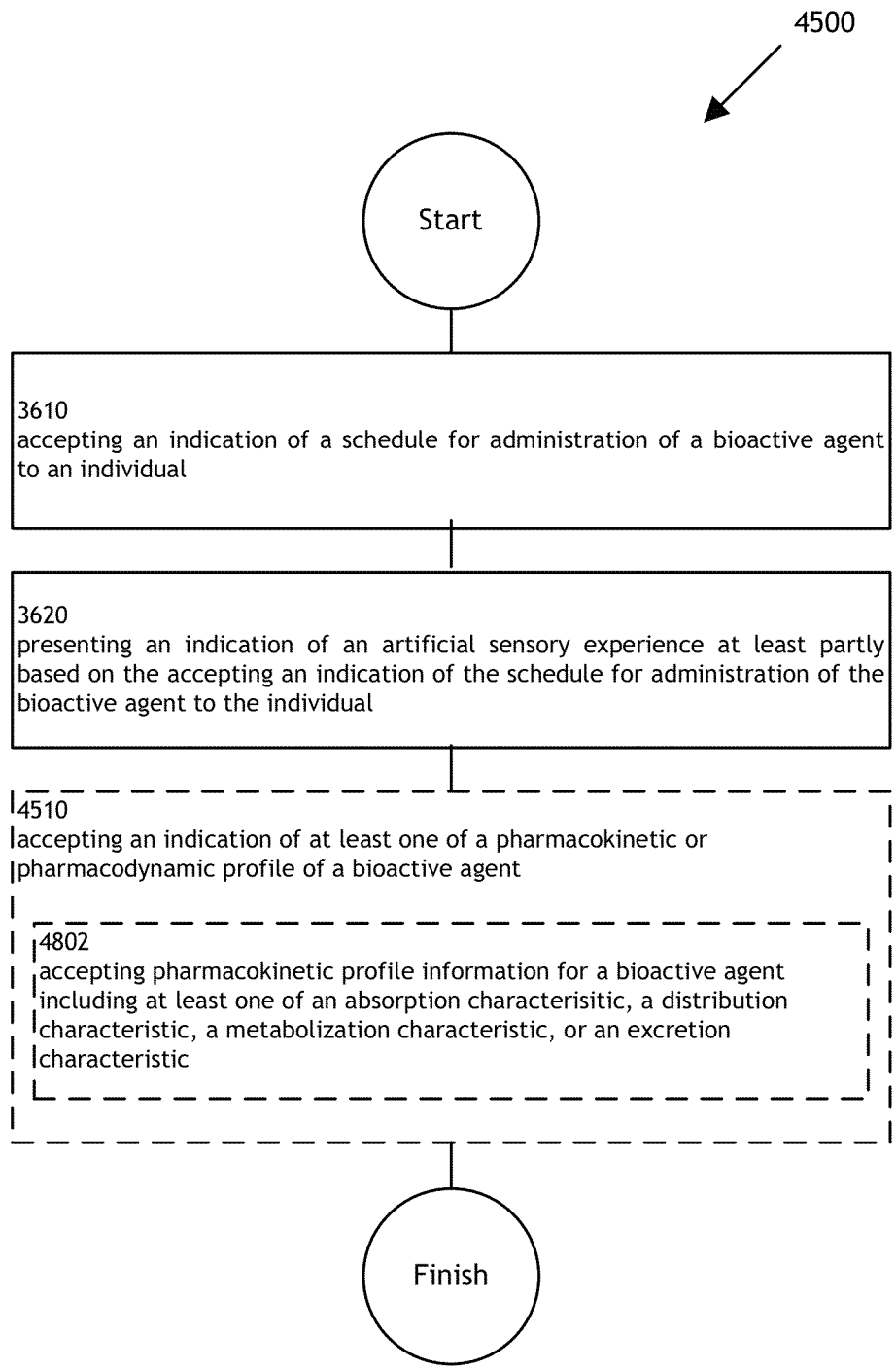
FIG. 48 illustrates an alternative embodiment of the operational flow of FIG. 36.

FIG. 48 illustrates alternative embodiments of the example operational flow 4500 of FIG. 45. FIG. 48 illustrates example embodiments where operation 4510 may include at least one additional operation. Additional operations may include operation 4802.

Operation 4802 illustrates accepting pharmacokinetic profile information for a bioactive agent including at least one of an absorption characteristic, a distribution characteristic, a metabolization characteristic, or an excretion characteristic. For example, as shown in FIGS. 32 through 35, characteristic accepter module 3470 may accept pharmacokinetic profile information for a bioactive agent including at least one of an absorption characteristic, a distribution characteristic, a metabolization characteristic, or an excretion characteristic. An absorption characteristic may include a bioactive agent route of administration, the rate of dissolution of a bioactive agent, and/or ionization of a molecule. In one embodiment, characteristic accepter module 3470 may accept an absorption characteristic including a rate of dissolution for a medication in tablet form having an enteric coating. A distribution characteristic may include permeability between tissues, blood flow and perfusion rate of the tissue, pH parturition, and/or ability of the drug to bind plasma proteins and tissue. In one embodiment, characteristic accepter module 3470 may accept a distribution characteristic for morphine, including a volume of distribution of 3 L/kg of body weight. A metabolization characteristic may include, for example, a metabolic rate and may include and/or be influenced by the presence of a second drug and/or compound. Metabolization may include modification and/or degradation, for example, by an enzyme or enzyme complex. For example, metabolization may include modification of a first drug into a more active version of the first drug and/or a second drug. In one embodiment, characteristic accepter module 3470 may accept a metabolic rate for morphine. An excretion characteristic may include an excretion rate, for example expressed in ng/mL/min. In one embodiment, characteristic accepter module 3470 may accept an excretion characteristic for morphine and/or morphine metabolites, such as 500 ng/mL/min. In some instances, characteristic accepter module 3470 may include a computer processor.

Figure 49:
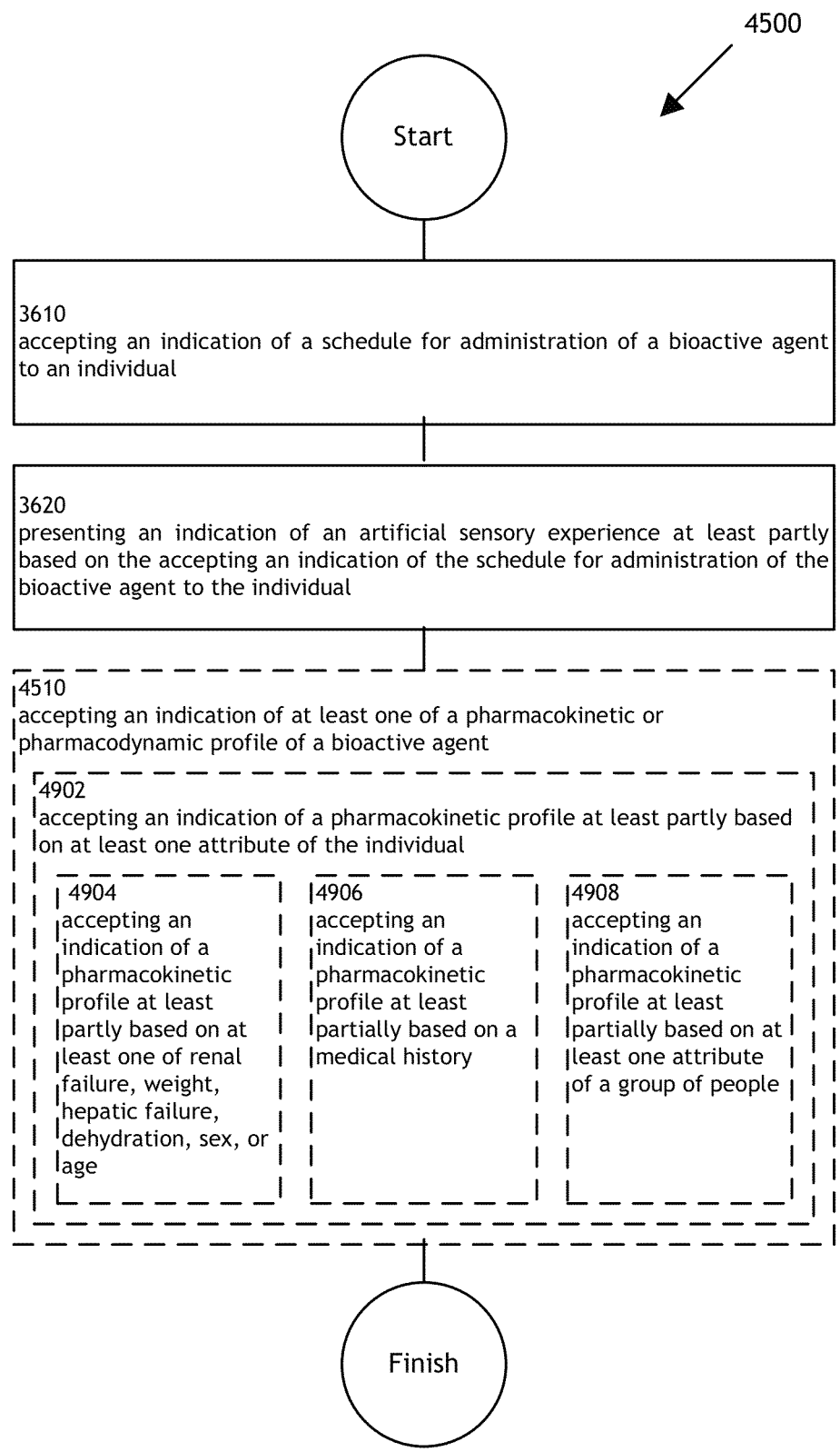
FIG. 49 illustrates an alternative embodiment of the operational flow of FIG. 36.

FIG. 49 illustrates alternative embodiments of the example operational flow 4500 of FIG. 45. FIG. 49 illustrates example embodiments where operation 4510 may include at least one additional operation. Additional operations may include operation 4902, operation 4904, operation 4906, and/or operation 4908.

Operation 4902 illustrates accepting an indication of a pharmacokinetic profile at least partly based on at least one attribute of the individual. For example, as shown in FIGS. 32 through 35, attribute profile accepter module 3472 may accepting an indication of a pharmacokinetic profile at least partly based on at least one attribute of the individual. In one embodiment, attribute profile accepter module 3472 may accept an indication of a pharmacokinetic profile at least partly based on age and weight of an individual. Accepting an indication of a pharmacokinetic profile at least partly based on an attribute of the individual may serve to more accurately predict the effects of a bioactive agent on the individual by more closely matching the individual's attributes with data from pharmaceutical tests involving people similar to the individual. In some instances, attribute profile accepter module 3472 may include a computer processor.

Further, operation 4904 illustrates accepting an indication of a pharmacokinetic profile at least partly based on at least one of renal failure, weight, hepatic failure, dehydration, sex, or age. For example, as shown in FIGS. 32 through 35, physiological characteristic accepter module 3474 may accept an indication of a pharmacokinetic profile at least partly based on at least one of renal failure, obesity, hepatic failure, dehydration, sex, or age. In one embodiment, physiological characteristic accepter module 3474 may accept an indication of a pharmacokinetic profile at Least partly based on obesity and age. Renal failure may include a situation where at least one kidney fails to properly function. Weight may include obesity, abnormal weight, and/or clinically underweight physiology, for example. Obesity may include a situation where body fat accumulates to a harmful degree. Obesity and/or abnormal weight characteristics may be measured and/or assessed using a body mass index. Hepatic failure may include a situation where the Liver is unable to perform its normal metabolic and/or synthetic functions. Dehydration may include the absence and/or removal of water from the body and may negatively affect a bioactive agent effect on an individual. Additionally, sex and age may affect the magnitude of effect the bioactive agent may have on an individual. For example, an elderly person may not be affected as greatly as a young person because of a slower metabolic rate. In some instances, physiological characteristic accepter module 3474 may include a computer processor.

Further, operation 4906 illustrates accepting an indication of a pharmacokinetic profile at least partially based on a medical history. For example, as shown in FIGS. 32 through 35, medical history profile accepter module 3476 may accept an indication of a pharmacokinetic profile at least partially based on a personal medical history. A personal medical history may include a list of previous illnesses, symptoms, medicines, treatments, health risk factors, operations, and/or doctor visits associated with at least one individual. In one embodiment, medical history profile accepter module 3476 may accept an indication of an individualized pharmacokinetic profile based on previously prescribed medications for an individual. An individualized pharmacokinetic profile may serve to more closely tailor a bioactive agent to the therapeutic needs of the individual. For example, an individualized pharmacokinetic profile may take into account absorption rates for a certain family of bioactive agents, such as opioids. If the individual reacts to a first opioid, in a certain way, the individual may react to a second opioid in a similar way. In some instances, medical history profile accepter module 3476 may include a computer processor.

Further, operation 4908 illustrates accepting an indication of a pharmacokinetic profile at least partially based on at least one attribute of a group of people. For example, as shown in FIGS. 32 through 35, group attribute accepter module 3478 may accept an indication of a pharmacokinetic profile at least partially based on at least one attribute of a group of people. In one embodiment, group attribute accepter module 3478 may accept an indication of a pharmacokinetic profile based on the weight of a group of people where the group of people may be similar in weight to the individual. Utilizing a pharmacokinetic profile based on a group of people with at least one similar attribute to the individual may serve to better predict how a bioactive agent may affect the individual. In some instances, group attribute accepter module 3478 may include a computer processor.

Figure 50:
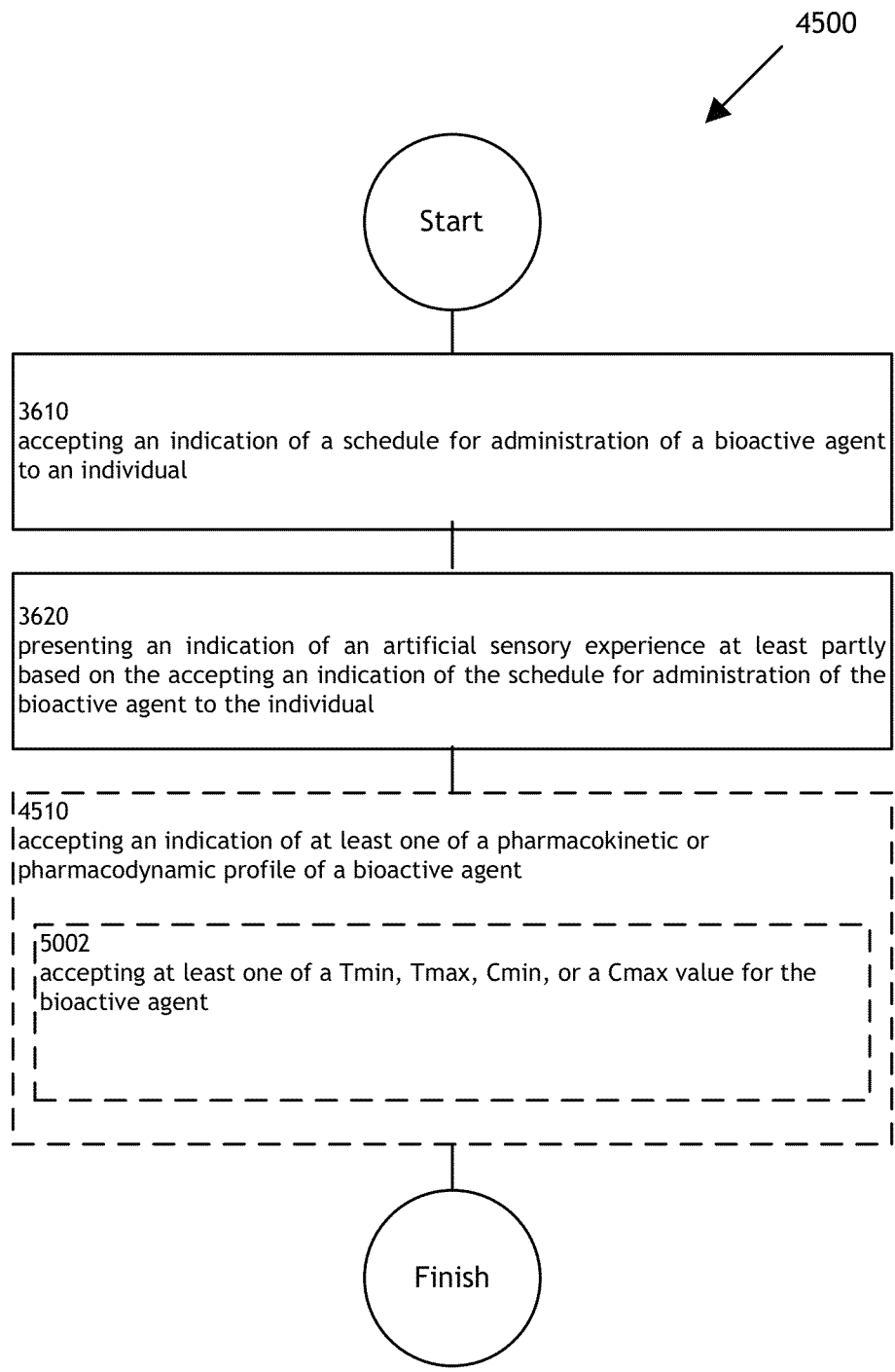
FIG. 50 illustrates an alternative embodiment of the operational flow of FIG. 36.

FIG. 50 illustrates alternative embodiments of the example operational flow 4500 of FIG. 45. FIG. 50 illustrates example embodiments where operation 4510 may include at least one additional operation. Additional operations may include operation 5002.

Operation 5002 illustrates accepting at least one of a Tmin, Tmax, Cmin, or a Cmax value for the bioactive agent. For example, as shown in FIGS. 32 through 35, parameter accepter module 3480 may accept at least one of a Tmin, Tmax, Cmin, or a Cmax value for the bioactive agent. A Tmin value may include a time when a bioactive agent plasma concentration is at a minimum value. A Tmax value may include a time when a bioactive agent plasma concentration is at a maximum value. A Cmin value may include a minimum bioactive agent concentration value. A Cmax value may include a maximum bioactive agent concentration value. In one embodiment, parameter accepter module 3480 may accept a Train and a Tmax value. Accepting a Train and a Tmax value for a bioactive agent during a bioactive agent regimen may serve to help determine an appropriate time to administer a corresponding artificial sensory experience. An appropriate time to administer a corresponding artificial sensory experience may include a time period when a bioactive agent is at a low and/or minimum concentration. An artificial sensory experience may compensate for a low and/or minimum bioactive agent concentration by serving as a distraction. In some instances, parameter accepter module 3480 may include a computer processor.

Figure 51:
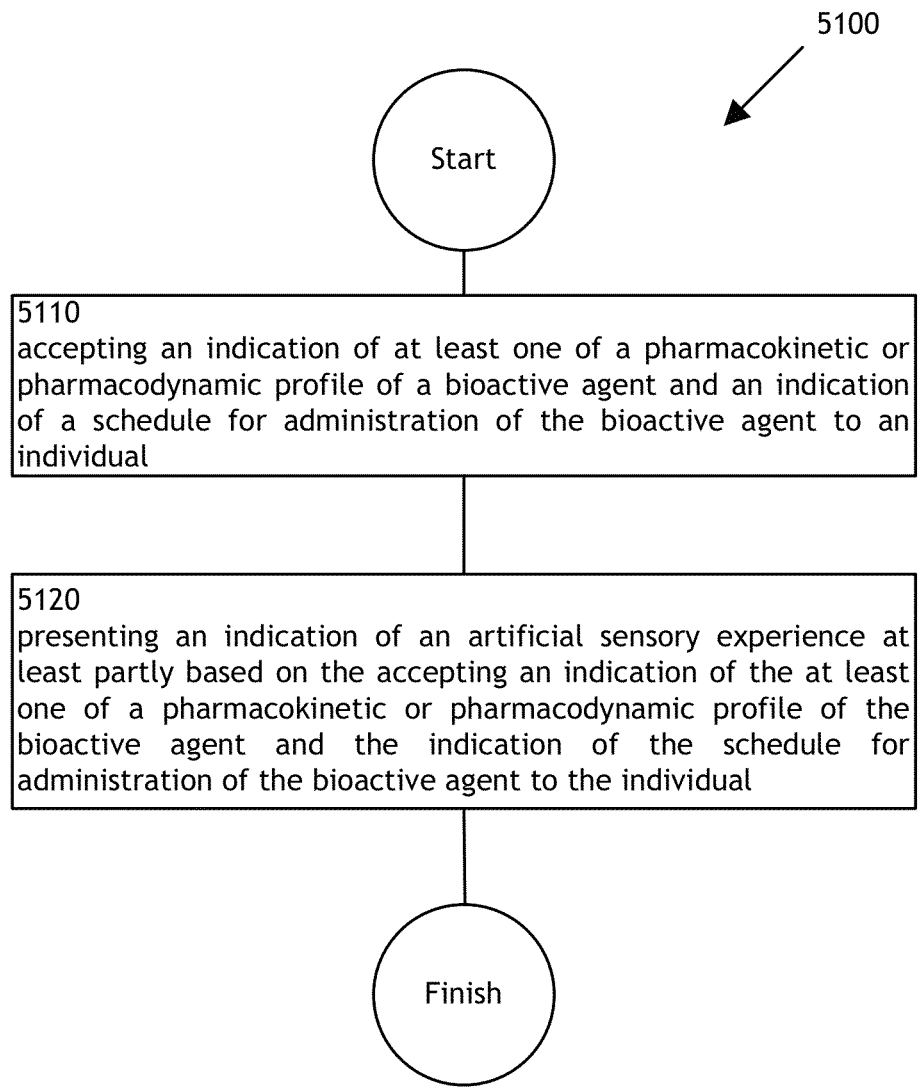
FIG. 51 illustrates an alternative embodiment of the operational flow of FIG. 36.

FIG. 51 illustrates an operational flow 5100 representing example operations related to accepting an indication of at least one of a pharmacokinetic or pharmacodynamic profile of a bioactive agent and an indication of a schedule for administration of the bioactive agent to an individual and/or presenting an indication of an artificial sensory experience at least partly based on the accepting an indication of the at least one of a pharmacokinetic or pharmacodynamic profile of the bioactive agent and the indication of the schedule for administration of the bioactive agent to the individual. In FIG. 51 and in following figures that include various examples of operational flows, discussion and explanation may be provided with respect to the above-described examples of FIGS. 32 through 35, and/or with respect to other examples and contexts. However, it should be understood that the operational flows may be executed in a number of other environments and contexts, and/or in modified versions of FIGS. 32 through 35. Also, although the various operational flows are presented in the sequence(s) illustrated, it should be understood that the various operations may be performed in other orders than those which are illustrated, or may be performed concurrently.

After a start operation, the operational flow 5100 moves to operation 5110. Operation 5110 depicts accepting an indication of at least one of a pharmacokinetic or pharmacodynamic profile of a bioactive agent and an indication of a schedule for administration of the bioactive agent to an individual. For example, as shown in FIGS. 32 through 35, accepter module 3402 may accept an indication of at least one of a pharmacokinetic or pharmacodynamic profile of a bioactive agent and an indication of a schedule for administration of the bioactive agent to an individual. In one embodiment, accepter module 3402 may accept an indication of a pharmacokinetic profile for an opioid and a schedule for an intravenous administration of the opioid to an individual. In this embodiment, the schedule may include specific times and/or methods that the bioactive agent may be administered. For example, a time schedule may specify that an individual should receive a specific dose of morphine every two hours. In another example, an administration schedule may specify that an opioid should be administered intravenously at night and orally during waking hours. In some instances, accepter module 3402 may include a computer processor and/or a user interface coupled to the computer processor.

Then, operation 5120 depicts presenting an indication of an artificial sensory experience at least partly based on the accepting an indication of the at least one of a pharmacokinetic or pharmacodynamic profile of the bioactive agent and the indication of the schedule for administration of the bioactive agent to the individual. For example, as shown in FIGS. 32 through 35, presenter module 3410 may present an indication of an artificial sensory experience at least partly based on the accepting an indication of the at least one of a pharmacokinetic or pharmacodynamic profile of the bioactive agent and the indication of the schedule for administration of the bioactive agent to the individual. In one embodiment, presenter module 3410 may present an indication of a virtual world configured for distracting an individual at least partly based on accepting an indication of a pharmacokinetic profile for morphine and an administration time schedule. In this embodiment, the bioactive administration schedule may be coordinated so that an artificial sensory experience is administered when the morphine may be less effective. Coordinating an artificial sensory experience administration schedule may serve to more efficiently distract and/or reduce, for example, an individual's pain during a period of low bioactive agent concentration in an individual's blood. In some instances, presenter module 3410 may include a computer processor, a display, and/or a printer.

Figure 52:
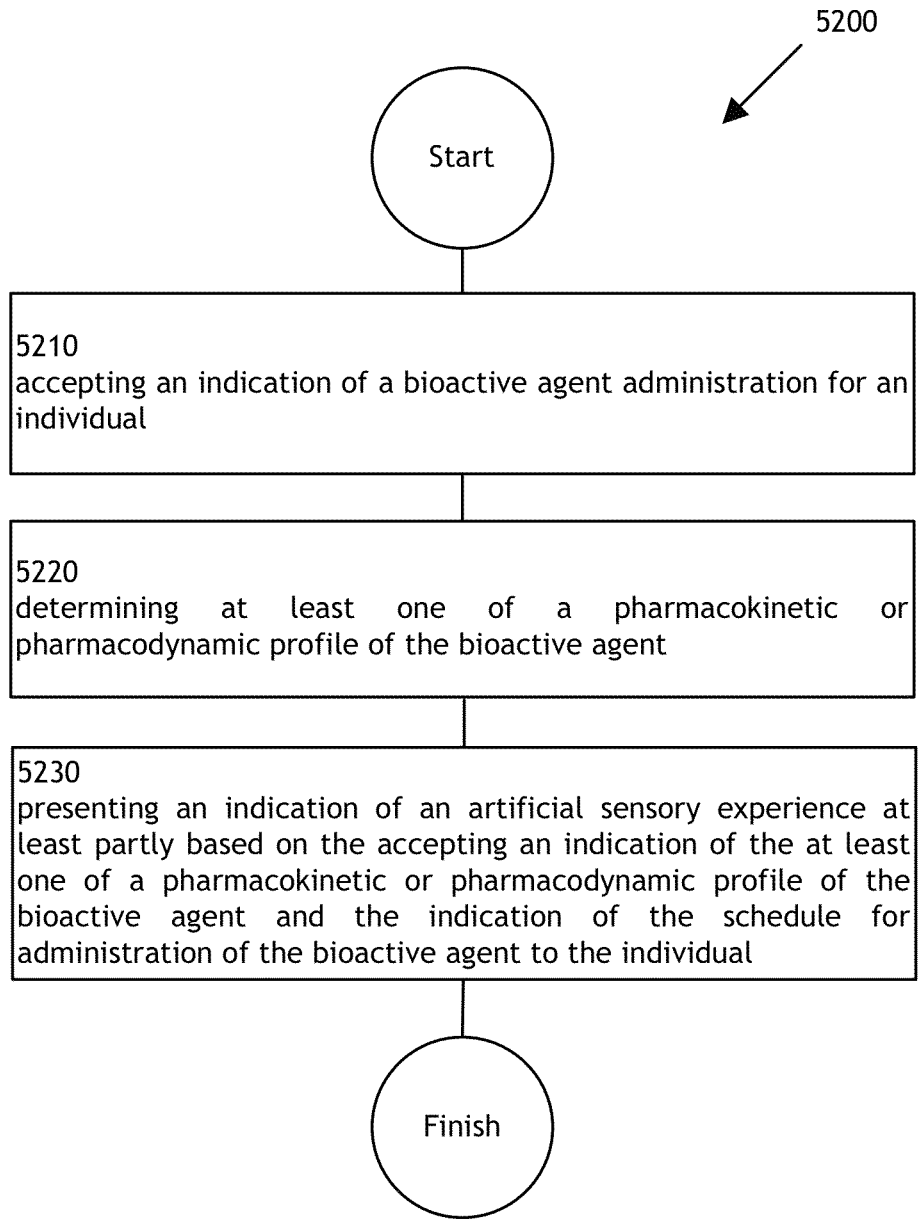
FIG. 52 illustrates an alternative embodiment of the operational flow of FIG. 36.

FIG. 52 illustrates an operational flow 5200 representing example operations related to accepting an indication of a bioactive agent administration for an individual, determining at least one of a pharmacokinetic or pharmacodynamic profile of the bioactive agent, and/or presenting an indication of an artificial sensory experience at least partly based on the accepting an indication of the at least one of a pharmacokinetic or pharmacodynamic profile of the bioactive agent and the indication of the schedule for administration of the bioactive agent to the individual. In FIG. 52 and in following figures that include various examples of operational flows, discussion and explanation may be provided with respect to the above-described examples of FIGS. 32 through 35, and/or with respect to other examples and contexts. However, it should be understood that the operational flows may be executed in a number of other environments and contexts, and/or in modified versions of FIGS. 32 through 35. Also, although the various operational flows are presented in the sequence(s) illustrated, it should be understood that the various operations may be performed in other orders than those which are illustrated, or may be performed concurrently.

After a start operation, the operational flow 5200 moves to operation 5210. Operation 5210 depicts accepting an indication of a bioactive agent administration for an individual. For example, as shown in FIGS. 32 through 35, accepter module 3402 may accept an indication of a bioactive agent administration for an individual. In one embodiment, accepter module 3402 may accept an indication of an administration of an analgesic, such as naproxen. Accepting an indication of an administration of a bioactive agent may include, for example, accepting an administration schedule, accepting a delivery method, and/or accepting a bioactive agent type. In some instances, accepter module 3402 may include a computer processor and/or a user interface coupled to the computer processor.

Then, operation 5220 depicts determining at Least one of a pharmacokinetic or pharmacodynamic profile of the bioactive agent. For example, as shown in FIGS. 32 through 35, determiner module 3482 may determine at least one of a pharmacokinetic or pharmacodynamic profile of the bioactive agent. In one embodiment, determiner module 3482 may determine at least one of a pharmacokinetic profile of an analgesic, such as naproxen. Determining at least one of a pharmacokinetic or pharmacodynamic profile for a bioactive agent may include using a medical history, such as a personal medical history including personal medication efficacy and/or individual attributes (gender, weight, height, etc.). Additionally, determiner module 3482 may determine a pharmacokinetic and/or pharmacodynamic profile for a bioactive agent by comparing an individual's characteristics with predetermined computable pharmacokinetic and/or pharmacodynamic profiles, for example from a database. In some instances, determiner module 3482 may include a computer processor.

Then, operation 5220 depicts presenting an indication of an artificial sensory experience at least partly based on the accepting an indication of the at least one of a pharmacokinetic or pharmacodynamic profile of the bioactive agent and the indication of the schedule for administration of the bioactive agent to the individual. For example, as shown in FIGS. 32 through 35, presenter module 3410 may present an indication of an artificial sensory experience at least partly based on the accepting an indication of the at least one of a pharmacokinetic or pharmacodynamic profile of the bioactive agent and the indication of the schedule for administration of the bioactive agent to the individual. In one embodiment, presenter module 3410 may present to a computer monitor an indication of a virtual world based on accepting an indication of a pharmacokinetic profile for naproxen and an indication of an administration schedule for the naproxen. The indication of the artificial sensory experience may be presented, for example, by displaying the indication on a display device, such as a computer monitor, a mobile device, such as a Blackberry device, and/or a printer device, such as a printed piece of paper from a laser printer. In some instances, presenter module 3410 may include a computer processor and/or a display device, such as a computer monitor and/or a printer.

Figure 53:
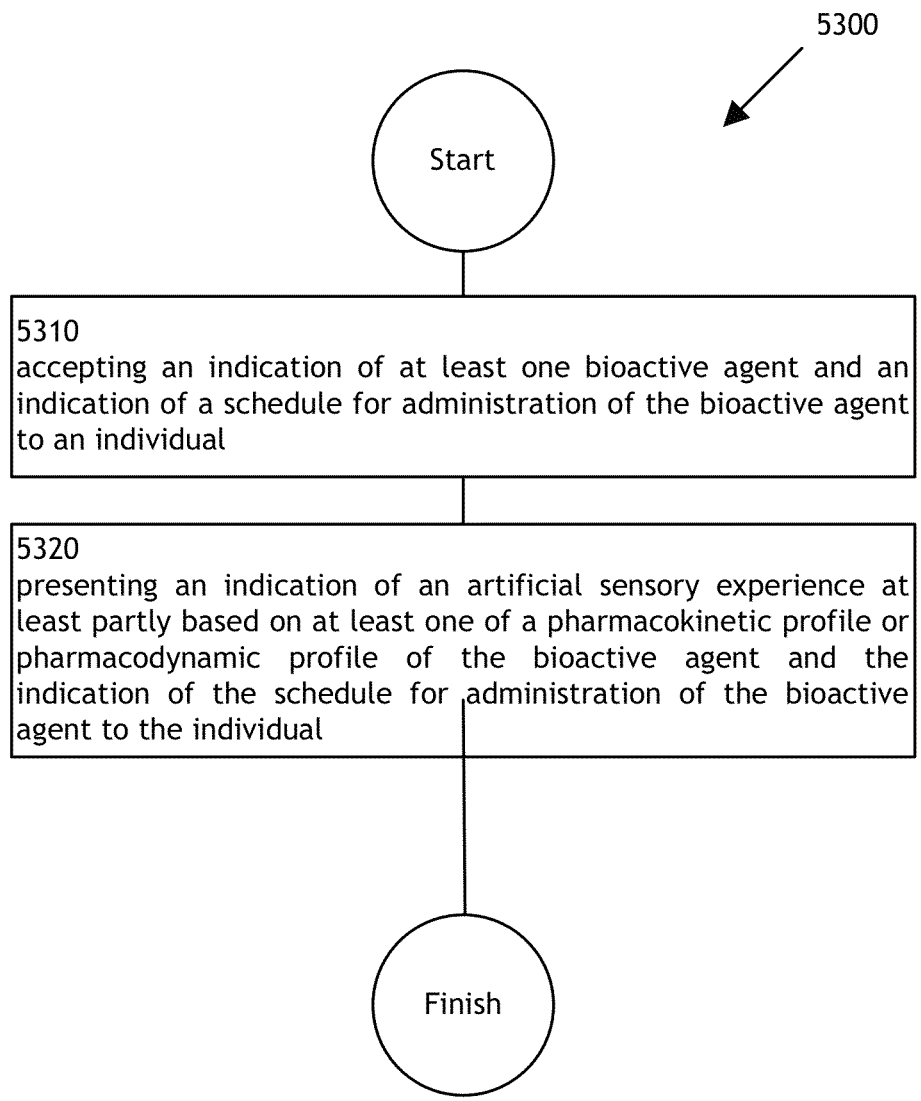
FIG. 53 illustrates an alternative embodiment of the operational flow of FIG. 36.

FIG. 53 illustrates an operational flow 5300 representing example operations related to accepting an indication of at least one bioactive agent and an indication of a schedule for administration of the bioactive agent to an individual and/or presenting an indication of an artificial sensory experience at least partly based on at least one of a pharmacokinetic profile or pharmacodynamic profile of the bioactive agent and the indication of the schedule for administration of the bioactive agent to the individual. In FIG. 53 and in following figures that include various examples of operational flows, discussion and explanation may be provided with respect to the above-described examples of FIGS. 32 through 35, and/or with respect to other examples and contexts. However, it should be understood that the operational flows may be executed in a number of other environments and contexts, and/or in modified versions of FIGS. 32 through 35. Also, although the various operational flows are presented in the sequence(s) illustrated, it should be understood that the various operations may be performed in other orders than those which are illustrated, or may be performed concurrently.

After a start operation, the operational flow 5300 moves to operation 5310. Operation 5310 depicts accepting an indication of at least one bioactive agent and an indication of a schedule for administration of the bioactive agent to an individual. For example, as shown in FIGS. 32 through 35, accepter module 3402 may accept an indication of at least one bioactive agent and an indication of a schedule for administration of the bioactive agent to an individual. In one embodiment, accepter module 3402 may accept an indication of an analgesic, such as ibuprofen, and accept an indication of an administration of the ibuprofen. Accepting an indication of a bioactive agent may include, for example, accepting an indication of a prescription medication from a health care provider. Additionally, an indication of a bioactive agent may be accepted from a computer database. Accepting an indication of a bioactive agent administration schedule may include specific times and/or methods that the bioactive agent may be administered. Additionally, a bioactive agent administration schedule may include receiving a dose with or without food, which may be specific food, and/or together with or separate from other drugs. For example, a time schedule may specify that an individual should receive a specific dose of ibuprofen every two hours. In another example, an administration schedule may specify that an analgesic should be administered intravenously at night and orally during waking hours. Accepting an indication of an administration schedule may include accepting a delivery method and/or accepting a bioactive agent to be administered. In some instances, accepter module 3402 may include a computer processor and/or a user interface coupled to the computer processor.

Then, operation 5320 depicts presenting an indication of an artificial sensory experience at Least partly based on the accepting an indication of the at least one of a pharmacokinetic or pharmacodynamic profile of the bioactive agent and the indication of the schedule for administration of the bioactive agent to the individual. For example, as shown in FIGS. 32 through 35, presenter module 3410 may present an indication of an artificial sensory experience at least partly based on the accepting an indication of the at least one of a pharmacokinetic or pharmacodynamic profile of the bioactive agent and the indication of the schedule for administration of the bioactive agent to the individual. In one embodiment, presenter module 3410 may present to a computer monitor an indication of a virtual world based on accepting an indication of a pharmacokinetic profile for ibuprofen and an indication of an administration schedule for the ibuprofen. The indication of the artificial sensory experience may be presented, for example, by displaying the indication on a display device, such as a computer monitor, a mobile device, such as a Blackberry device, and/or a printer device, such as a printed piece of paper from a laser printer. In some instances, presenter module 3410 may include a computer processor and/or a display device, such as a computer monitor and/or a printer.

Figure 54:
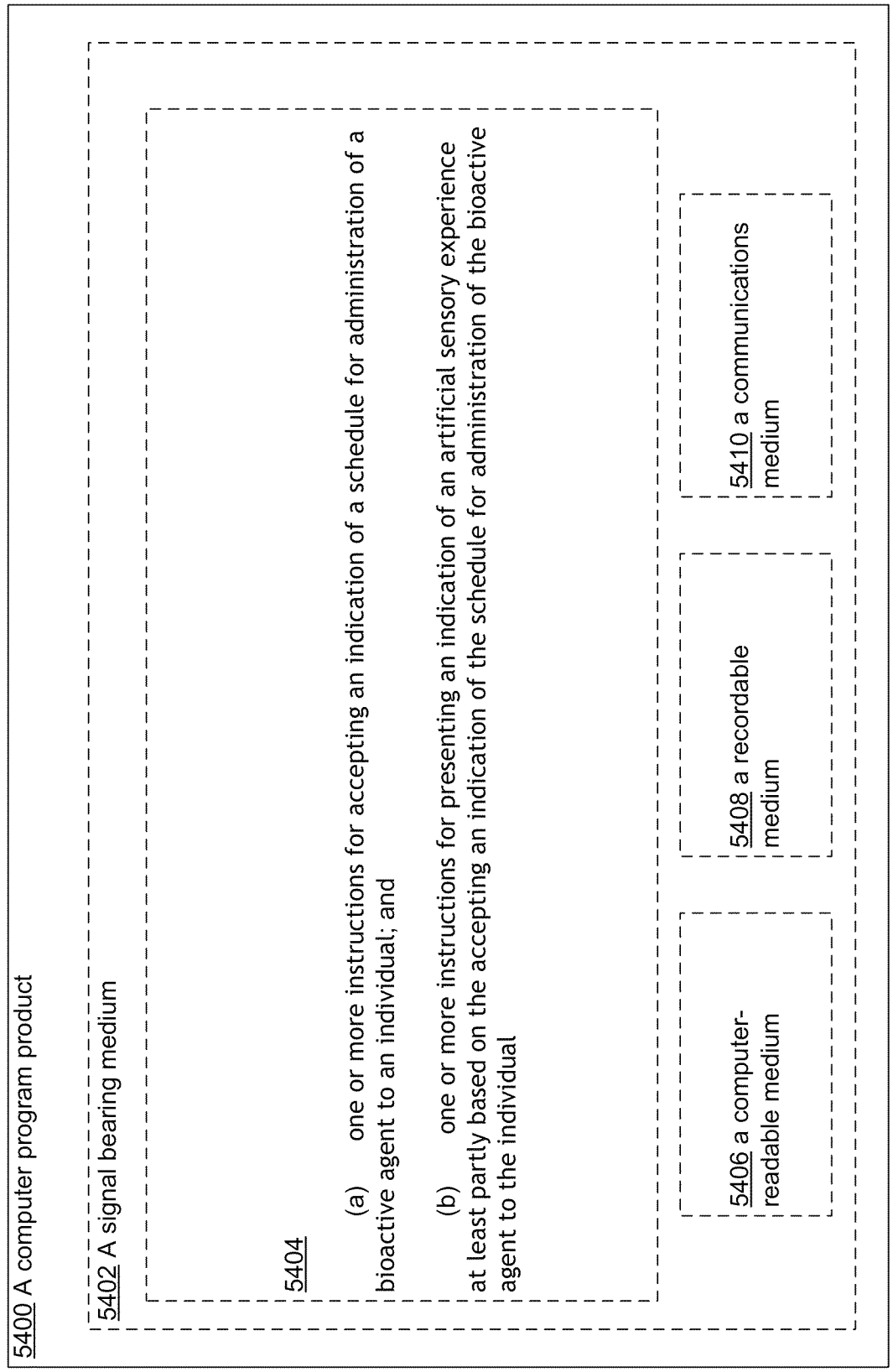
FIG. 54 illustrates a computer program product related to presenting an indication of an artificial sensory experience.

FIG. 54 illustrates a partial view of an example computer program product 5400 that includes a computer program 5404 for executing a computer process on a computing device. An embodiment of the example computer program product 5400 is provided using a signal-bearing medium bearing 5402, and may include one or more instructions for accepting an indication of a schedule for administration of a bioactive agent to an individual and one or more instructions for presenting an indication of an artificial sensory experience at least partly based on the accepting an indication of the schedule for administration of the bioactive agent to the individual. The one or more instructions may be, for example, computer executable and/or logic-implemented instructions. In one implementation, the signal-bearing medium 5402 may include a computer-readable medium 5406. In one implementation, the signal bearing medium 5402 may include a recordable medium 5408. In one implementation, the signal bearing medium 5402 may include a communications medium 5410.

Figure 55:
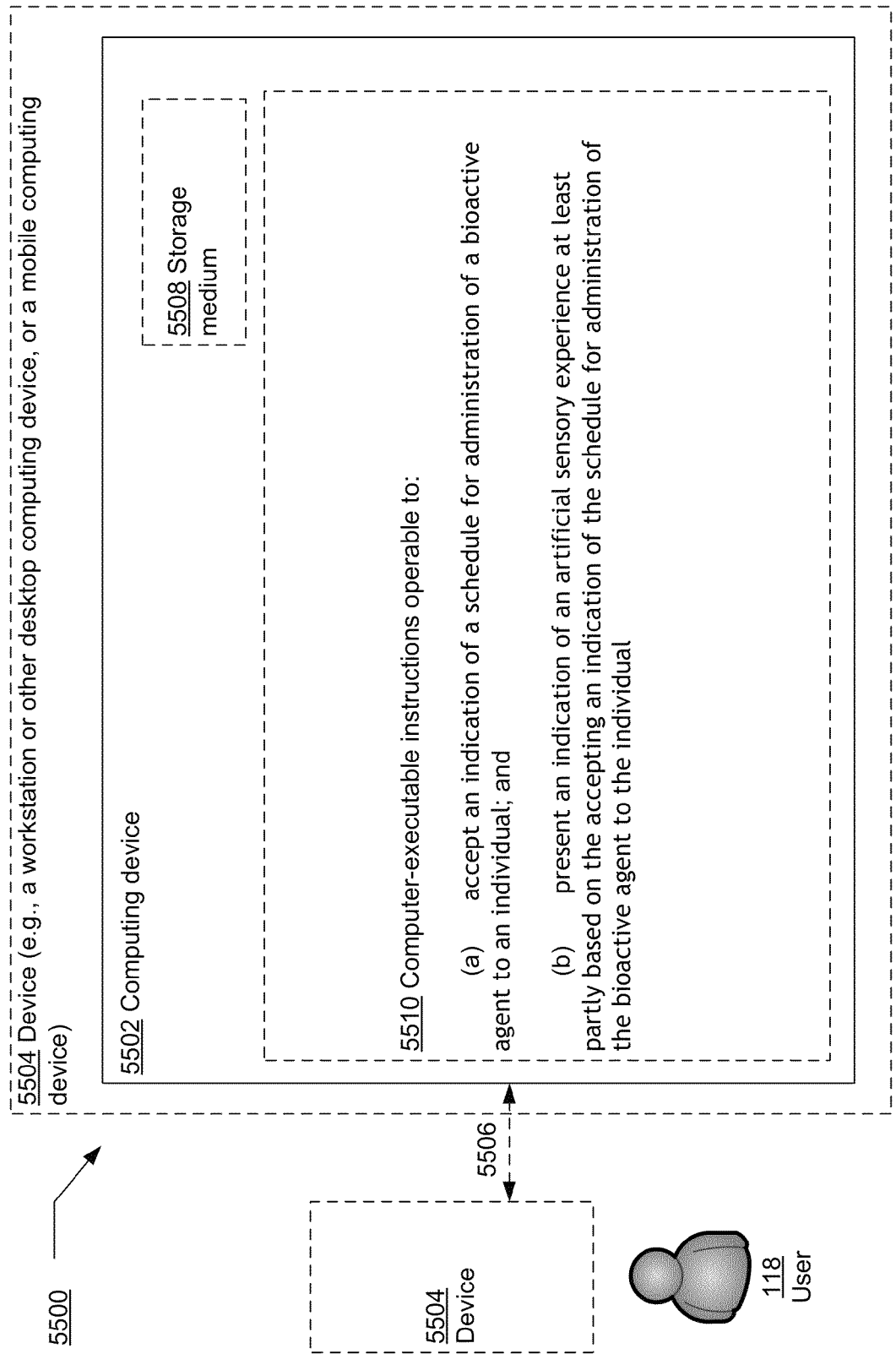
FIG. 55 illustrates a system related to presenting an indication of an artificial sensory experience.

FIG. 55 illustrates an example system 5500 in which embodiments may be implemented. The system 5500 includes a computing system environment. The system 5500 also illustrates the user 118 using a device 5504, which is optionally shown as being in communication with a computing device 5502 by way of an optional coupling 5506. The optional coupling 5506 may represent a local, wide-area, or peer-to-peer network, or may represent a bus that is internal to a computing device (e.g., in example embodiments in which the computing device 5502 is contained in whole or in part within the device 5504). A storage medium 5508 may be any computer storage media.

The computing device 5502 includes computer-executable instructions 5510 that when executed on the computing device 5502 cause the computing device 5502 to accept an indication of a schedule for administration of a bioactive agent to an individual and present an indication of an artificial sensory experience at least partly based on the accepting an indication of the schedule for administration of the bioactive agent to the individual. As referenced above and as shown in FIG. 55, in some examples, the computing device 5502 may optionally be contained in whole or in part within the device 5504.

In FIG. 55, then, the system 5500 includes at least one computing device (e.g., 5502 and/or 5504). The computer-executable instructions 5510 may be executed on one or more of the at least one computing device. For example, the computing device 5502 may implement the computer-executable instructions 5510 and output a result to (and/or receive data from) the computing device 5504. Since the computing device 5502 may be wholly or partially contained within the computing device 5504, the device 5504 also may be said to execute some or all of the computer-executable instructions 5510, in order to be caused to perform or implement, for example, various ones of the techniques described herein, or other techniques.

The device 5504 may include, for example, a portable computing device, workstation, or desktop computing device. In another example embodiment, the computing device 5502 is operable to communicate with the device 5504 associated with the user 118 to receive information about the input from the user 118 for performing data access and data processing and presenting an output of the user-health test function at least partly based on the user data.

Although a user 118 is shown/described herein as a single illustrated figure, those skilled in the art will appreciate that a user 118 may be representative of a human user, a robotic user (e.g., computational entity), and/or substantially any combination thereof (e.g., a user may be assisted by one or more robotic agents). In addition, a user 118, as set forth herein, although shown as a single entity may in fact be composed of two or more entities. Those skilled in the art will appreciate that, in general, the same may be said of "sender" and/or other entity-oriented terms as such terms are used herein.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction Left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence, in some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication Link (e.g., transmitter, receiver, transmission logic, reception logic, etc.), etc.).

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at Least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not Limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback Loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are Located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or an limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at Least two recitations, or two or more recitations). Furthermore, in those instances where a convention analogous to "at least one of A, B, and C, etc." is used, in general such a construction is intended in the sense one having skill in the art would understand the convention (e.g., "a system having at Least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at Least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art wilt appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   at least one dispenser operable to release one or more unit dosages of at least one anti-addiction agent;
   at least one anti-addiction agent disposed within the at least one dispenser for release in accordance with at least one administration schedule; and
   one or more media associated with the at least one dispenser, the one or more non-transitory media bearing one or more codes for accessing online digital content for implementation of at least one digital therapy application, the one or more codes associated with the at least one dispenser being readable by
   at least one smartphone device including at least:
      at least one user interface,
      at least one wireless transceiver; and
      at least one processor component, to perform special purpose operations including at least:
         configuring the at least one processor component to output at least one indication to administer the at least one anti-addiction agent of the at least one dispenser in accordance with the at least one administration schedule,
         configuring the at least one processor component to implement the at least one digital therapy application at one or more times that is coordinated with at least one time of administration of the at least one anti-addiction agent based on at least one pharmacokinetic profile of the at least one anti-addiction agent,
         configuring the at least one processor component to monitor at least one effect on an individual at one or more specified times relative to implementation of the at least one digital therapy application and administration of the at least one anti-addiction agent, and
         configuring the at least one processor component to transmit wirelessly at least one aggregation of one or more health results for access by at least one health provider.

2. A computer process for controlling a system that includes at least one dispenser including at least one anti-addiction agent for release in accordance with at least one administration schedule and one or more media bearing one or more codes for accessing online digital content for implementation of at least one digital therapy application, and at least one smartphone device including at least one user interface, at least one wireless transceiver, and at least one processor component, the computer process including special purpose operations comprising:

outputting by the at least one processor component at least one indication to administer the at least one anti-addiction agent of the at least one dispenser in accordance with the at least one administration schedule;

implementing by the at least one processor component the at least one digital therapy application at one or more times that is coordinated with at least one time of administration of the at least one anti-addiction agent based on at least one window of effectiveness of the at least one anti-addiction agent;

monitoring by the at least one processor component at least one effect on an individual at one or more specified times relative to implementation of the at least one digital therapy application and administration of the at least one anti-addiction agent; and transmitting wirelessly by the at least one wireless transceiver at least one aggregation of one or more health results for access by at least one health provider.

3. A computer process for controlling a system that includes at least one dispenser including at least one pharmaceutical agent for administration, and at least one smartphone device including at least one communication device, at least one processor component, and at least one user interface, the computer process including special purpose operations comprising:

obtaining by the at least one processor component information from the at least one dispenser for accessing at least one interactive experience for implementation on the at least one smartphone device;

outputting by the at least one processor component one or more instructions to administer at least one dosage of the at least one pharmaceutical agent from the at least one dispenser at one or more specified times;

implementing by the at least one processor component at least one aspect of the at least one interactive experience at one or more times relative to administration of the at least one pharmaceutical agent, the one or more times corresponding to one or more levels of effectiveness of the at least one pharmaceutical agent; and detecting one or more specified reactions of an individual based at least partly on at least one test function at least partly in response to implementation of the at least one aspect of the at least one interactive experience.

4. The process of claim 3, further comprising:
reporting at least one monitored effect to at least one medical professional.

5. The process of claim 3, further comprising:
reporting compliance data to at least one medical professional.

6. The process of claim 3, wherein the obtaining by the at least one processor component information from the at least one dispenser for accessing at least one interactive experience for implementation on the at least one smartphone device comprises:

obtaining by the at least one processor component one or more digital codes from one or more media associated with the at least one dispenser for accessing at least one interactive experience for implementation on the at least one smartphone device.

7. The process of claim 3, wherein the obtaining by the at least one processor component information from the at least one dispenser for accessing at least one interactive experience for implementation on the at least one smartphone device comprises:

obtaining by the at least one processor component information from the at least one dispenser for accessing at least one of the following types of interactive experiences for implementation on the at least one smartphone device: digital therapy, virtual world, computer game, online course, visual stimulus, or auditory stimulus.

8. The process of claim 3, wherein the obtaining by the at least one processor component information from the at least one dispenser for accessing at least one interactive experience for implementation on the at least one smartphone device comprises:

obtaining by the at least one processor component information from the at least one nasal, intravenous, physical intervention module, or container dispenser for accessing at least one interactive experience for implementation on the at least one smartphone device.

9. The process of claim 3, wherein the outputting by the at least one processor component one or more instructions to administer at least one dosage of the at least one pharmaceutical agent from the at least one dispenser at one or more specified times comprises:

outputting by the at least one processor component one or more instructions to administer at least one dosage of the at least one pharmaceutical agent from the at least one dispenser at one or more specified times to treat at least one mental condition.

10. The process of claim 3, wherein the outputting by the at least one processor component one or more instructions to administer at least one dosage of the at least one pharmaceutical agent from the at least one dispenser at one or more specified times comprises:

outputting by the at least one processor component one or more instructions to administer at least one dosage of the at least one anti-addiction or withdrawal pharmaceutical agent from the at least one dispenser at one or more specified times.

11. The process of claim 3, wherein the outputting by the at least one processor component one or more instructions to administer at least one dosage of the at least one pharmaceutical agent from the at least one dispenser at one or more specified times comprises:

outputting by the at least one processor component one or more instructions to administer at least one dosage of the at least one anti-anxiety pharmaceutical agent from the at least one dispenser at one or more specified times.

12. The process of claim 3, wherein the outputting by the at least one processor component one or more instructions to administer at least one dosage of the at least one pharmaceutical agent from the at least one dispenser at one or more specified times comprises:

outputting by the at least one processor component one or more instructions to administer at least one dosage of the at least one pharmaceutical agent from the at least one dispenser at one or more specified times to treat at least one of the following types of conditions: anxiety, behavior, depression, fear, inattention, mood disturbance, phobia, psychotic disorder, eating disorder, developmental disorder, communication disorder, social disorder, panic disorder, schizophrenia, obsessive compulsive disorder, addiction, or personality disorder.

13. The process of claim 3, wherein the outputting by the at least one processor component one or more instructions to administer at least one dosage of the at least one pharmaceutical agent from the at least one dispenser at one or more specified times comprises:

outputting by the at least one processor component to the at least one user interface one or more instructions to administer at least one dosage of the at least one pharmaceutical agent from the at least one dispenser at one or more specified times.

14. The process of claim 3, wherein the implementing by the at least one processor component at least one aspect of the at least one interactive experience at one or more times relative to administration of the at least one pharmaceutical agent, the one or more times corresponding to one or more levels of effectiveness of the at least one pharmaceutical agent comprises:

implementing by the at least one processor component at least one aspect of the at least one interactive experience at one or more times relative to administration of the at least one pharmaceutical agent, the one or more times corresponding to one or more times when plasma concentration of the at least one pharmaceutical agent is expected to be below a substantially effective level based on a pharmacokinetic profile of the at least one pharmaceutical agent and an administration schedule of the at least one pharmaceutical agent.

15. The process of claim 3, wherein the implementing by the at least one processor component at least one aspect of the at least one interactive experience at one or more times relative to administration of the at least one pharmaceutical agent, the one or more times corresponding to one or more levels of effectiveness of the at least one pharmaceutical agent comprises:

implementing by the at least one processor component at least one aspect of the at least one interactive experience at one or more times relative to administration of the at least one pharmaceutical agent, the one or more times being based at least partly on a pharmacokinetic profile that is determined based on at least one attribute of an individual to whom the at least one pharmaceutical agent is administered.

16. The process of claim 3, wherein the implementing by the at least one processor component at least one aspect of the at least one interactive experience at one or more times relative to administration of the at least one pharmaceutical agent, the one or more times corresponding to one or more levels of effectiveness of the at least one pharmaceutical agent comprises:

implementing by the at least one processor component at least one aspect of the at least one interactive experience at one or more times relative to administration of the at least one pharmaceutical agent, the one or more times corresponding to at least one of concentration or bioavailability of the at least one pharmaceutical agent.

17. The process of claim 3, wherein the implementing by the at least one processor component at least one aspect of the at least one interactive experience at one or more times relative to administration of the at least one pharmaceutical agent, the one or more times corresponding to one or more levels of effectiveness of the at least one pharmaceutical agent comprises:

implementing by the at least one processor component at least one aspect of the at least one interactive experience at one or more times relative to administration of the at least one pharmaceutical agent, the one or more times corresponding to one or more peak levels of effectiveness of the at least one pharmaceutical agent.

18. The process of claim 3, wherein the obtaining by the at least one processor component information from the at least one dispenser for accessing at least one interactive experience for implementation on the at least one smartphone device comprises:

obtaining by the at least one processor component one or more digital codes from at least one packaging unit dispenser for accessing at least one interactive experience for implementation on the at least one smartphone device.

19. The process of claim 3, wherein the implementing by the at least one processor component at least one aspect of the at least one interactive experience at one or more times relative to administration of the at least one pharmaceutical agent, the one or more times corresponding to one or more levels of effectiveness of the at least one pharmaceutical agent comprises:

implementing by the at least one processor component at least one aspect of the at least one interactive experience at one or more times relative to administration of the at least one pharmaceutical agent, the one or more times corresponding to one or more lowest levels of effectiveness of the at least one pharmaceutical agent.

20. The process of claim 3, wherein the implementing by the at least one processor component at least one aspect of the at least one interactive experience at one or more times relative to administration of the at least one pharmaceutical agent, the one or more times corresponding to one or more levels of effectiveness of the at least one pharmaceutical agent comprises:

implementing by the at least one processor component at least one aspect of the at least one interactive experience at one or more staggered times relative to administration of the at least one pharmaceutical agent, the one or more staggered times corresponding to one or more levels of effectiveness of the at least one pharmaceutical agent.

21. The process of claim 3, wherein the detecting one or more specified reactions of an individual based at least partly on at least one test function at least partly in response to implementation of the at least one aspect of the at least one interactive experience comprises:

detecting one or more of the following parameters of an individual based at least partly in response to implementation of the at least one aspect of the at least one interactive experience: visual field, eye movement, pupil movement, face pattern, motor skill, iris dilation, iris constriction, input, gaze tracking, skin response, physical activity, body weight, body mass, heart rate, blood oxygen level, blood pressure, physiological activity, brain activity, behavior, compliance, voice, or hearing.

22. The process of claim 3, wherein the detecting one or more specified reactions of an individual based at least partly on at least one test function at least partly in response to implementation of the at least one aspect of the at least one interactive experience comprises:

detecting one or more specified reactions of an individual based at least partly on at least one test function in near real-time or real-time to implementation of the at least one aspect of the at least one interactive experience.

23. A system comprising:

at least one dispenser operable to release one or more unit dosages of at least one pharmaceutical agent and comprising one or more codes, the one or more codes associated with the at least one dispenser being readable by at least one smartphone device to perform operations including at least:

outputting at least one indication to administer the at least one pharmaceutical agent of the at least one dispenser in accordance with at least one administration schedule, implementing the at least one digital therapy application at one or more times that is coordinated with at least one time of administration of the at least one pharmaceutical agent based on at least one level of effectiveness of the at least one pharmaceutical agent, monitoring at least one effect on an individual at one or more specified times relative to implementation of the at least one digital therapy application and administration of the at least one pharmaceutical agent, and transmitting wirelessly one or more monitoring results for access by at least one health provider.

24. The system of claim 23, wherein the at least one dispenser operable to release one or more unit dosages of at least one pharmaceutical agent comprises:

at least one blister pack containing one or more unit dosages of at least one pharmaceutical agent for release.

* * * * *